(12) United States Patent
Blagg et al.

(10) Patent No.: US 8,685,966 B2
(45) Date of Patent: Apr. 1, 2014

(54) GRP94 INHIBITORS

(75) Inventors: Brian S. J. Blagg, Lawrence, KS (US); Adam S. Duerfeldt, San Diego, CA (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 13/441,568

(22) Filed: Apr. 6, 2012

(65) Prior Publication Data

US 2013/0109684 A1 May 2, 2013

Related U.S. Application Data

(60) Provisional application No. 61/473,343, filed on Apr. 8, 2011.

(51) Int. Cl.
*A61K 31/26* (2006.01)

(52) U.S. Cl.
USPC .................................................. 514/230.5

(58) Field of Classification Search
USPC .................................................. 514/230.5
See application file for complete search history.

(56) References Cited

U.S. PATENT DOCUMENTS

| | | | |
|---|---|---|---|
| 6,046,239 | A | 4/2000 | Lennox et al. |
| 6,177,575 | B1 | 1/2001 | Arduengo, III et al. |
| 7,208,630 | B2 | 4/2007 | Blagg et al. |
| 7,605,288 | B2 | 10/2009 | Blagg et al. |
| 2005/0187277 | A1 | 8/2005 | Mjalli et al. |
| 2006/0089495 | A1 | 4/2006 | Blagg et al. |
| 2009/0036438 | A1 | 2/2009 | Hangeland et al. |
| 2009/0312326 | A1 | 12/2009 | Chubb et al. |

OTHER PUBLICATIONS

Brandt, G. and Blagg, B. Alternate Strategies of HSP90 Modulation for the Treatment of Cancer and Other Diseases, Curr. Top Med Chem., 2009: 9(15):1447-1461.*
Biamonte, M. et al., Heat shock Protein 90: Inhibitors in Clinical Trials., J. Med. Chem. 2010, 53, 3-17.*
Altman and Buchwald, 4,7-Dimethoxy-1, 10-phenanthroline: An Excellent Ligand for the Cu-Catalyzed N-Arylation of Imidazoles. *Org. Lett.*, 8(13) 2006, pp. 2779-2782.
Biamonte, M. A.; Van de Water, R.; Arndt, J. W.; Scannevin, R. H.; Perret, D.; Lee, W. Heat shock protein 90: Inhibitors in clinical trials . *J. Med. Chem.* 2010, 53, 3-17.
Bishop, S. C.; Burlison, J. A.; Blagg, B. S. J. Hsp90: a novel target for the disruption of multiple signaling cascades. *Curr. Cancer Drug Tar.* 2007, 7, 369-388.
Chiosis et al., Synthesis of Hsp90 Dimerization Modulators. *Biorg. Med. Chem. Lett*, vol. 16, 2006, pp. 3529-3532.
Conde, R.; Belak, Z. R.; Nair, M.; O'Carroll, R. F.; Ovsenek, N. Modulation of Hsfl activity by novobiocin and geldanamycin. Biochem. *Cell Biol.* 2009, 87, 845-851.

(Continued)

*Primary Examiner* — San-Ming Hui
*Assistant Examiner* — Jeanmarie Calvillo Y
(74) *Attorney, Agent, or Firm* — Merchant & Gould PC

(57) ABSTRACT

The present disclosure provides a series of compounds which exhibit isoform selective inhibition of GRP94, a homologue of Hsp90 that is localized to the endoplasmic recticulum. Through GRP94 inhibition, these compounds are likely to manifest anti-cancer, anti-inflammatory, anti-metastasis, and immunosuppressive activities, as well as utility in the treatment of neurodegenerative diseases, and diabetes.

13 Claims, 15 Drawing Sheets

(56) References Cited

OTHER PUBLICATIONS da Rocha Dias, S.; Friedlos, F.; Light, Y.; Springer, C.; Workman, P.; Marais, R. Activated B-RAF Is an Hsp90 Client Protein That Is Targeted by the Anticancer Drug 17-Allylamino-17-Demethoxygeldanamycin. *Cancer Res.* 2005, 65, 10686-10691.

Duerfeldt et al., "Design, Synthesis, and Biological Evaluation of Conformationally Constrained CIS-Amide Hsp90 Inhibitors." *Org. Lett.*, vol. 11, No. 11, Jun. 2009, pp. 2353-2356.

Grbovic, O. M.; Basso, A. D.; Sawai, A.; Ye, Q.; Friedlander, P.; Solit, D.; Rosen, N. V600E B-Raf requires the Hsp90 chaperone for stability and is degraded in response to Hsp90 inhibitors. *P. Natl. Acad. Sci.* 2006, 103, 57-62.

Hadden, M. K.; Blagg, B. S. J. Synthesis and Evaluation of Radamide Analogues, A Chimera of Radicicol and Geldanamycin. *J. Org. Chem.* 2009, 74, 4697-4704.

Immormino, R. M.; Dollins, D. E.; Shaffer, P. L.; Soldano, K. L.; Walker, M. A.; Gewirth, D. T. Ligand-induced conformational shift in the N-terminal domain of GRP94, an Hsp90 chaperone. *J. Biol. Chem.* 2004, 279, 46162-46171.

Immormino, R. M.; Metzger Iv, L. E.; Reardon, P. N.; Dollins, D. E.; Blagg, B. S. J.; Gewirth, D. T. Different Poses for Ligand and Chaperone in Inhibitor-Bound Hsp90 and GRP94: Implications for Paralog-Specific Drug Design. *J. Mol. Biol.* 2009, 388, 1033-1042.

Isaacs, J. S.; Xu, W. S.; Neckers, L. Heat shock protein as a molecular target for cancer therapeutics. *Cancer Cell* 2003, 3, 213-217.

Li, Y.; Schwartz, S. J.; Sun, D. New developments in Hsp90 inhibitors as anti-cancer therapeutics: mechanisms, clinical perspective and more potential. *Drug Resist. Update* 2009, 12, 17-27.

Mao et al., Targeted Mutation of the Mouse Grp94 Gene Disrupts Development and Perturbs Endoplasmic Reticulum Stress Signaling, *PLoS One*, May 26, 2010; 5(5):e10852.

Neckers, L.; Hsp90 inhibitors as novel cancer chemotherapeutic agents. *Trends Mol. Med.* 2002, 8, S55-S61.

Ostrovsky, O.; Ahmed, N. T.; Argon, Y. The Chaperone Activity of GRP94 Toward Insulin-like Growth Factor II Is Necessary for the Stress Response to Serum Deprivation. *Mol. Biol. Cell* 2009, 20, 1855-1864.

Ostrovsky, O.; Eletto, D.; Makarewich, C.; Barton, E. R.; Argon, Y. Glucose regulated protein 94 is required for muscle differentiation through its control of the autocrine production of insulin-like growth factors. *BBA—Mol. Cell Res.* 2010, 1803. 333-341.

Peterson, L. B.; Blagg, B. S. J.; To fold or not to fold: Modulation and consequences of Hsp90 inhibition. *Future Med. Chem.* 2009, 1.

Roe et al., "Structural Basis for Inhibition of the Hsp90 Molecular Chaperone by the Antitumor Antibiotics Radicicol and Geldanamycin," *J. Med. Chem.*, vol. 42, 1999, pp. 260-266.

Soldano, K. L.; Jivan, A.; Nicchitta, C. V.; Gewirth, D. T. Structure of the N-terminal domain of GRP94. Basis for ligand specificity and regulation. *J. Biol. Chem.* 2003, 278, 48330-48338.

Taldone, T.; Gozman, A.; Maharaj, R.; Chiosis, G. Targeting Hsp90: small-molecule inhibitors and their clinical development. *Curr. Opin. Pharmacol.* 2008, 8, 370-374.

Vogen, S.; Gidalevitz, T.; Biswas, C.; Simen, B. B.; Stein, E.; Gulmen, F.; Argon, Y. Radicicol-sensitive Peptide Binding to the N-terminal Portion of GRP94. *J. Biol. Chem.* 2002, 277, 40742-40750.

Workman, P.; Combinatorial attack on multistep oncogenesis by inhibiting the Hsp90 molecular chaperone. *Cancer Lett.* 2004, 206, 149-157.

Workman, P.; Billy, E. d. Putting the heat on cancer. *Nat. Med.* 2007, 13, 1415-1417.

Workman, P.; Burrows, F.; Neckers, L.; Rosen, N. Drugging the cancer chaperone Hsp90: Combinatorial therapeutic exploitation of oncogene addiction and tumor stress. *Ann. NY Acad. Sci.* 2007, 1113, 202-216.

International Search Report and Written Opinion mailed Jul. 13, 2012 re PCT/US2012/32538.

Ostrovsky, O.; Eletto, D.; Makarewich, C.; Barton, E. R.; Argon, Y. Glucose regulated protein 94 is required for muscle differentiation through its control of the autocrine production of insulin-like growth factors. *BBA—Mol. Cell Res.* 2010, 1803, 333-341.

* cited by examiner

GRP94 INHIBITORS

CROSS-REFERENCES TO RELATED APPLICATIONS

This application claims the benefit of priority to U.S. Provisional Application Ser. No. 61/473,343, filed Apr. 8, 2011, which is hereby incorporated herein by reference.

STATEMENT REGARDING FEDERALLY SPONSORED RESEARCH OR DEVELOPMENT

This invention was made with Government support under National Institutes of Health (NIH) Grant Nos. AG18001, GM077480, DK053058 and CA109265, awarded by the National Cancer Institute. The Government has certain rights in this invention.

BACKGROUND OF THE INVENTION

1. Field of the Invention

The present disclosure provides a series of compounds which exhibit isoform selective inhibition of Glucose-related protein 94 (Grp94), a homologue of the cytoplasmic Heat shock protein 90 (Hsp90) that is localized to the endoplasmic recticulum. Through Grp94 inhibition, these compounds are likely to manifest anti-cancer, anti-inflammatory, anti-metastasis, and immunosuppressive activities, in addition to exhibiting properties beneficial to the management of neurodegenerative diseases, and diabetes.

2. Description of the Related Art

Hsp90 chaperones contain an N-terminal ATP binding site that has been effectively targeted by competitive inhibitors. Although Hsp90 inhibition has garnered tremendous attention in drug development for multiple disease states and numerous companies are in late-stage clinical development, no isoform selective inhibitor has yet been discovered. Despite the development of a number of Hsp90 inhibitors, none to date have been designed to bind specifically to just one of the four mammalian Hsp90 paralogs, which are cytoplasmic Hsp90α and β, ER Grp94, and mitochondrial Trap-1. Multiple detriments are associated with current Hsp90 inhibitors, which in many cases result from the non-selective inhibition of all four Hsp90 isoforms. To date, all known disruptors of Hsp90 are pan-inhibitors, that is, they inhibit all isoforms.

Although Hsp90 represents a promising therapeutic target for the treatment of cancer and other diseases, unfortunately, results from clinical trials have been disappointing as off-target effects and toxicities have been observed. These detriments may be a consequence of pan-Hsp90 inhibition, as all clinically evaluated Hsp90 inhibitors simultaneously disrupt all four human Hsp90 isoforms.

Rationale to develop isoform selective inhibitors is highly desirable and to the best of our knowledge has not been reported.

Grp94 is an isoform of heat shock protein 90 kDa (Hsp90) localized to the endoplasmic reticulum. Grp94 is responsible for the maintenance of cell adhesion proteins and the trafficking of numerous receptors to the cell membrane. Through inhibition of Grp94, this process is halted. GRP94 is present at elevated levels in numerous cancers and several GRP94 client proteins have been recognized. For example, see McLaughlin and Vandenbroeck. *Brit. J. Pharmacol.* 2011, 162, 328-345, which is incorporated herein by reference.

The anti-cancer effects of Hsp90 inhibition have driven the development of potent antagonists. Among the first Hsp90 inhibitors to be identified were the natural product ansamycin antibiotics Geldanamycin (Gdm) and Radicicol (Rdc). The scaffolds of these ansamycins and the natural ligand ATP were exploited for inhibitor design. Gdm has also been used as a tool to better understand the quaternary structure and regulatory roles of GRP94. Chu et al., 2006, Protein Sci., 15:1260-1269; Chiosis et al., Biorg. Med. Chem. Lett 2006; 16:3529-32. A chimeric Hsp90 inhibitor, Radamide, was previously developed from the structures of Gdm and Rdc. Clevenger and Blagg, Org. Lett. 2004; 6: 4459-62. Various radamide analogs have been previously described. See for example, Hadden and Blagg, 2009, J. Org. Chem., 74(3): 4697-4704, which is incorporated herein by reference.

To understand differences in how pan-Hsp90 inhibitors interact with the Grp94 and Hsp90 ATP binding site, Immormino et al., 2009 solved the co-crystal structures of the radicicol-geldanamycin chimera Radamide bound both to yeast Hsp82 and Grp94. The Radamide co-crystal structures revealed distinct ligand poses that exploit differences in the ATP binding sites of Hsp90 and GRP94. Direct binding assays with Radamide revealed disparate affinities for the two Hsp90 paralogs. Taken together, these results demonstrate that Grp94 and Hsp90, though very similar, interact with a selection of Hsp90 inhibitors in different manners. See Immormino et al., 2009, J. Mol. Biol., 388(5):1033-1042, which is incorporated herein by reference.

The discovery of more selective Grp94 selective inhibitors is highly desirable and is predicted to have implications in both drug development as well as the treatment of multiple disease states including cancer, inflammation, neurodegeneration and diabetes. Until this disclosure, the only methods for selective Grp94 disruption reported have been through gene silencing and siRNA procedures. It was previously unknown whether a Grp94 selective inhibitor could be constructed.

The disclosure provides rationale and design of scaffolds that exhibit selective Grp94 inhibition. For example, the discovery of the first isoform selective inhibitors of Grp94, some of which exhibit greater than 100-fold selectivity for Grp94 over cytosolic Hsp90, is herein disclosed.

SUMMARY OF THE INVENTION

The present invention is directed to novel compounds useful as Grp94 isoform selective Hsp90 inhibitors, and in particular as anti-cancer, anti-inflammatory and neuroprotective agents.

In an embodiment, the disclosure provides Grp94 inhibitor compounds. In another aspect, the compounds are selective for Grp94 inhibition over that of other Hsp90 isoforms. In embodiments, the disclosure provides a Grp94 inhibitor compound, or pharmaceutically acceptable salt of Formula (I):

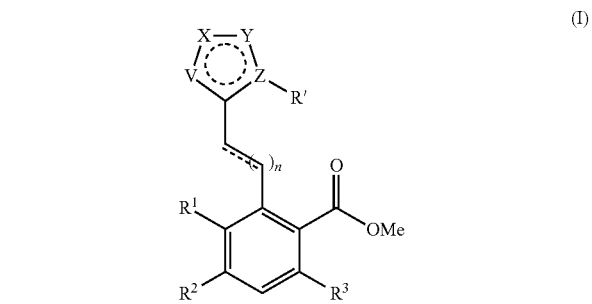

wherein V, X, and Y are each independently selected from CH, NH or N; Z is selected from C or N; $R^1$ is selected from the group consisting of H, F, Cl, Br, I, methyl, ethyl, n-propyl, isopropyl, butyl, phenyl, and benzyl; $R^2$ is selected from the group consisting of H, OH, SH, and $NH_2$; $R^3$ is selected from the group consisting of H, OH, SH, and $NH_2$; R' is selected from the group consisting of

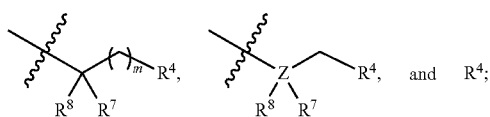

$R^4$ is selected from the group consisting of

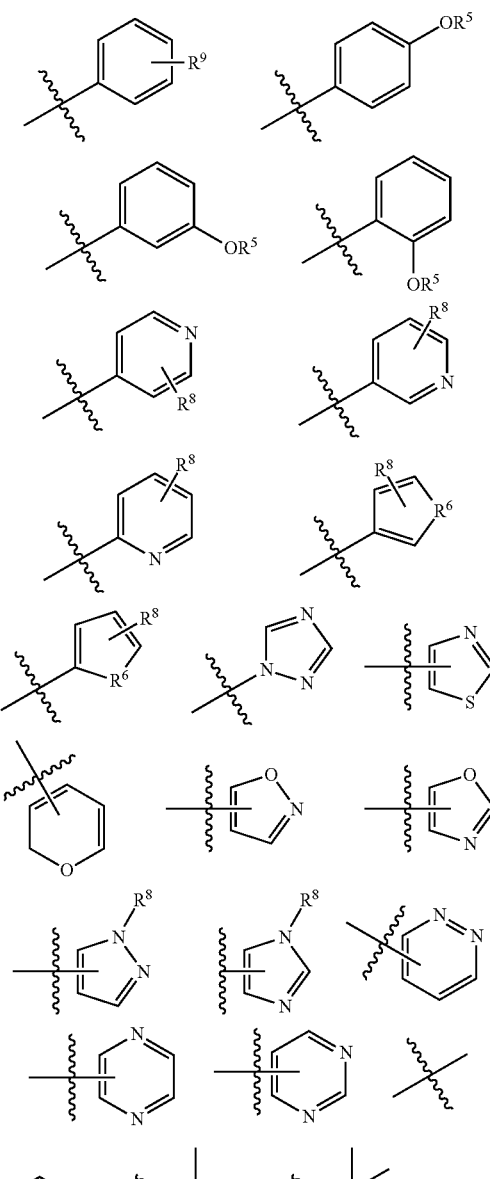

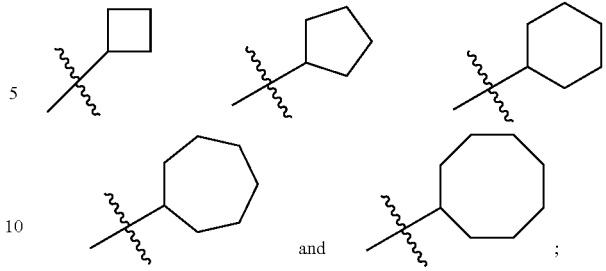

$R^5$ is selected from the group consisting of methyl, ethyl, propyl, isopropyl, butyl, isobutyl, sec-butyl, and tert-butyl;

$R^6$ is selected from the group consisting of O, S, NH, and $CH_2$;

$R^7$ is selected from the group consisting of H, and methyl; and $R^8$ is selected from the group consisting of H, methyl, ethyl, propyl, isopropyl, butyl, isobutyl, sec-butyl, and tert-butyl;

$R^9$ is selected from the group consisting of H, methyl, ethyl, propyl, iso-propyl, butyl, sec-butyl, tert-butyl, halogen, OH, $NH_2$, $NR^{10}H$, $N(R^{10})_2$, and $NCOR^{10}$;

$R^{10}$ is selected from the group consisting of methyl, ethyl, propyl, isopropyl, butyl, sec-butyl, and tert-butyl;

n is selected from 0, 1, 2, or 3, wherein when n is 1, --- represents a single or a double bond, wherein the double bond is in the cis or trans configuration, and when n is 0, 2 or 3, --- represents a single bond; and m is selected from 0, 1, 2, 3 or 4.

In one aspect, the disclosure provides a compound or pharmaceutically acceptable salt of the formula:

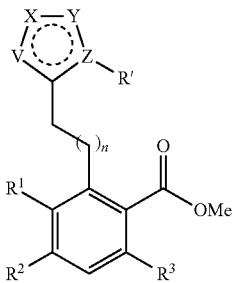

wherein V is N; and Z is N.
In one aspect, R' is

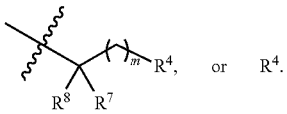

In a preferred aspect, V is N; X is CH; Y is CH; and Z is N.
In another preferred aspect, R' is F, Cl, Br, or I. In a specific preferred aspect, $R^1$ is Cl; $R^2$ is OH; and $R^3$ is OH.

In one aspect, $R^4$ is selected from the group consisting of
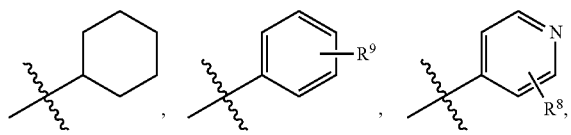
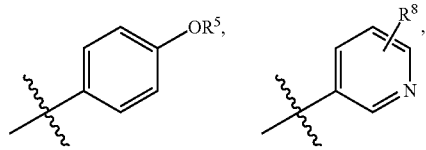
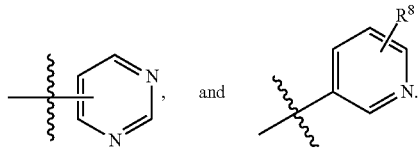
In another specific aspect, the compound of Formula I is selected from the group consisting of
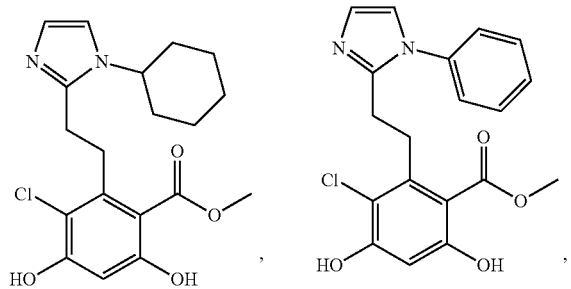
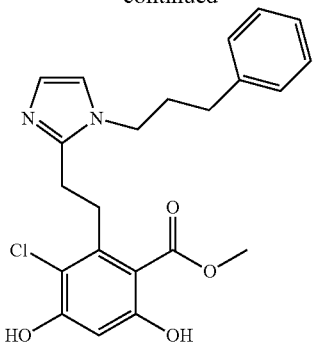
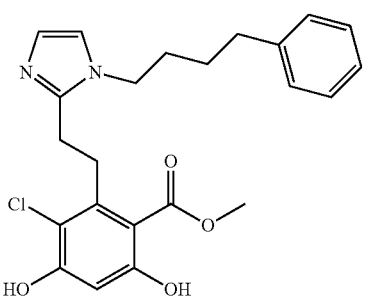
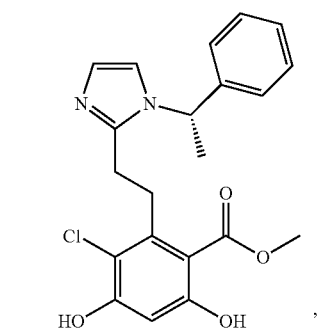
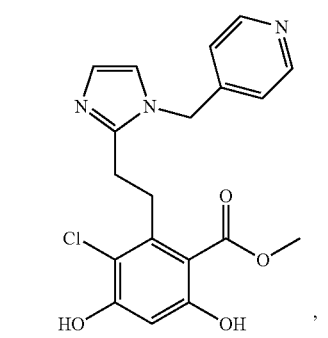
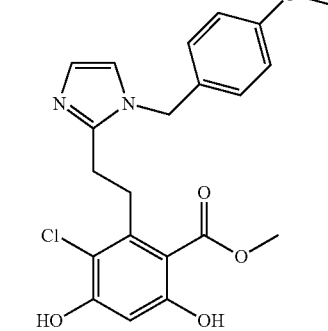

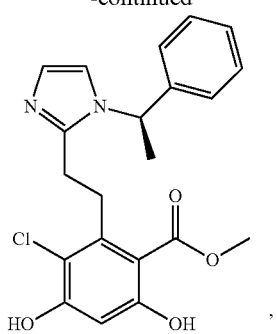,

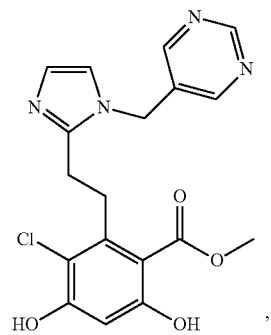,

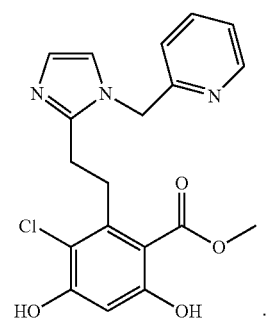,

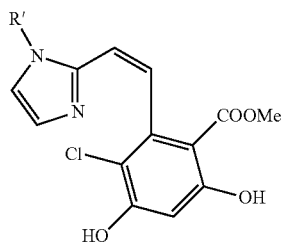

wherein R' is as defined for Formula I, above.

In another aspect, the disclosure provides a pharmaceutical composition comprising a compound or salt according to Formula I, and a pharmaceutically acceptable carrier.

In another aspect, the disclosure provides a method for treating or preventing a GRP94 related disorder in a patient in need thereof, wherein the treating or preventing comprises administering a therapeutically effective amount of a pharmaceutical composition comprising a compound or salt according to claim 1, and a pharmaceutically acceptable carrier or excipient to the patient. In another aspect, the GRP94 related disorder is selected from the group consisting of cancer, metastasis, an inflammatory disorder, a neurodegenerative disorder, and diabetes.

In another embodiment, the disclosure provides a GRP94 selective compound of Formula IV

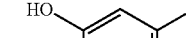

wherein the linker is selected from

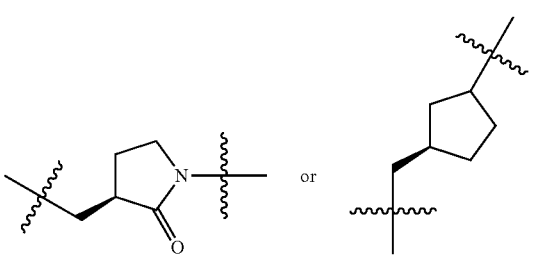

In another aspect, the compound of Formula I is of Formula VI

In another embodiment, the disclosure provides a GRP selective compound or pharmaceutically acceptable salt of Formula V:

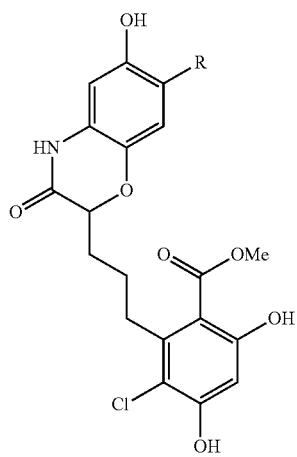

(V)

wherein R is X'—R⁴; and X' is selected from O, S, SO, SO₂, NH, and NR¹⁰;

R⁴ is selected from the group consisting of

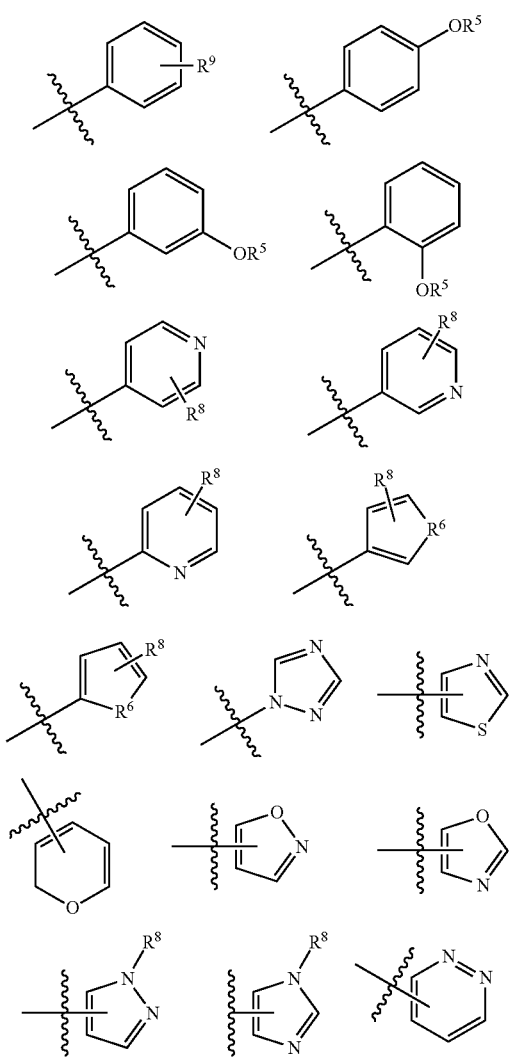

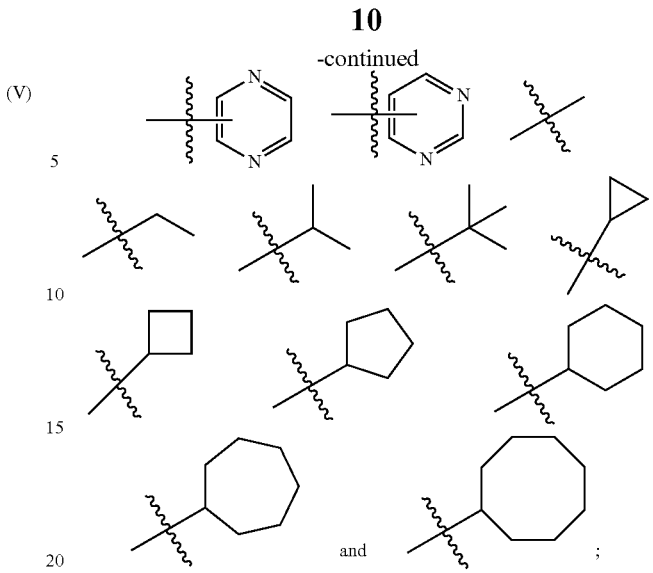

$R^5$ is selected from the group consisting of methyl, ethyl, propyl, isopropyl, butyl, isobutyl, sec-butyl, and tert-butyl; $R^6$ is selected from the group consisting of O, S, NH, and $CH_2$; $R^8$ is selected from the group consisting of H, methyl, ethyl, propyl, isopropyl, butyl, isobutyl, sec-butyl, and tert-butyl; $R^9$ is selected from the group consisting of H, methyl, ethyl, propyl, iso-propyl, butyl, sec-butyl, tert-butyl, halogen; and $R^{10}$ is selected from the group consisting of methyl, ethyl, propyl, isopropyl, butyl, sec-butyl, and tert-butyl; m is selected from 0, 1, 2, 3 or 4.

In a particular aspect, in the compound of Formula V, R is selected from the group consisting of

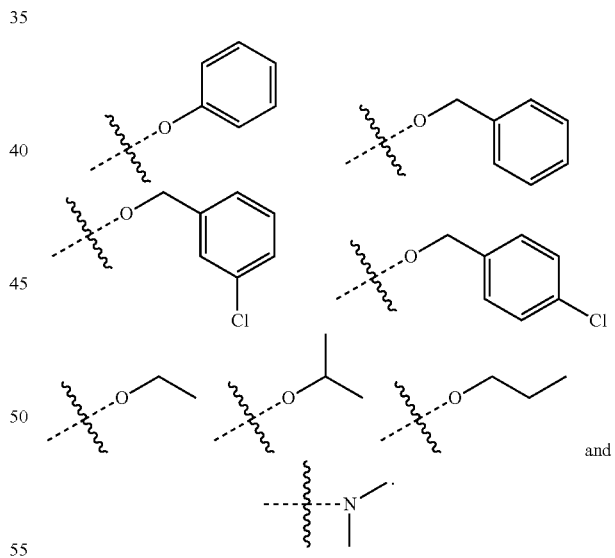

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier.

DETAILED DESCRIPTION

Figure 1:
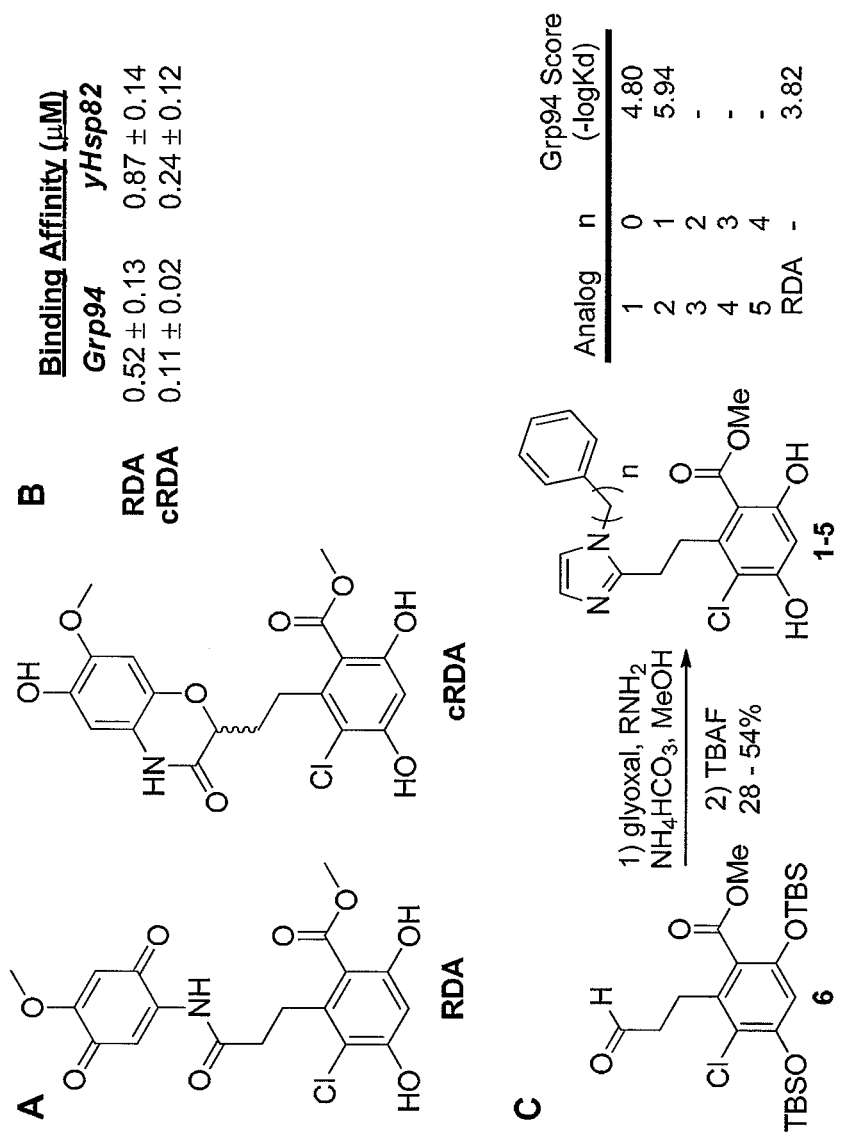
FIG. 1 shows (A) the structures of RDA and cRDA, (B) the binding affinity data for RDA, and cRDA as determined via fluorescent quenching and (C) synthetic conditions to produce the 1,2-imidazole analogs 1-5, including BnIm, 2.

The 90 kDa heat shock proteins ("Hsp90") belong to a family of chaperones that regulate intracellular functions and are required for the refolding of denatured proteins following heat shock, as well as the conformational maturation of a large number of key proteins involved in cellular processes. The Hsp90 family of chaperones is comprised of four different isoforms. Hsp90α (inducible/major form) and Hsp90β (constitutive/minor form) are found predominately in the cytosol, the 94-kDa glucose-regulated protein ("GRP94") is localized to the endoplasmic reticulum, and Hsp75/tumour necrosis factor receptor associated protein 1 ("TRAP-1") resides mainly in the mitochondrial matrix. These Hsp90s bind to client proteins in the presence of cochaperones, immunophilins, and partner proteins to make the multiprotein complex responsible for conformational maturation of newly formed nascent peptides into biologically active three-dimensional structures.

Hsp90 is an ATP-dependent protein with an ATP binding site in the N-terminal region of the active homodimer. Disruption of the ATPase activity of Hsp90 results in the destabilization of multiprotein complexes and subsequent ubiquitination of the client protein, which undergoes proteasome-mediated hydrolysis. More specifically, in an ATP-dependent fashion, Hsp70 binds to newly synthesized proteins cotranslationally and/or posttranslationally to stabilize the nascent peptide by preventing aggregation. Stabilization of the Hsp70/polypeptide binary complex is dependent upon the binding of Hsp70 interacting protein ("HIP"), which occurs after Hsp70 binds to the newly formed peptide. Hsp70-Hsp90 organizing protein ("HOP") contains highly conserved tetratricopeptide repeats ("TPRs") that are recognized by both Hsp70 and Hsp90, promoting the union of Hsp70/HIP and Hsp90, which results in a heteroprotein complex. In the case of telomerase and steroid hormone receptors, the client protein is transferred from the Hsp70 system to the Hsp90 homodimer with concomitant release of Hsp70, HIP, and HOP. Upon binding of ATP and an immunophilin with cis/trans peptidyl prolyl-isomerase activity (FKBP51, FKBP52, or CyPA), the ensemble folds the client protein into its three-dimensional structure. In a subsequent event, p23 binds Hsp90 near the N-terminal region promoting the hydrolysis of ATP and release of the folded protein, Hsp90 partner proteins, and ADP.

Hsp90 contains two nucleotide-binding sites: the N-terminal ATP binding site is the region to which geldanamycin ("GDA"), 17-(allylamino)-17-demethoxygeldanamycin ("17-AAG"), herbimycin A ("HB"), and radicicol bind (see Roe et al., Structural Basis for Inhibition of the Hsp90 Molecular Chaperone by the Antitumor Antibiotics Radicicol and Geldanamycin, *J. Med. Chem.* 1999, 42, 260-266) and the C-terminus, which was recently shown to bind novobiocin (see Marcu et al., The Heat Shock Protein 90 Antagonist Novobiocin Interacts with a Previously Unrecognized ATP-binding Domain in the Carboxy Terminis of the Chaperone, *J. Biol. Chem.* 2000, 276, 37181).

Examples of proteins dependent upon Hsp90 for conformational maturation include oncogenic and cellular Src kinases (v-Src, Hck, Lck), Raf, p185, mutant p53 (not normal p53), telomerase, steroid hormone receptors, polo-like kinase ("PLK"), protein kinase B ("AKT"), death domain kinase ("RIP"), MET kinase, focal adhesion kinase ("FAK"), aryl hydrocarbon receptor, RNA-dependent protein kinase ("PKR"), nitric oxide synthase ("NOS"), centrosomal proteins, PI3 kinases, androgen receptor ("AR"), matrix metalloproteinase-2 ("MMP2") and others. In addition, other proteins, such as cyclin dependent kinase 4 ("CDK4"), cyclin dependent kinase 6 ("CDK6"), estrogen receptor, human epidermal growth factor receptor 2 ("Her-2" or "erbB2") are thought to be client proteins of Hsp90. Of these Hsp90 client proteins, Raf, PLK, RIP, AKT, FAK, telomerase, HER-2, and MET kinase are directly associated with the six hallmarks of cancer: (1) self-sufficiency in growth signals; (2) insensitivity to antigrowth signals; (3) evasion of apoptosis; (4) unlimited replication potential; (5) sustained angiogenesis; and (6) tissue invasion/metastasis. Consequently, Hsp90 is a target for the development of cancer therapeutics because multiple signaling pathways can be simultaneously inhibited by disruption of the Hsp90 protein folding machinery.

Glucose-regulated protein 94 (GRP94) is one of the most abundant endoplasmic reticulum (ER) resident proteins and is the ER counterpart of the cytoplasmic heat shock protein 90 (HSP90). GRP94, a component of the GRP78 chaperone system in protein processing, has pro-survival properties with implicated function in cancer progression and autoimmune disease. Previous studies on the loss of GRP94 function showed that it is required for embryonic development, regulation of toll-like receptors and innate immunity of macrophages. Mao et al., PLoS One, 2010 May 26; 5(5):e10852.

Using a structure-based approach, an inhibitor of Grp94, the ER-resident Hsp90 was designed. The effects of compound (2) on several Grp94 and Hsp90α/β (cytosolic isoforms) clients were investigated. Compound 2 prevented intracellular trafficking of the Toll receptor, inhibited the secretion of IGF-II, affected the conformation of Grp94, and suppressed *Drosophila* larval growth, all Grp94-dependent processes. In contrast, compound 2 had no effect on cell viability or cytosolic Hsp90α/β client proteins at similar concentrations.

In one embodiment, the selective GRP94 inhibitor compounds of the present disclosure will be useful in treating a GRP94 related disorder. GRP94 related disorders include cancer, metastasis, inflammatory disorders, neurodegenerative disorders, autoimmune disorders and diabetes.

GRP94 involvement is implicated in a number of cancers. For example, overexpression of GRP78 and GRP94 are markers for aggressive behavior and poor prognosis in gastric carcinomas. Zheng et al., 2008, Human Pathology, 39(7): 1042-1049. GRP78 protein expression is significantly higher in prostate cancer than benign prostatic tissue. Daneshmand et al., 2007, Human Pathol. 38(10):1547-52. GRP94 and GRP78 overexpressed in canine prostate and bladder carcinomas compared to normal bladder and prostate tissue. LeRoy et al., 2007, Vet. Comp. Oncol., 5(2):119-130. Silencing of GRP expression promotes apoptosis in pancreatic cancer cells. Pan et al., 2009, Int. J. Oncol., 35(4): 823-8.

In one aspect, the GRP94 inhibitors of the present disclosure will be useful as anticancer agents useful in treating a GRP94 related disorder. In one aspect, the cancer is selected from the group consisting of breast cancer, colon cancer, pancreatic cancer, or prostate cancer. In another aspect, the cancer is selected from the group consisting of breast cancer, ovarian cancer, colon cancer, head and neck cancer, lung cancer, gynecological cancers, brain cancer, germ cell cancer, urothelial cancer, esophageal cancer, prostate cancer, bladder cancer, or pancreatic cancer. A patient in need of cancer treatment is administered a therapeutically effective amount of the compounds of the present invention.

In another aspect, the GRP94 selective inhibitors of the present disclosure will be useful as neuroprotective agents. Neurodegenerative diseases are often associated with dysfunction in protein quality control. The endoplasmic reticulum (ER), a key site for protein synthesis, senses stressful conditions by activating the unfolded protein response (UPR). Wang et al., 2010 reported the creation of a novel mouse model in which GRP78/BiP, a major ER chaperone and master regulator of $UPR_1$ is specifically eliminated in Purkinje cells (PCs). GRP78-depleted PCs activate UPR including the induction of GRP94, PDI, CHOP and GADD34, feedback suppression of eIF2alpha phosphorylation and apoptotic cell death. Wang et al., 2010 March; 17(3): 488-98.

In one aspect, the GRP94 inhibitors of the present disclosure will be useful in treating a GRP94 related neurodegenerative disorder. In one aspect, the GRP94 related disorder is a neurodegenerative disorder. (Peyrat et al., Inhibitors of the heat shock protein 90: from cancer clinical trials to neurodegenerative diseases. Atlas Genet Cytogenet Oncol Haematol. April 2010). In one aspect the GRP94 related neurodegenerative disorders include transmissible spongiform encephalopathies (Hetz and Soto, Curr Mol Med 2006 February; 6(1): 37-43), prion-related disorders (Torres et al., Commun Integr Biol 2011 May-June; 4(3): 258-261), Alzheimer's Disease (Luo et al., BMC Neurosci. 2008 Dec. 3; 9 Suppl 2:S7. (REVIEW); Luo et al 2007, Proc Natl Acad Sci USA. 2007 May 29; 104(22):9511-6. Epub 2007 May 21), Lewy Body Dementia, Parkinson's Disease, Huntington's disease, and Amyotrophic lateral sclerosis. The Prion-related disorders (PrDs) can be categorized as familial, sporadic and infectious. PrDs can be selected from Creutzfeld-Jakob disease, variant Creutzfeld-Jakob disease, familial Creutzfeld-Jakob disease, iatrogenic Creutzfeld-Jakob disease, fatal familial insomnia and Gerstmann-Straussler-Scheinker syndrome. See, e.g., Belay, Annu Rev Microbiol, 1999, 53:283-314. In another particular aspect, the neurodegenerative disorder is a prion-related disorder.

The accumulation of protein aggregates within or outside neurons is a common characteristic of the two most common age-related neurodegenerative diseases, Alzheimer's disease, with plaques enriched in β-amyloid peptides ("Aβ") and neurofibrillary tangles ("NFTs") containing hyperphosphorylated Tau protein, and Parkinson's disease ("PD") with Lewy bodies composed primarily of fibrillar α-synuclein. However, even less frequent but equally debilitating nervous system diseases such as Huntington's disease, amyotrophic lateral sclerosis ("ALS"), prion diseases, and the tauopathies also share the characteristic of aggregated protein deposits. A growing body of evidence now indicates that strategies that promote either refolding or degradation of hyperphosphorylated Tau enhance cell survival in the presence of over-expressed Tau or mutant human Tau. See, e.g., Shimura et al., Binding of Tau to heat shock protein 27 leads to decreased concentration of hyperphosphorylated tau and enhanced cell survival, *J. Biol. Chem.*, 2004, 279:17957-17962; Dou et al., Chaperones increase association of Tau protein with microtubules, *Proc. Natl. Acad. Sci. USA*, 2003, 100:721-726; Kosik & Shimura, Phosphorylated tau and the neurodegenerative foldopathies, *Biochim. Biophys. Acta.*, 2005, 1739: 298-310; Shimura et al., CHIP-Hsc70 complex ubiquitinates phosphorylated tau and enhances cell survival, *J. Biol. Chem.*, 2005 279:4869-4876. Such observations suggest that the cellular machinery needed for removal of misfolded proteins may be compromised in neurodegenerative diseases.

More specifically, the interaction of Hsp90 isoforms with cochaperones that regulate cell-specific responses to stress has led to the identification of Hsp90 and the cochaperones Hsp70 and CHIP (carboxy-terminus of the Hsp70-interacting protein) as strong candidates in determining the fate of neuronal protein aggregates. This has been most clearly demonstrated in the case of the hyperphosphorylated Tau protein in NFTs in Alzheimer's disease and the "tauopathies" due to mutations in the tau gene. Low concentrations of Hsp90 inhibitors appear to up-regulate expression of Hsp90 and co-chaperones that decrease aggregated Tau and increase neuronal survival. However, most of the known Hsp90 inhibitors are toxic to many cell types, limiting their potential for chronic use to delay the progression of neurodegenerative diseases. Thus, there remains a need to develop other Hsp90 inhibitors as useful neuroprotective agents. In a particular aspect, the GRP related neurodegenerative disorder is a beta amyloid disorder, such as Alzheimer's Disease or Lewy body dementia.

Cellular stresses such as elevated temperature, abnormal pH, oxidative stress, and malignancy result in the denaturation of native proteins as well as the overexpression of molecular chaperones to refold these structures or target them for degradation via the ubiquitin-proteasome pathway. Upon exposure to these stresses, Hsp90 and Hsp70 levels are increased to assist in the renaturation process. The expression of these heat shock proteins is tightly regulated by the transcription factor heat shock factor 1 ("HSF-1"). Under normal conditions, Hsp90 forms a stable complex with HSF-1 and prevents the transcriptional activation of the heat shock response. Cellular stressors result in destabilization of Hsp90/HSF-1, the subsequent trimerization and phosphorylation of HSF-1, and its translocation to the nucleus, where it induces Hsp expression. Another key protein in the Hsp90 heteroprotein complex is the co-chaperone CHIP (carboxyl terminus of the Hsc70-interacting protein). CHIP binds Hsp70 through its tetratricopeptide repeat ("TPR") domain and also possesses intrinsic ubiquitin ligase activity, suggesting a direct link between the chaperone and the ubiquitin-proteasome pathway which may modulate the cellular equilibrium of protein folding and degradation.

More specifically, the interaction of Hsp90 with cochaperones that regulate cell-specific responses to stress has led to the identification of Hsp90 and the cochaperones Hsp70 and CHIP (carboxy-terminus of the Hsp70-interacting protein) as strong candidates in determining the fate of neuronal protein aggregates. This has been most clearly demonstrated in the case of the hyperphosphorylated Tau protein in NFTs in Alzheimer's disease and the "tauopathies" due to mutations in the Tau gene. Low concentrations of Hsp90 inhibitors appear to up-regulate expression of Hsp90 and co-chaperones that decrease aggregated Tau and increase neuronal survival. However, most of the known Hsp90 inhibitors are toxic to many cell types, limiting their potential for chronic use to delay the progression of neurodegenerative disorders. Thus, there remains a need to develop other Hsp90 inhibitors as useful neuroprotective agents.

Further, the heat shock response suppresses gene expression for nitric oxide synthase, cytokines, and chemokines, all of which have been implicated in autoimmune disorders, such as multiple sclerosis. The administration of Hsp90 inhibitors thus should lead to a heat shock response due to the dissociation of HSF-1 from Hsp90. Thus, the present invention contemplates that the novel compounds of the present invention are useful in the treatment of autoimmune disorders.

In another aspect, GRP94 selective inhibitors of the present disclosure will be useful in the treatment of various autoimmune disorders. Experimental allergic encephalomyelitis (EAE) is an autoimmune disease characterized by demyelination and inflammatory infiltrates in the CNS, and it is an animal model of multiple sclerosis. Piperonyl butoxide (PBO) suppresses disease in EAE mice, and it exhibits a dual effect on cytochrome P450s that manifests in a transient inhibitory phase followed by induction. In order to identify the expression of proteins associated with EAE, a proteomic screening was performed on hindbrain microsomes from control+vehicle, control+PBO, EAE+vehicle, and EAE+PBO female mice. Glucose regulated protein 94 (Grp94) and coagulation factor VIII were among the proteins identified in EAE+vehicle and EAE+PBO mice. Since Grp94 (also known as Gp96) can partake in antigen presentation and induction of proinflammatory cytokine expression, its presence in these cells suggests that it may play a role in the pathogenesis of EAE. See Duzhak et al., 2003, Analysis of protein induction in the CNS of SJL mice with experimental allergic encephalitis by proteomic screening and immunohistochemistry, Cell Mol. Biol., July; 49(5):723-32.

It is also contemplated that the GRP94 selective inhibitors of the present disclosure may be useful in the treatment of other autoimmune disorders such as rheumatoid arthritis (RA) and systematic lupus erythematosus (SLE). Rheumatoid arthritis is a chronic disease that leads to inflammation of the joints and surrounding tissue. It can also affect other organs. Weber et al., 2010, investigated the presence of autoantibodies against mammalian chaperones of the endoplasmic reticulum (ER) in patients with rheumatoid arthritis (RA) and other immune-mediated diseases. In patients with RA and systematic lupus erythematosus (SLE), autoantibody titres against BiP, Grp94 and calnexin were significantly higher than those in healthy controls. These autoantibodies were detectable in patients with early RA and titres remained stable for at least 6-12 months. Weber et al., Antibodies to the endoplasmic reticulum-resident chaperones calnexin, BiP and Grp94 in patients with rheumatoid arthritis and systemic lupus erythematosus. Rheumatology, 2010 December; 49(12):2255-63. Epub 2010 Aug. 17. Recently, Grp94, the 96-kDa heat shock glycoprotein (gp96), also known as Gp96, has been implicated in antigen presentation, tumor immunity and activation of innate immunity and participates in the folding and assembly of many secretary and membrane proteins, and is essential for the cell-surface expression of TLRs including TLR2 and TLR4. Gp96 has been reported to activate professional antigen-presenting cells, such as dendritic cells and macrophages as well as neutrophils and monocytes, promoting the induction of IL-1β and TNFα. See Huang et al., 2009, heat shock protein 96 is elevated in rheumatoid arthritis and activates macrophages primarily via TLR2 signaling, J. Immunol. 182(8):4965, incorporated herein by reference. Huang et al., 2009. demonstrated immunohistochemistry, immunoblot and ELISA that gp96 is highly expressed in the RA joint, while other HSPs that might serve as endogenous TLR ligands were less readily detected in RA synovial fluid. Gp96 induced the expression of TLR2 and cytokines in control and RA synovial fluid macrophages.

It is also contemplated that the GRP94 selective inhibitors of the present disclosure will be useful in the treatment of asthma. Asthma is a common chronic inflammatory disorder of the airways which causes attacks of wheezing, shortness of breath, chest tightness, and coughing. Bradykinin is a major mediator of swelling in C1 inhibitor deficiency as well as the angioedema seen with ACE inhibitors and may contribute to bronchial hyperreactivity in asthma. Formation of bradykinin occurs in the fluid phase and along cell surfaces requiring interaction of factor XII, prekallikrein, and high M(r) kininogen (HK). Heat shock protein 90 (Hsp90) was identified as the protein responsible for zinc-dependent prekallikrein activation in the presence of HK. Zinc-dependent activation of the prekallikrein-HK complex also depended on addition of either alpha and beta isoforms of Hsp90 and the activation on endothelial cells was inhibited on addition of polyclonal Ab to Hsp90 in a dose-dependent manner. Joseph et al., 2002, Heat shock protein 90 catalyzes activation of the prekallikrein-kininogen complex in the absence of factor XII. Proc. Nat'l. Acad. Sci. USA, 99(2):896-900. It is contemplated that the GRP94 paralog may also play a role in the etiology of asthma.

It is also contemplated that the GRP94 selective inhibitors of the present disclosure will be useful in the treatment of diabetes. In mammalian cells, conditions of ER stress lead to the initiation of the unfolded protein response (UPR), which functions to return cells to homeostasis by 1) the general inhibition of protein translation and 2) the specific induction of ER resident chaperone expression, including Grp78, Grp94, and calreticulin (CALR). There is increasing experimental evidence in support of a direct and causative role for ER stress in the development and/or progression of diabetes mellitus, particularly with respect to pancreatic B-cell death and insulin resistance. In recent years, ER stress has been linked to the development of complications associated with diabetes mellitus, including nephropathy, retinopathy, and cardiovascular complications. See, e.g., Sage et al., 2010, Hexosamine biosynthesis pathway flux promotes endoplasmic reticulum stress, lipid accumulation, and inflammatory gene expression in hepatic cells. Am. J. Physiol. Endocrinol Metab 2010 March; 298(3):E499-511.

Geldanamycin also induces a loss of signalling from the insulin receptor (IR) as measured by lack of IRS-1 activation. In untreated cells, monomeric ab insulin receptor precursor chains are converted to the final α2β2 tetrameric form. In geldanamycin-treated cells, insulin receptor assembly progressed only as far as monomer precursor formation with retained precursor chains associating with CNX at elevated levels compared to untreated cells, and rapidly degraded after 2 h (Saitoh et al., 2002 Down-regulation of cell surface insulin receptor and insulin receptor substrate-1 phosphorylation by inhibitor of 90-kda heat-shock protein family: endoplasmic reticulum retention of monomeric insulin receptor precursor with calnexin in adrenal chromaffin cells. Mol Pharmacol 62: 847-855). The insulin receptor has been shown to be elevated in thyroid cancer where it is capable of forming a hybrid receptor complex with IGF-1R (Belfiore et al., 1999 Insulin/IGF-I hybrid receptors play a major role in IGF-I signalin in thyroid cancer. Biochimie 81: 403-407), the receptor of insulin-like growth factor (IGF)-I and IGF-H. Use of knockout cells has shown that both IGF-I and IGF-II secretion are dependent on GRP94 (Ostrovsky et al., 2010, Glucose regulated protein 94 is required for muscle differentiation through its control of the autocrine production of insulin-like growth factors. Biochim Biophys Acta 1803: 333-341). Geldanamycin and other GRP94 inhibitors are suggested as one approach for putative IGF-II-targeted anticancer therapies (McLaughlin and Vandenbroeck, 2011).

Hsp90 inhibitors under clinical evaluation exhibit pan-inhibitory activity, which results in disruption of all four human isoforms. Detrimental toxicity profiles observed in clinical trials may result from the degradation of necessary Hsp90 clients, such as the human Ether-à-go-go (hERG) channel in the case of cardiotoxicity. Due to the high sequence homology of Hsp90 paralogs, the development of isoform selective inhibitors was deemed improbable. Herein, the design, synthesis and biological evaluation of the first synthetic small molecule isoform-selective inhibitor is disclosed. Most preferably, the new GRP94 selective inhibitors have decreased toxicity, increased solubility, as well as increased selectivity for the GRP94 isoform over cytosolic Hsp90 isoforms.

Molecular chaperones play an integral role in cellular homeostasis, and maintain the proper folding, stabilization, activation and degradation of proteins. Heat shock proteins represent a class of molecular chaperones that are overexpressed as a consequence of cellular stress. The 90 kDa heat shock proteins (Hsp90) have elicited a strong interest from both academic and industrial laboratories as a target for cancer chemotherapeutic development. Hsp90 possess many attributes that make it a promising drug target: 1) Hsp90 is overexpressed in a highly activated state in transformed cells, allowing for differential selectivity between cancer tissue and normal tissue; 2) numerous Hsp90 dependent substrates provide oncogenic roles, and thus through Hsp90 inhibition disruption of multiple oncogenic hallmarks can be established, and 3) Hsp90 is ATP-dependent and contains a conformationally unique nucleotide binding pocket, which allows for selective inhibition versus other ATP-dependent proteins. While several Hsp90 N-terminal inhibitors have progressed into clinical development, detriments have arisen that may preclude FDA approval. Cardiovascular, ocular, and hepatotoxicity are common with many inhibitors currently under clinical evaluation. Recent reports have suggested these toxicity issues may be arising from pan Hsp90 inhibition, as the inhibitors currently target all four human isoforms. Consequently, it has been proposed that inhibitors that possess isoform-selective inhibition may mitigate the observed toxicities and provide new biochemical probes to further delineate the biological roles of each Hsp90 isoform.

As described above, there are four Hsp90 isoforms encoded by the human genome, which include the cytosolic forms Hsp90α (inducible) and Hsp90β (constitutive), the mitochondrial-localized tumor necrosis factor receptor-associated protein (TRAP1) and the endoplasmic reticulum localized glucose-regulated protein (Grp94). Although little is known about TRAP1, recent reports have revealed multiple clients of Grp94, including Toll-like receptors (TLR1, TLR2, TLR4 and TLR9), integrins (CD11a, CD18, CD49d, α4, β7, αL and β2) and immunoglobulins. The clientele of Grp94 supports a role for the chaperone in neoplastic progression, especially in metastasis and immuno-evasion of transformed cells. Existence of small molecule Grp94-selective inhibitors is lacking and exposes a potential opportunity in Hsp90 research. However, all four isoforms contain a highly conserved (~85%) N-terminal ATP-binding region, representing a significant challenge.

Hsp90 contains an atypical nucleotide binding pocket, which allows for the development of selective inhibitors. Dutta, R.; Inouye, M. GHKL, An emergent ATPase/kinase superfamily. *Trends Biochem. Sci.* 2000, 25, 24-28. Several of these Hsp90 N-terminal inhibitors, e.g., 17-AAG (Phase I-III), SNX-5422 (Phase I), CNF2024 (Phase II) and NVP-AUY922 (Phase I/II) have been evaluated clinical trials for various indications, including but not limited to melanoma, multiple myeloma, refractory solid tumors, and breast cancer, shown below. Kim, Y. S.; Alarcon, S. V.; Lee, S.; Lee, M. J.; Giaccone, G.; Neckers, L.; Trepel, J. B. Update on Hsp90 inhibitors in clinical trial. *Curr. Top. Med. Chem.* 2009, 9, 1479-1492.

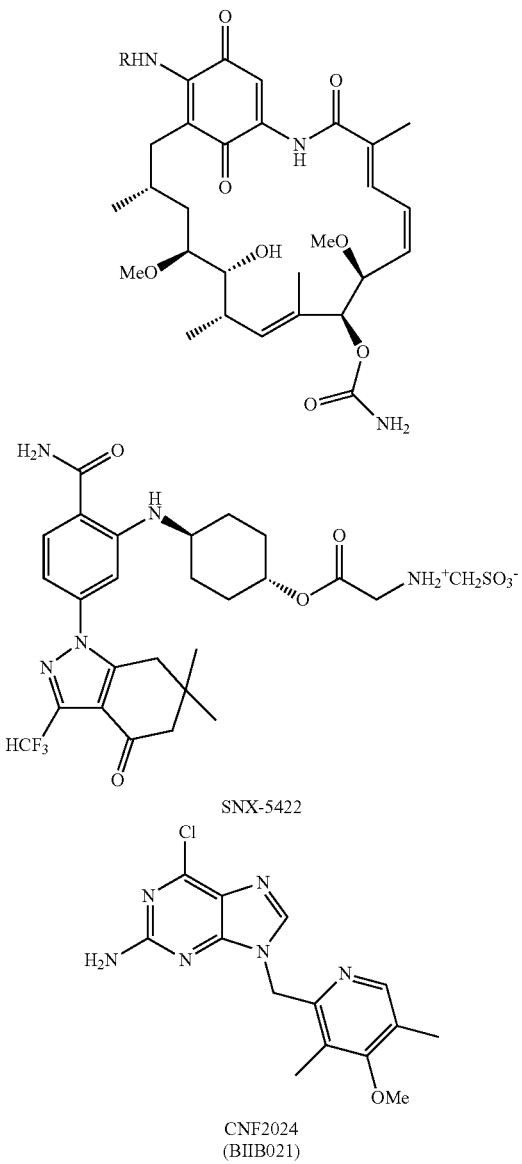

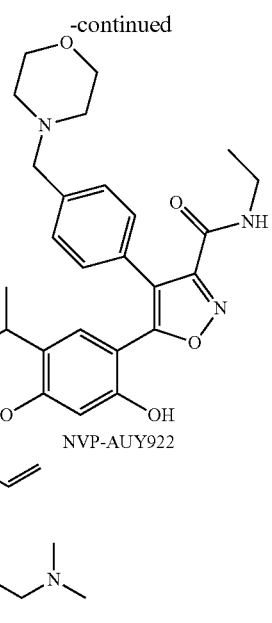

Hsp90 inhibitors previously or currently under clinical evaluation.

Unfortunately, cardiovascular, ocular, and/or hepatotoxicities have been observed in clinical trials. Biamonte, M. A.; Van de Water, R.; Arndt, J. W.; Scannevin, R. H.; Perret, D.; Lee, W. Heat shock protein 90: inhibitors in clinical trials. *J. Med. Chem.* 2010, 53, 3-17.; Holzbeierlein, J.; Windsperger, A.; Vielhauer, G. Hsp90: A Drug Target? *Curr. Oncol. Rep.* 2010, 12, 95-101. Pan-Hsp90 inhibition may be the cause for these effects, as clinical inhibitors are known to target all four human isoforms; Hsp90α, Hsp90β, Trap1 and Grp94. Hsp90α (inducible) and Hsp90β (constitutively active) are the cytosolic isoforms, whereas tumor necrosis factor receptor associated protein (TRAP1) is localized to the mitochondria, and glucose-regulated protein, Grp94, resides in the endoplasmic reticulum. Little is known about the client protein selectivity manifested by each of the four isoforms, and this gap in understanding may underlie the toxicity concerns that have arisen in clinical trials. Despite the clinical significance of Hsp90 inhibition, little investigation towards the development of isoform-selective inhibitors has been pursued to delineate isoform-dependent substrates, or as an opportunity to reduce the potential side effects that result from pan-inhibition.

Unlike the cytosolic chaperones, Hsp90α and Hsp90β, which have been well-studied, little is known about TRAPI and Grp94. At present, no isoform specific clients have been described for TRAP-1; in fact, neither the crystal nor the solution structure has been solved. In contrast, Grp94 co-crystal structures have recently been determined, and demonstrate this isoform to exhibit a unique secondary binding pocket that may provide an opportunity to develop isoform-selective inhibitors.[18-24] Unlike TRAP-1, several substrates dependent upon Grp94 have been identified and include Toll-like receptors (TLR1, TLR2, TLR4 and TLR9), integrins (CD11a, CD18, CD49d, α4, β7, αL and β2), IGF-I and -II and immunoglobulins.[25-34] Since these clients play key roles in cell-to-cell communication and adhesion, Grp94-selective inhibitors may disrupt malignant progression by preventing metastasis, migration, immunoevasion and/or cell adhesion.[30-33,35-38] Interestingly, many of these Grp94-dependent clients have also been identified as key contributors to inflammatory disorders such as rheumatoid arthritis, diabetes and asthma.[29,32,39-40] Therefore, the ability to develop a Grp94-selective inhibitor may not only provide a new paradigm for Hsp90 inhibition, but may also provide new opportunities for the treatment of diseases other than cancer.

The biological roles manifested by Grp94 have been primarily elucidated through the use of RNAi induced Grp94 knockdown, immunoprecipitation experiments, or through pan-inhibition of all four Hsp90 isoforms. A selective small molecule inhibitor of Grp94 would provide an alternative and potentially powerful method for further elucidation of the roles manifested by Grp94, as well as the identity of other Grp94-dependent processes/substrates. Recently, the co-crystal structures of the chimeric inhibitor, radamide (RDA), bound to the N-terminal domain of both the yeast ortholog of cytosolic Hsp90 (yHsp82N, PDB: 2FXS) and the canine ortholog of Grp94 (cGrp94NΔ41, PDB: 2GFD) were described.[21] Utilizing a structure-based approach that relied upon these co-crystal structures, a new class of inhibitors that target Grp94 has been developed.

Previously, we developed a class of chimeric inhibitors containing the quinone moiety of geldanamycin (GDA) and the resorcinol moiety of radicicol (RDC). The combination of these functionalities resulted in small molecule Hsp90 N-terminal inhibitors that manifested good potency. Radamide (RDA, FIG. 1A), exhibits a $K_d$ value of 0.52±0.13 µM and 0.87±0.14 µM for Grp94 and the yeast homolog of Hsp90β, respectively (FIG. 1B). Analyses of the co-crystal structures of RDA bound to both Grp94 and yHsp82 suggested the amide conformation was important to the differential binding affinities, as RDA can adopt a cis-amide conformation when bound to Grp94, but maintains the low energy, trans-amide conformation when bound to yHsp82. See Immormino et al., 2009, J. Mol. Biol., 388(5):1033-1042, which is incorporated herein by reference. The cis-amide conformation directs the quinone functionality of RDA into a hydrophobic pocket that is unique to Grp94. This hydrophobic pocket arises via a 5 amino acid insertion into the primary sequence. This inclusion results in a perturbation about the tertiary structure, and creates a binding pocket that can be exploited for selective inhibition.

Design and Synthesis of Grp94 Isoform Selective Inhibitors.

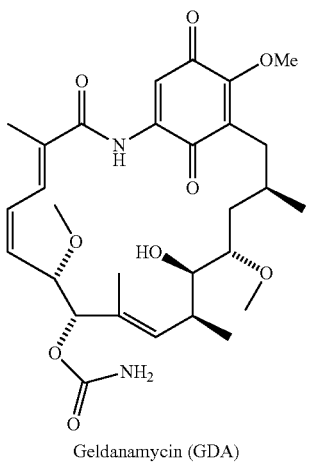

Geldanamycin (GDA)

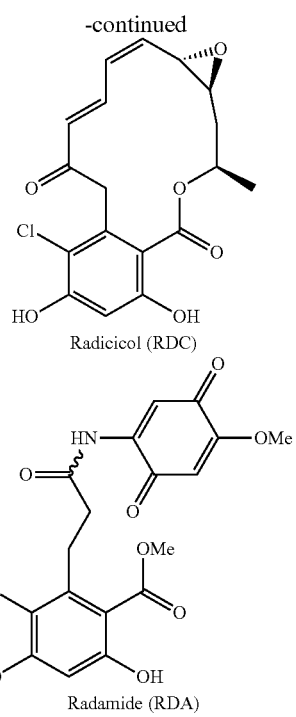

Radicicol (RDC)

Radamide (RDA)

A chimeric approach was taken to design isoform selective Hsp90 inhibitors.

Co-crystal structures of the natural products, geldanamycin (GDA) and radicicol (RDC), bound to the highly conserved N-terminal region have been solved.[18-21,24] Subsequent studies showed that chimeric inhibitors containing the quinone moiety of GDA and the resorcinol of RDC also target this domain.[41-44] Three chimeric scaffolds were identified as Hsp90 inhibitors that manifested anti-proliferative activity against various cancer cell lines. Radamide (RDA) was the first chimera produced, and the first co-crystallized with cytosolic Hsp90 from yeast (yHsp82) and Grp94 from canine (cGrp94N6.41) by the Gewirth laboratory.[21,41-42] Analyses of the two co-crystal structures (FIG. 7A-C) revealed the resorcinol ring to bind similarly in both isoforms, making a direct hydrogen bond with the conserved aspartic acid residue (Asp79 in yHsp82 and Asp 149 in cGrp94NΔ41) involved in ATP binding. However, the quinone moiety was found to bind yHsp82N in a linear, trans-amide conformation, which was distinct from one conformation observed in the cGrp94N6.41 co-crystal structure. Upon binding cGrp94NΔ41, two opposing conformations of RDA were observed (50% occupancy each): One conformation exhibited a cis-amide orientation and projected the quinone moiety into a hydrophobic pocket that exists solely in Grp94 due to a five amino acid insertion into the primary sequence. The second conformation of RDA observed in the RDA·cGrp94NΔ41 co-crystal structure presented the amide in a trans-configuration and projected the quinone toward the outside of the binding pocket, similar to that observed for RDA in the yHsp82N co-crystal structure.[21] Interestingly, RDA was found to exhibit an approximately 2-fold higher binding affinity for full-length Grp94 than yHsp82.

Figure 7:
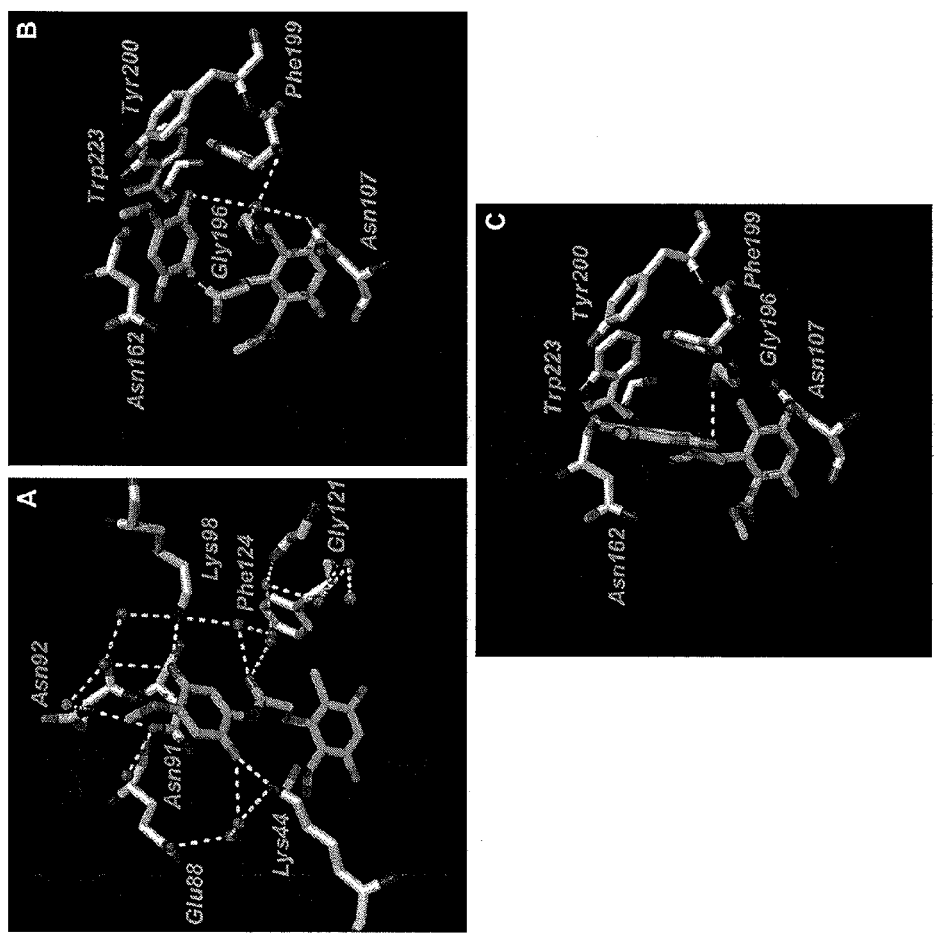
FIG. 7 shows (A) RDA quinone hydrogen-bonding network comparison between yHsp82N; (B) cGrp94NΔ41 with RDA cis-amide and (C) RDA trans-amide. Spheres represent water molecules, while hashed lines represent a hydrogen-bonding interaction.

Further analyses of the RDA·yHsp82N co-crystal structure revealed the quinone to mediate an intricate hydrogen-bonding network, whereas its interaction with cGrp94NΔ41 was limited (FIG. 7). For example, in the RDA·yHsp82N structure, direct hydrogen bonds between the RDA quinone and Lys98 and Lys44 were observed. In contrast, no direct hydrogen bonds were observed between cGrp94NΔ41 and the cis-amide quinone (FIG. 7B), suggesting that functionalities on the quinone ring may be dispensable for Grp94 binding, but obligatory for cytosolic Hsp90 binding. In addition, this Grp94 hydrophobic pocket contains aromatic amino acids (Phe199, Tyr200 and Trp223) that are likely to facilitate π-stacking interactions, and could be utilized for the design of inhibitors that exhibit increased selectivity and affinity for Grp94 over cytosolic Hsp90. Although the primary sequences and ATP-binding pockets are highly homologous (>70% similar, 55% identical), this minor disparity was exploited for the rational design of Grp94 inhibitors.[17] The design elements were focused on the conformation of RDA when bound to cGrp94NΔ41 versus yHsp82N, the dispensability of the quinone moiety, and the hydrophobicity of the Grp94 π-rich pocket. Based on these observations, we hypothesized that inhibitors containing a more hydrophobic surrogate of the quinone linked to the resorcinol through a cis-amide bioisostere would provide compounds that inhibit Grp94 selectively.

Based on the co-crystal structures of RDA with GRP94, a structure-based approach to develop conformationally rigid analogs of RDA that exhibit a cis-amide conformation was pursued. Initial studies produced cis-radamide (cRDA, FIG. 1A), which exhibited an improved $K_d$ value for Grp94 of 0.11±0.02 μM (FIG. 1B), although the $K_d$ value for yHsp82 also improved to 0.24±0.12 μM. These results confirmed that a cis-amide conformation increased binding affinity for Grp94, and suggested that a bioisosteric replacement of the cis-amide functionality may enhance isoform selectivity. Molecular modeling and computational studies were enlisted to identify small molecules that contained bioisosteric replacements that resulted in selective Grp94 inhibition. Various analogs of RDA are disclosed in Hadden and Blagg, 2009, Synthesis and evaluation of radamide analogues, a chimera of radical and geldanamycin, J. Org. Chem., July 3; 74(13):4697-4704, which is incorporated herein by reference.

Figure 14:
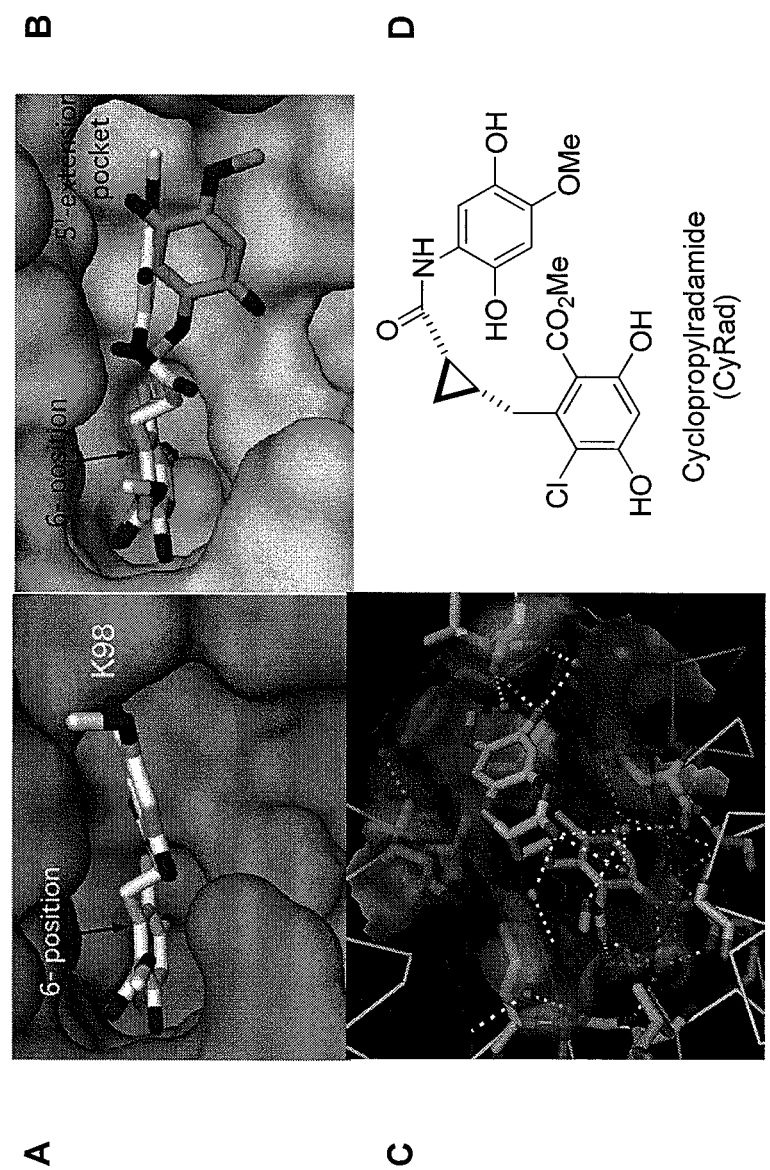
FIG. 14 shows. co-crystal structures of radamide bound to Hsp90beta (top left), radamide bound to GRP94 (top right), cis-radamide bound to GRP94 (bottom left), and the structure of CyRad (bottom right).

It has been determined that radamide ($k_d$=254 nM) and cis-radamide ($k_d$=110 nM) bind to the Hsp90 isoform, GRP94, with high affinity. Additionally, the first co-crystal structure of these molecules bound to both GRP94 and Hsp90beta has been solved in collaboration with the Gewirth Laboratory, which clearly establishes the first isoform selective inhibitors produced to date (FIG. 14). As indicated by the co-crystal structures, cis-radamide occupies a hydrophobic cleft near the opening of the pocket, which does not exist in the case of other Hsp90 isoforms. The synthesis of cis-radamide is disclosed, e.g., in Duerfeldt et al., Org. Lett. 2009, June 4; 11(11):2353-2356, which is incorporated herein by reference. In one aspect, the disclosure provides additional cis-radamide analogues that are designed to exhibit increased selectivity.

Multiple bioisosteres exist for the cis-amide functionality; however in this instance, those exhibiting a conformational bias rather than a specific physical property were considered. Observation that the cis-amide conformation of RDA bound to cGrp94NΔ41 projects the quinone moiety into the Grp94 hydrophobic pocket suggested that cis-olefins, carbocycles or heterocycles may represent appropriate surrogates. In the end, imidazole was chosen based on the inclusion of a hydrogen bond acceptor in the same location as the amide carbonyl, which could provide complementary interactions with Asn162 (FIG. 7).

Since no direct hydrogen-bonding interactions exist between the quinone and cGrp94NΔ41, and several π-rich amino acids (Phe199, Tyr200, and Trp223) reside in this secondary pocket, the utilization of an aromatic ring in lieu of the quinone was pursued. A phenyl ring was envisioned to provide the desired π-interactions with Phe199, Tyr200, and Trp223 while providing a rational starting point for the development of Grp94 selective inhibitors. The imidazole linker was expected to project the phenyl ring similar to that observed for the RDA quinone, and therefore the tether between the imidazole and phenyl moiety was analyzed by computational examination. Compounds 1-5 were designed as hypothetical Grp94 inhibitors that contained the three aspects envisioned to be important for inhibition: 1) A resorcinol ring to ensure N-terminal inhibition and correct orientation within in the ATP-binding pocket, 2) a predisposed cis-amide conformation that projected the phenyl appendage toward the unique Grp94 binding pocket, and 3) a hydrophobic, π-rich surrogate for the quinone. The latter of which would be incapable of providing the requisite hydrogen-bonding interactions with cytosolic Hsp90, and should therefore facilitate binding to the n-rich region of Grp94.

Utilizing Surflex molecular docking software, analogs 1-5 were docked to the RDA·cGrp94NΔ41 complex (PDB: 2GFD). As shown in FIG. 1, the Surflex binding scores for compounds 1 and 2 were 1-2 units higher than that of RDA, suggesting binding affinities of 10-100-fold higher for cGrp94NΔ41, respectively. Furthermore, 1-5 failed to dock to the RDA·yHsp82N complex (PDB: 2FXS), supporting our hypothesis that these phenyl imidazole analogs may exhibit selective inhibition. Although 1 and 2 were the only compounds predicted to bind cGrp94NΔ41, prior studies demonstrated the Grp94 lid region to undergo significant variations that are capable of accommodating various ligand sizes and chemotypes. Unfortunately, available modeling programs could not account for this phenomenon and therefore, all five analogs were constructed. Aldehyde 6 (Scheme 1), which was utilized during the synthesis of RDA,[41-42] was readily available and allowed for the rapid preparation of analogs. As shown in Scheme 1, a Radziszewski-like condensation of aldehyde 6 with the requisite aniline/primary amine in the presence of glyoxal and ammonium bicarbonate provided the desired compounds as protected silyl ethers.[45-46] Addition of tetrabutylammonium fluoride to the reaction mixture yielded the desilylated compounds 1-5 in moderate yields Based on the co-crystal structure of cis-radamide bound to GRP94, a bioisoteric replacement for cis-amide that contains an imidazole ring was proposed. 1,2-di-substituted imidazole contains a substitution pattern similar to a cis-amide conformation and was chosen as a suitable bioisosteric replacement. The imidazole linkage can be obtained in a single step from 6, and can therefore be utilized to prepare numerous analogs in a succinct manner. As shown in FIG. 1C, the resorcinol 6 can be treated with benzyl amine, glyoxal, and ammonium bicarbonate to produce the desired compound 2, in acceptable yield. See, for example, Pastor and Yus, 2009, Bioactive N-Phenylimidazole Derivatives, Curr. Chem. Biol., 3:385-408, which is incorporated herein by reference.

Figure 3:
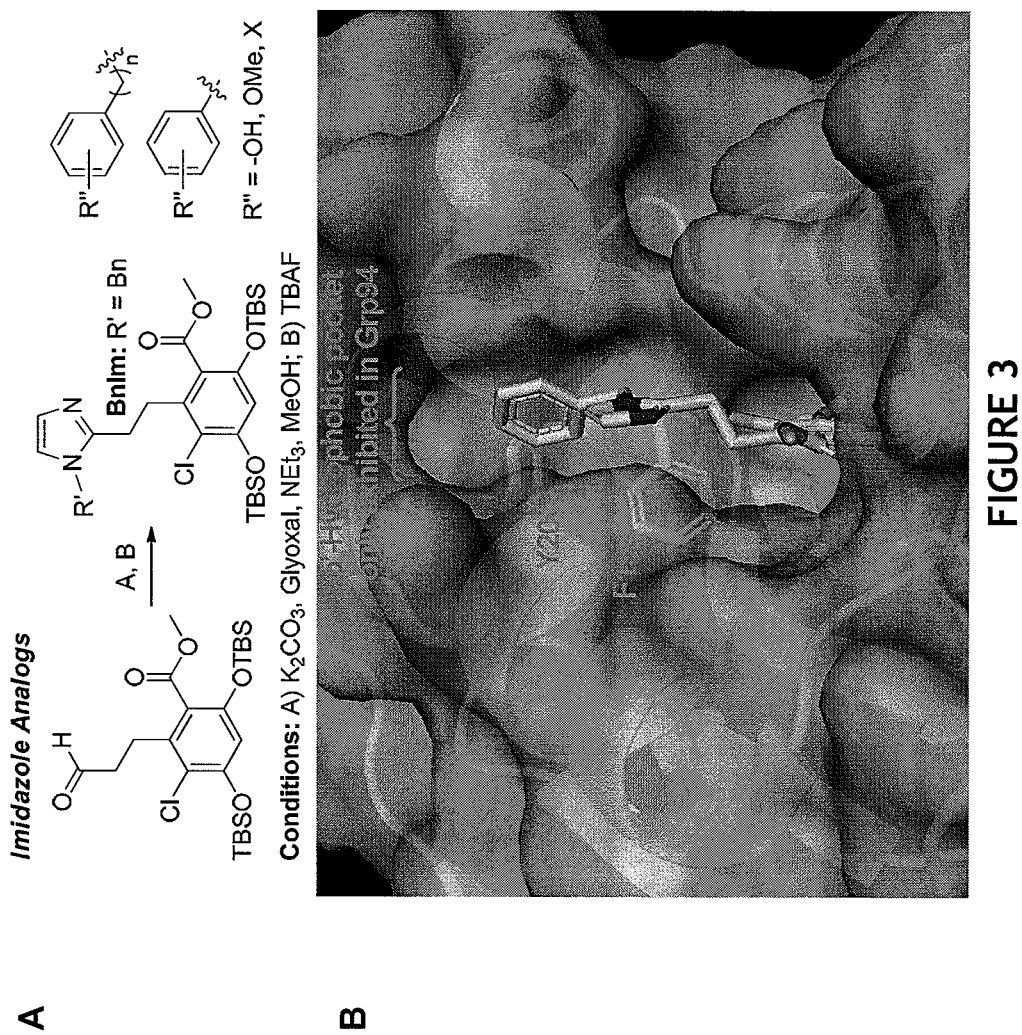
FIG. 3 shows (A) a second synthetic protocol for preparation of imidazole analogs, wherein X is e.g. hal, and (B) a molecular modeling screen shot of docking of GRP94-selective imidazole derivatives. Exploitation of the hydrophobic pocket with the aromatic side chain of the imidazole derivatives is proposed to enhance selectivity for GRP94.

Consistent with the molecular modeling predictions, the first compound synthesized, BnIm, compound 2, exhibits ~100:1 selectivity for GRP94 versus cytoplasmic Hsp90alpha/beta, as determined by inhibition of GRP94-mediated Toll presentation at the cell surface versus Western blot analysis of Hsp90-dependent proteins found in the cytoplasm (See SA4). As described in FIG. 3, further modification of the aryl side chain was designed to enhance interactions with the GRP94 binding site.

In one aspect, the disclosure provides GRP94 selective compounds of Formula I:

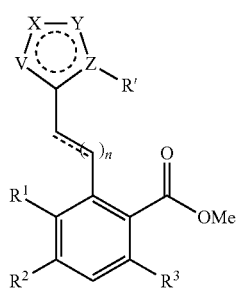

wherein

V, X, and Y are each independently selected from CH, NH or N;

Z is selected from C or N;

$R^1$ is selected from the group consisting of H, F, Cl, Br, I, methyl, ethyl, n-propyl, isopropyl, butyl, phenyl, and benzyl;

$R^2$ is selected from the group consisting of H, OH, SH, and $NH_2$;

$R^3$ is selected from the group consisting of H, OH, SH, and $NH_2$;

R' is selected from the group consisting of

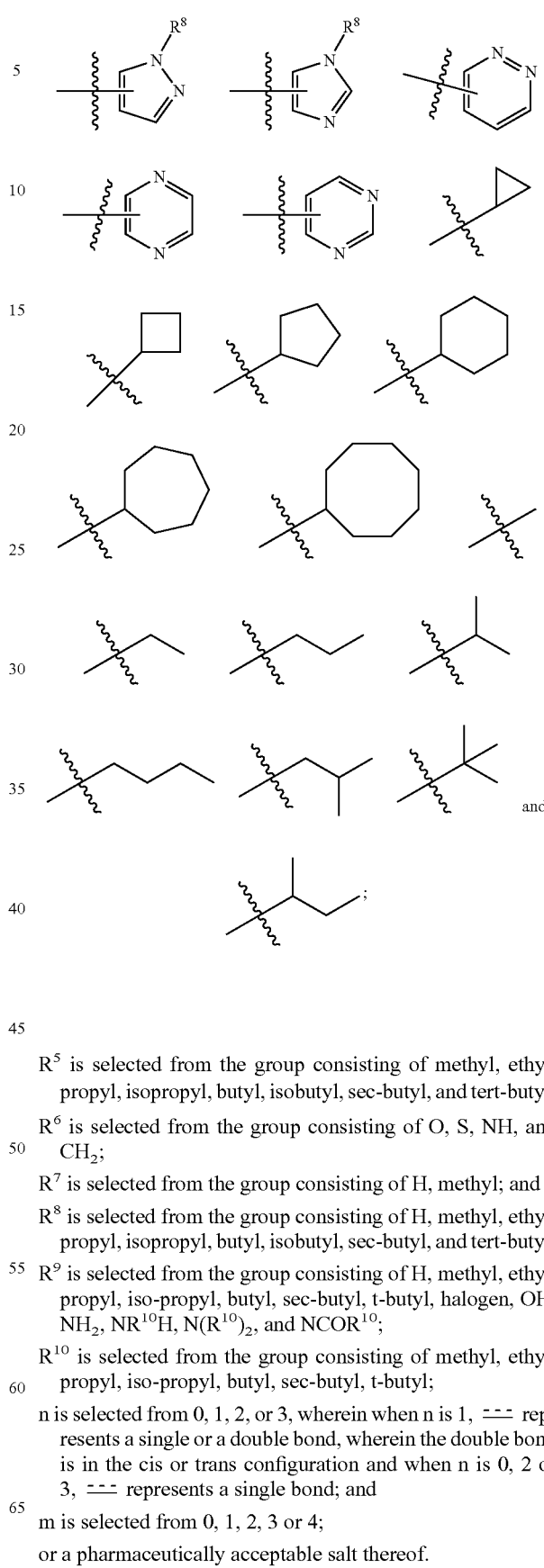

$R^5$ is selected from the group consisting of methyl, ethyl, propyl, isopropyl, butyl, isobutyl, sec-butyl, and tert-butyl;

$R^6$ is selected from the group consisting of O, S, NH, and $CH_2$;

$R^7$ is selected from the group consisting of H, methyl; and $R^8$ is selected from the group consisting of H, methyl, ethyl, propyl, isopropyl, butyl, isobutyl, sec-butyl, and tert-butyl;

$R^9$ is selected from the group consisting of H, methyl, ethyl, propyl, iso-propyl, butyl, sec-butyl, t-butyl, halogen, OH, $NH_2$, $NR^{10}H$, $N(R^{10})_2$, and $NCOR^{10}$;

$R^{10}$ is selected from the group consisting of methyl, ethyl, propyl, iso-propyl, butyl, sec-butyl, t-butyl;

n is selected from 0, 1, 2, or 3, wherein when n is 1, --- represents a single or a double bond, wherein the double bond is in the cis or trans configuration and when n is 0, 2 or 3, --- represents a single bond; and m is selected from 0, 1, 2, 3 or 4;

or a pharmaceutically acceptable salt thereof.

In another aspect, the compound according to Formula I is:

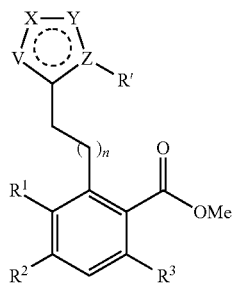

wherein --- represents a single bond, and the remaining substituents are described as above for Formula I.

In another aspect, the disclosure provides GRP94 selective inhibitor compounds of Formula II:

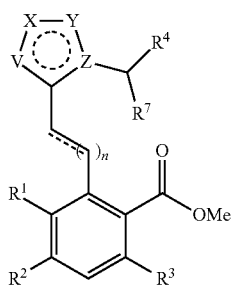
(II)

wherein the substituents are described as above; except that $R^7$ is selected from H, methyl and dimethyl.

In another aspect, the compound according to formula II is:

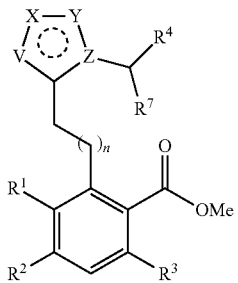

wherein --- represents a single bond, and the remaining substituents are described as above for Formula II.

In a further aspect, the disclosure provides GRP94 selective inhibitor compounds of Formula III:

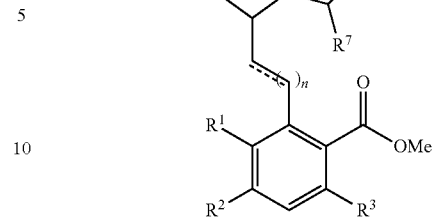
(III)

wherein the substituents are described as above; except that $R^7$ is selected from H, methyl and dimethyl.

In another aspect, the compound according to Formula III is:

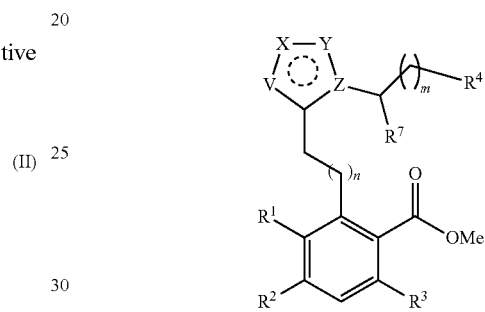

wherein --- represents a single bond, and the remaining substituents are described as above for Formula III.

In various preferred aspects, for the compounds of Formula I, II or III:

In one preferred aspect, X and Y are each CH.
In one preferred aspect, V is NH.
In one preferred aspect, Z is N.
In one preferred aspect, $R^1$ is F, Cl or Br.
In a further preferred aspect, $R^1$ is Cl.
In one preferred aspect, $R^2$ is OH.
In one preferred aspect, $R^3$ is O.
$R^4$ is selected from the group consisting of

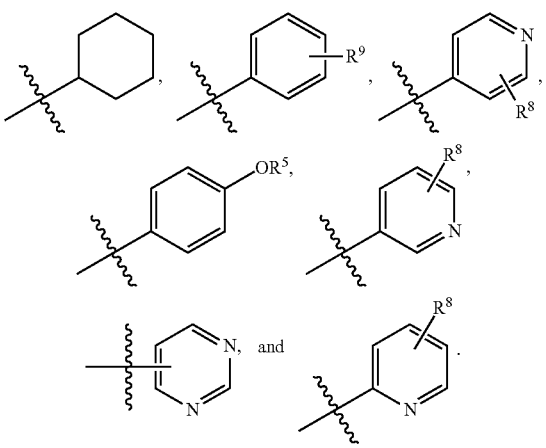

In one preferred aspect, R' is
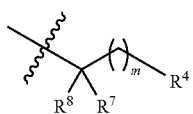
and m is 0, and $R^7$ and $R^8$ are independently H or $CH_3$.
In a particular aspect, the disclosure provides imidazole derivatives that are GRP94 selective inhibitor compounds of the following structures.
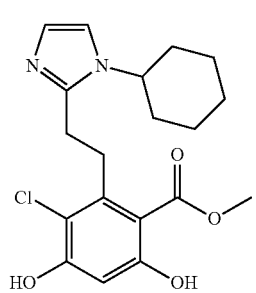 , 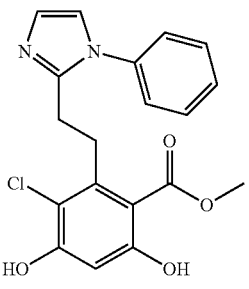 ,
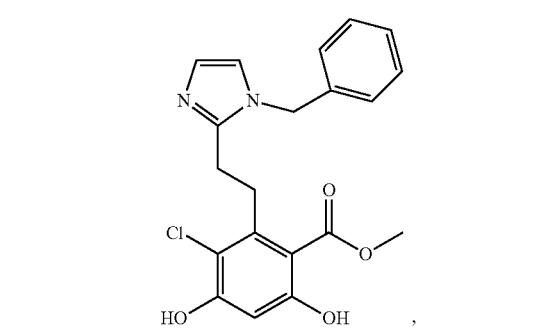 ,
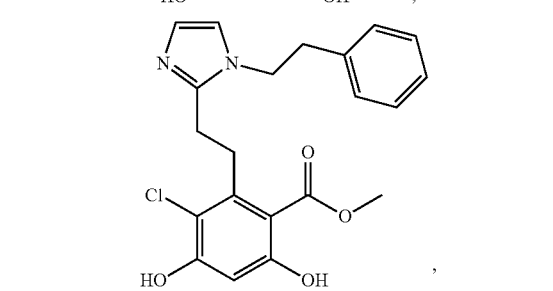 ,
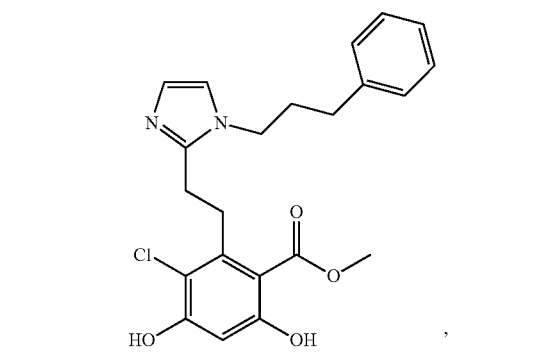 ,
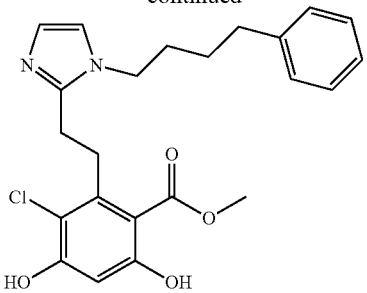 ,
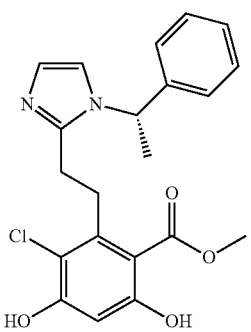 ,
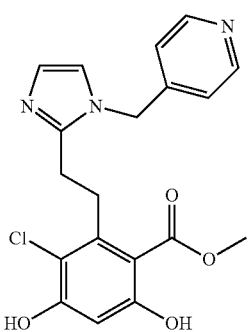 ,
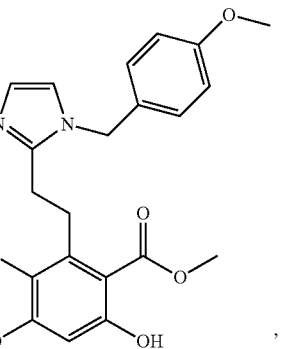 ,
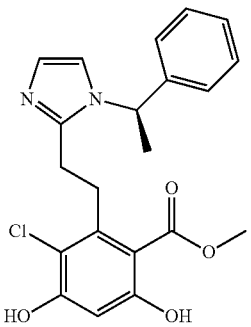 ,

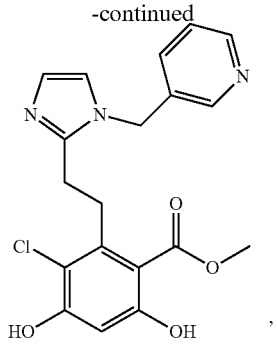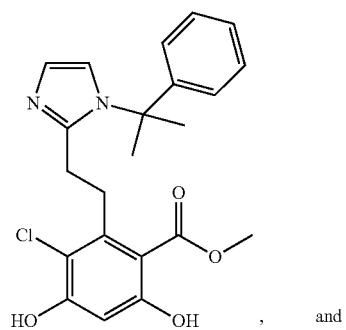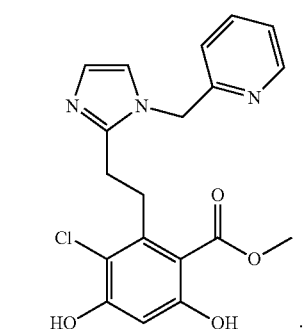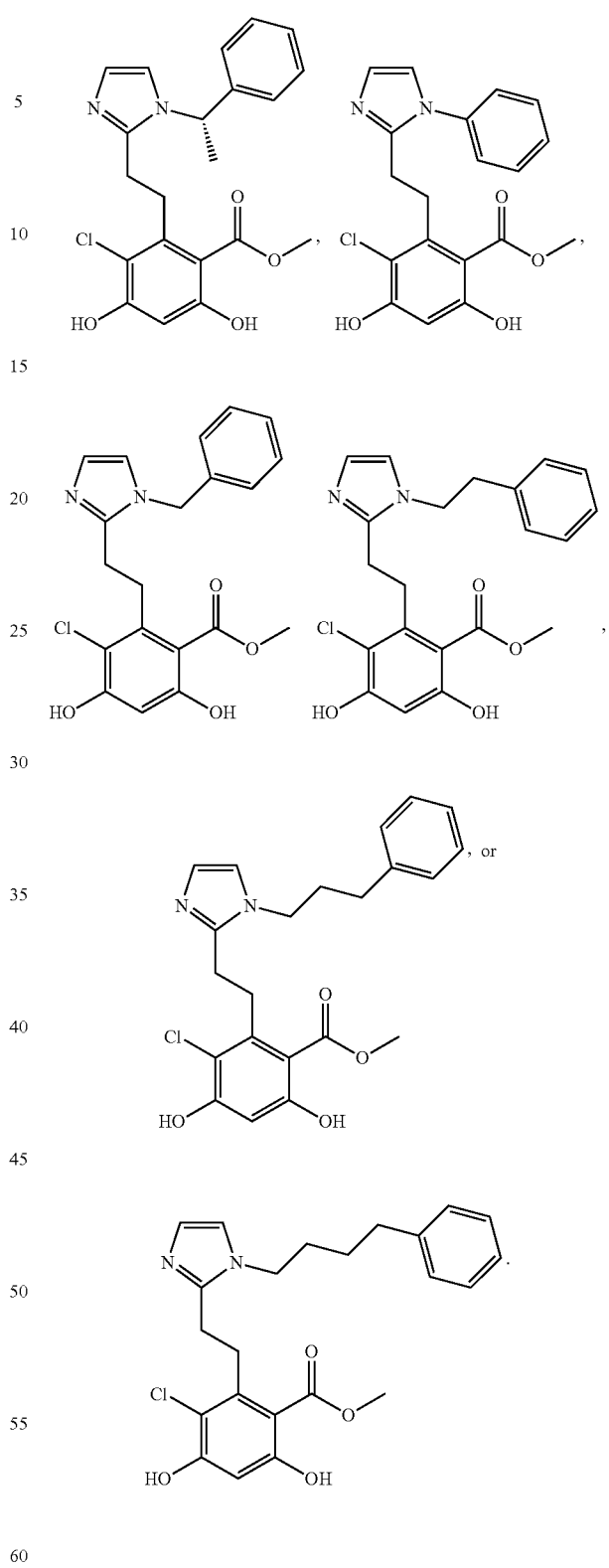
In a specific aspect, the disclosure provides an imidazole derivative that is a GRP94 selective inhibitor compound of the following structure:
In another specific aspect, the disclosure provides an imidazole derivative that is a GRP94 selective inhibitor compound of the following structure:

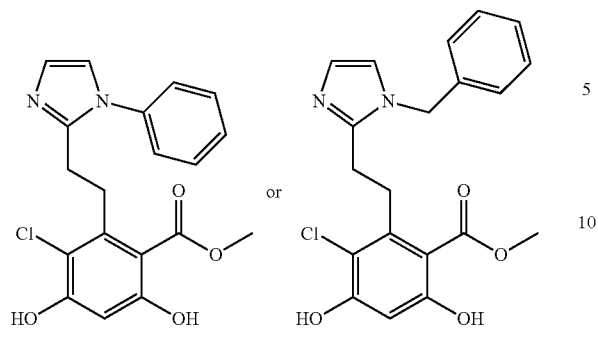

In a preferred aspect, the GRP94 selective inhibitor is

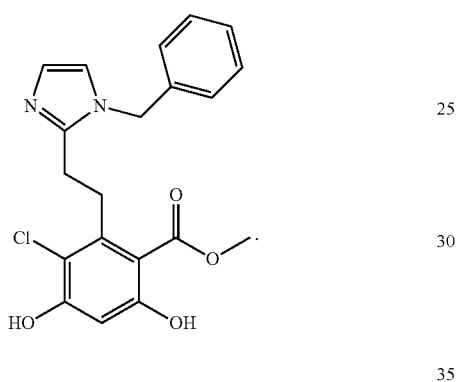

In another preferred aspect, the GRP selective inhibitor is methyl 2-(2-(1-benzyl-1H-imidazol-2-yl)ethyl)-3-chloro-4,6-dihydroxybenzoate.

In another embodiment, the disclosure provides compounds of Formula I wherein ═══ represents a double bond. In a specific aspect, the double bond is in the cis configuration. In particular the trans alkene can be converted to the cis alkene by use of Lindlar's catalyst. A representative synthetic route is shown in Scheme 1.

Scheme 1.

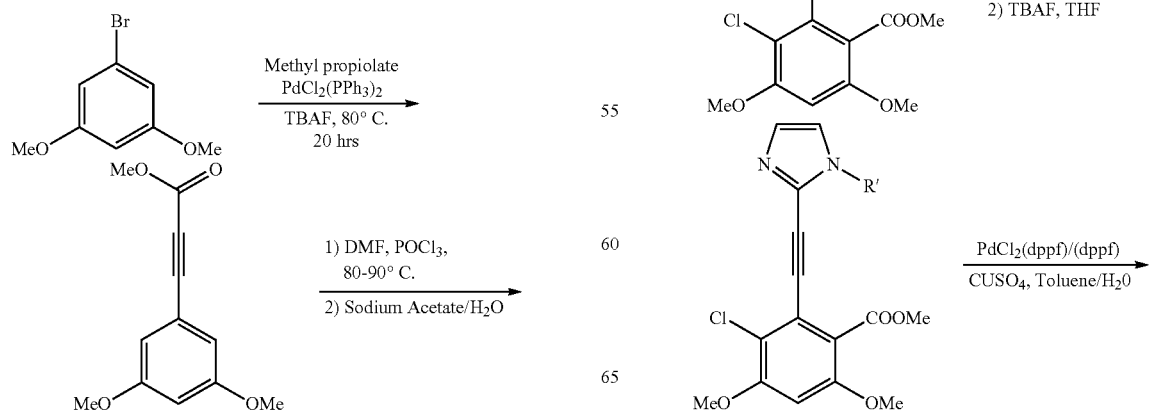

-continued
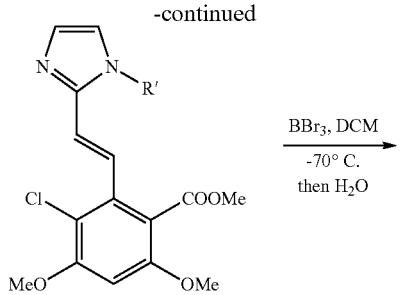
BBr₃, DCM
-70° C.
then H₂O
→
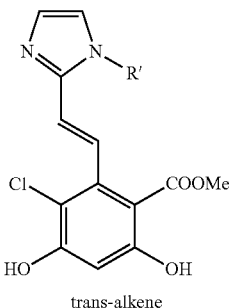
Lindlar's Catalyst
H₂
→
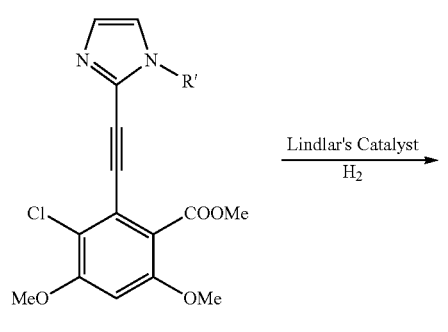
BBr₃, DCM
-70° C.
then H₂O
→
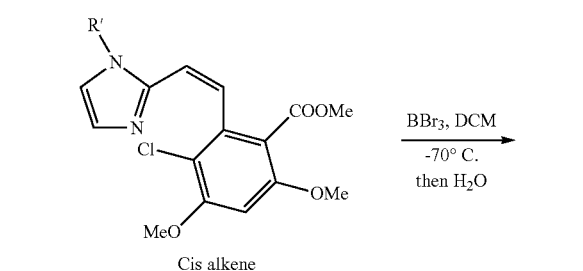
Cis alkene
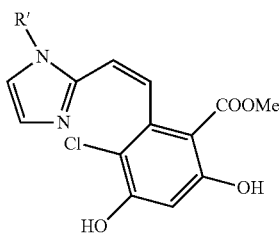
In an embodiment, the disclosure provides a GRP94 selective inhibitor of Formula VI:
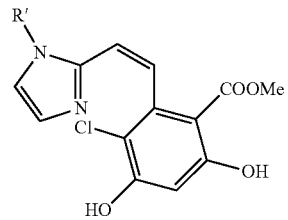 (VI)
wherein R' is selected from
R' is selected from the group consisting of
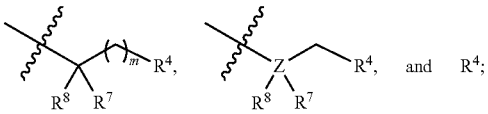
$R^4$ is selected from the group consisting of
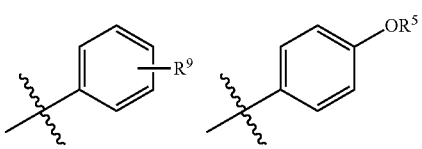
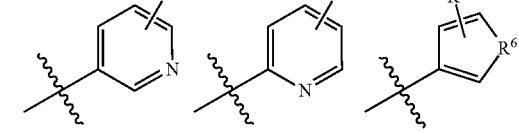
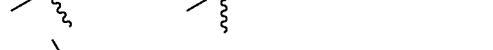
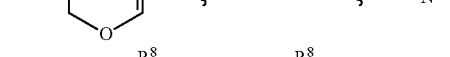
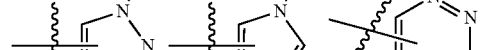
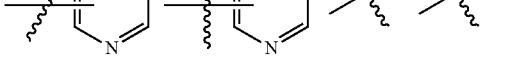
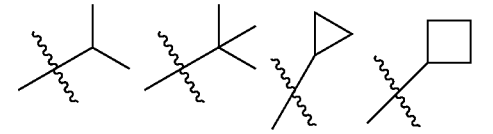

-continued

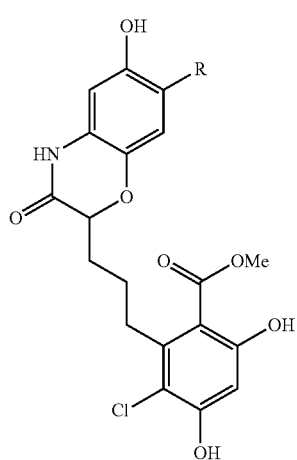

$R^5$ is selected from the group consisting of methyl, ethyl, propyl, isopropyl, butyl, isobutyl, sec-butyl, and tert-butyl;
$R^6$ is selected from the group consisting of O, S, NH, and $CH_2$;
$R^7$ is selected from the group consisting of H, and methyl; and
$R^8$ is selected from the group consisting of H, methyl, ethyl, propyl, isopropyl, butyl, isobutyl, sec-butyl, and tert-butyl;
$R^9$ is selected from the group consisting of H, methyl, ethyl, propyl, iso-propyl, butyl, sec-butyl, tert-butyl, halogen, OH, $NH_2$, $NR^{10}H$, $N(R^{10})_2$, and $NCOR^{10}$;
$R^{10}$ is selected from the group consisting of methyl, ethyl, propyl, isopropyl, butyl, sec-butyl, and tert-butyl;
m is selected from 0, 1, 2, 3 or 4;
or a pharmaceutically acceptable salt thereof.

Figure 15:
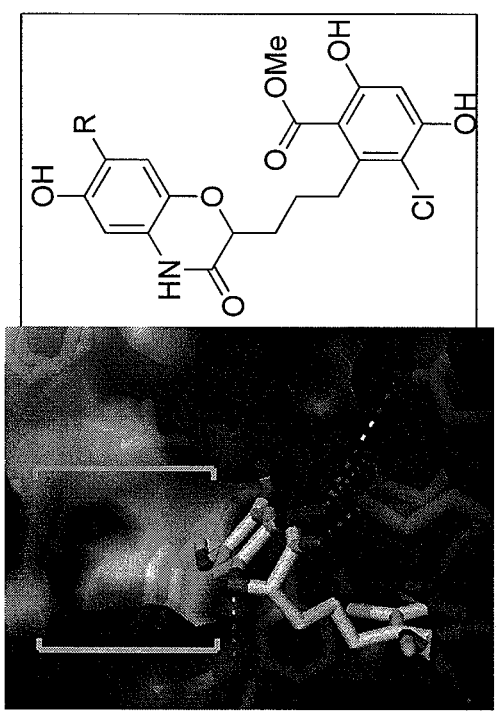
FIG. 15 shows probing the GRP94 lipophlic pocket by preparation of ether/amine analogs.
Figure 15:
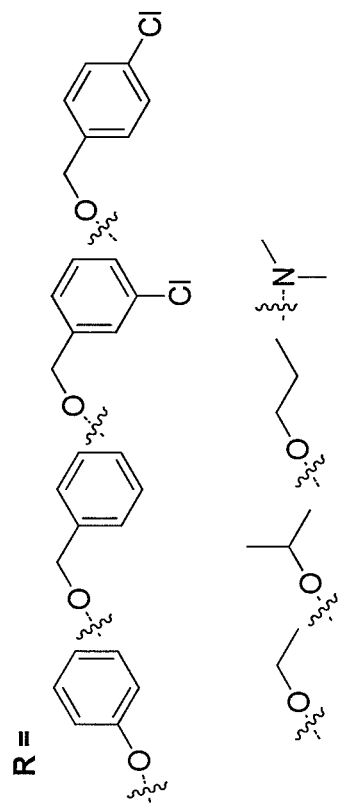

In another embodiment, as shown in FIG. 14, cis-radamide binds GRP94 and projects the 4-methoxy group into a lipophilic pocket that contains a tyrosine phenol at the opening. This pocket does not exist in the Hsp90beta co-crystal structure with cis-radamide and thus provides a mechanism to further enhance isoform selectivity. To provide complementary interactions with both the tyrosine phenol and the lipophilic pocket, the compounds outlined in FIG. 15 were designed. These modifications will be made by any route, for example, via modification of our previously reported synthetic route for cis-radamide, e.g., as disclosed in Duerfeldt et al., 2009, which is hereby incorporated herein by reference. In another aspect, the disclosure provides GRP94 selective compounds of Formula V:

(V)

wherein R is X'—$R^4$; wherein X' is selected from S, $SO_2$, SO, O, NH, and Ne; $R^4$ is as defined above; and $R^{10}$ is as defined above.

In one specific aspect, the disclosure provides GRP94 selective compounds of Formula V wherein R is X'—$R^4$; wherein X' is selected from O, NH, and Ne; $R^4$ is as defined above; and $R^{10}$ is as defined above.

In another specific aspect, the disclosure provides GRP94 selective compounds of Formula V wherein R is selected from

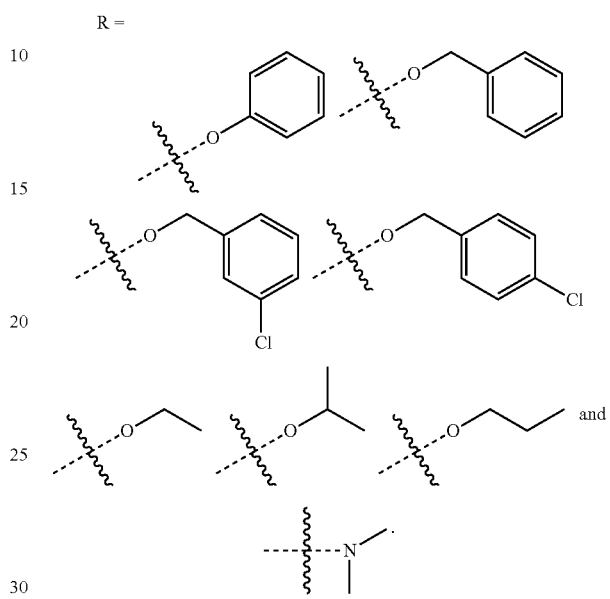

Figure 6:
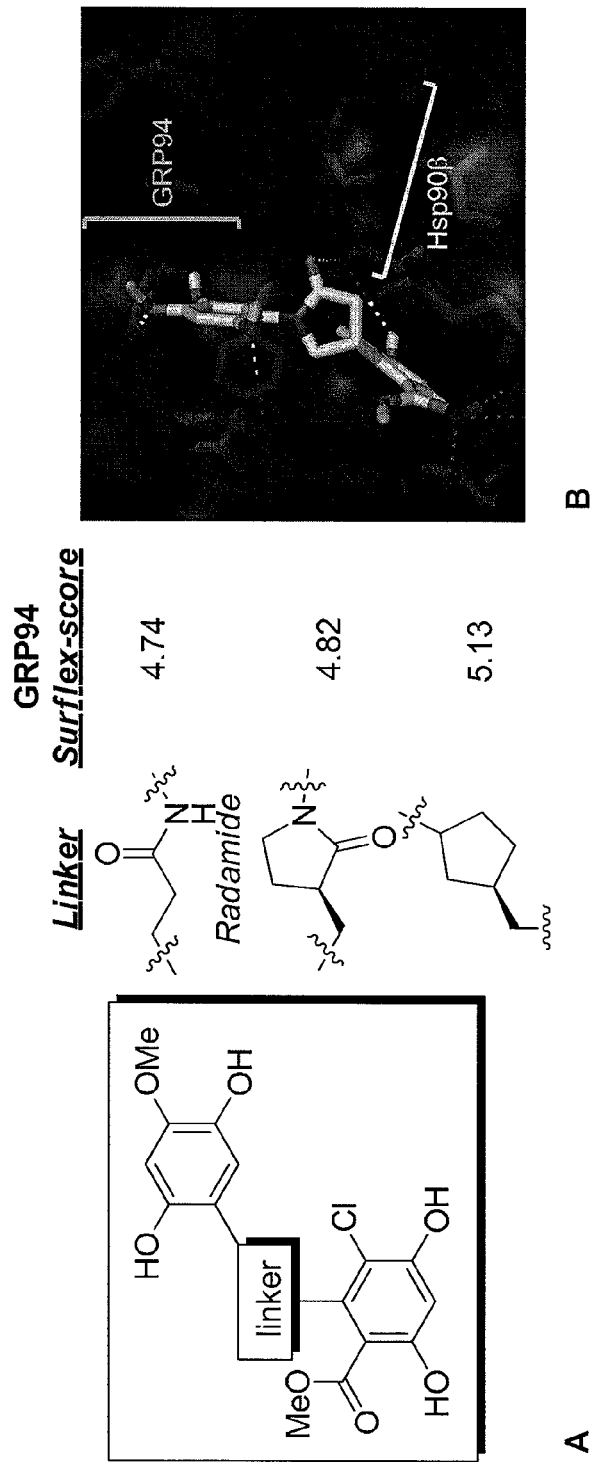
FIG. 6 shows a generic series of radamide analogues with incorporation of linearized linkers with respective GRP94 Surflex-scores, (A) designed to extend into the GRP94 binding site based upon molecular modeling studies, as shown at (B).

In one aspect, in order to extend into the lipophilic pocket of the GRP94 binding site, linearized tethers, or linkers, are utilized. As shown in FIG. 6, these "linearized" tethers exhibit a predisposed geometry that binds only to the GRP94 ATP-binding site and are not capable of binding to Hsp9013. Therefore, the tethered analogues shown will be prepared to further enhance isoform selectivity toward the GRP94 binding site, while simultaneously replacing the hydroquinone with previously identified non-redox-active isosteres which can be readily assembled through Cu-mediated N-arylation. See, for example, Pastor and Yus, 2009; Altman et al., 2007, Copper-catalyzed N-arylation of imidazoles and benzimidazoles, J. Org. Chem., 72(16):6190-6199 and Altman and Buchwald, 2006, Org. Lett., 8(13):2779-2782, each of which is incorporated herein by reference.

To extend into the lipophilic pocket of the GRP94 binding site, linearized tethers will also be utilized. As shown in FIG. 6, these "linearized" tethers exhibit a predisposed geometry that binds only to the GRP94 ATP-binding site and are not capable of binding to Hsp90beta. Therefore, the tethered analogues shown were designed to further enhance isoform selectivity toward the GRP94 binding site, while simultaneously replacing the hydroquinone with previously identified non-redox-active isosteres, including the cis-radamide variants and the imidazole derivatives as outlined in FIG. 3.

In one aspect, the disclosure provides GRP94 selective compounds of Formula IV:

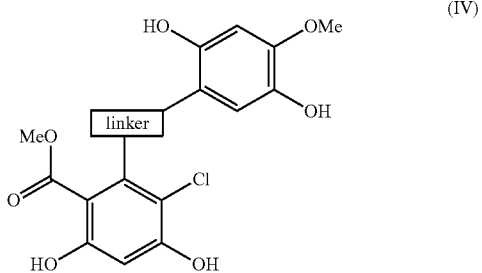

(IV)

wherein the linker is selected from

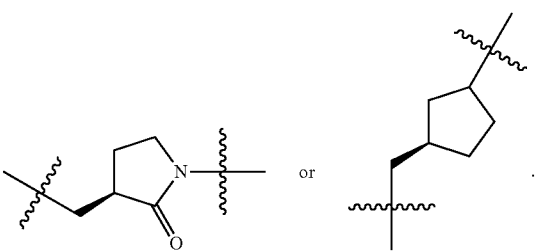 [SMILES: *C[C@H]1CCN(*)C1=O ; *C[C@@H]1CCC(*)C1]

In one aspect, the selective Grp94 inhibitor compounds of the invention can be used to inhibit any all Grp94-dependent process.

In one aspect, the Grp94 inhibitor compounds of the invention prevent or decrease intracellular trafficking of the Toll receptor.

In another aspect, the Grp94 inhibitor compounds of the invention inhibit secretion of IGF-II.

In a further aspect, the Grp94 inhibitor compounds of the invention affect the conformation of Grp94.

In another aspect, the Grp94 inhibitor compounds of the invention suppress *Drosophila* larval growth.

In one aspect, the selective Grp94 inhibitor compounds of the invention have no effect on cell viability or cytosolic Hsp90α/β client proteins at concentrations effective to inhibit Grp94 dependent processes.

Preparation of the imidazole compounds can be performed by any method known in the art, for example, see Arduengo et al., U.S. Pat. No. 6,177,575, which is incorporated herein by reference. Arduengo et al., disclose preparation of imidazoles by use of a glyoxal, ammonium carbonate or bicarbonate and a primary amine. Certain compounds of the disclosure were prepared in an analogous method to Arduengo et al.; see, for example, FIGS. 1 and 3.

Figure 2:
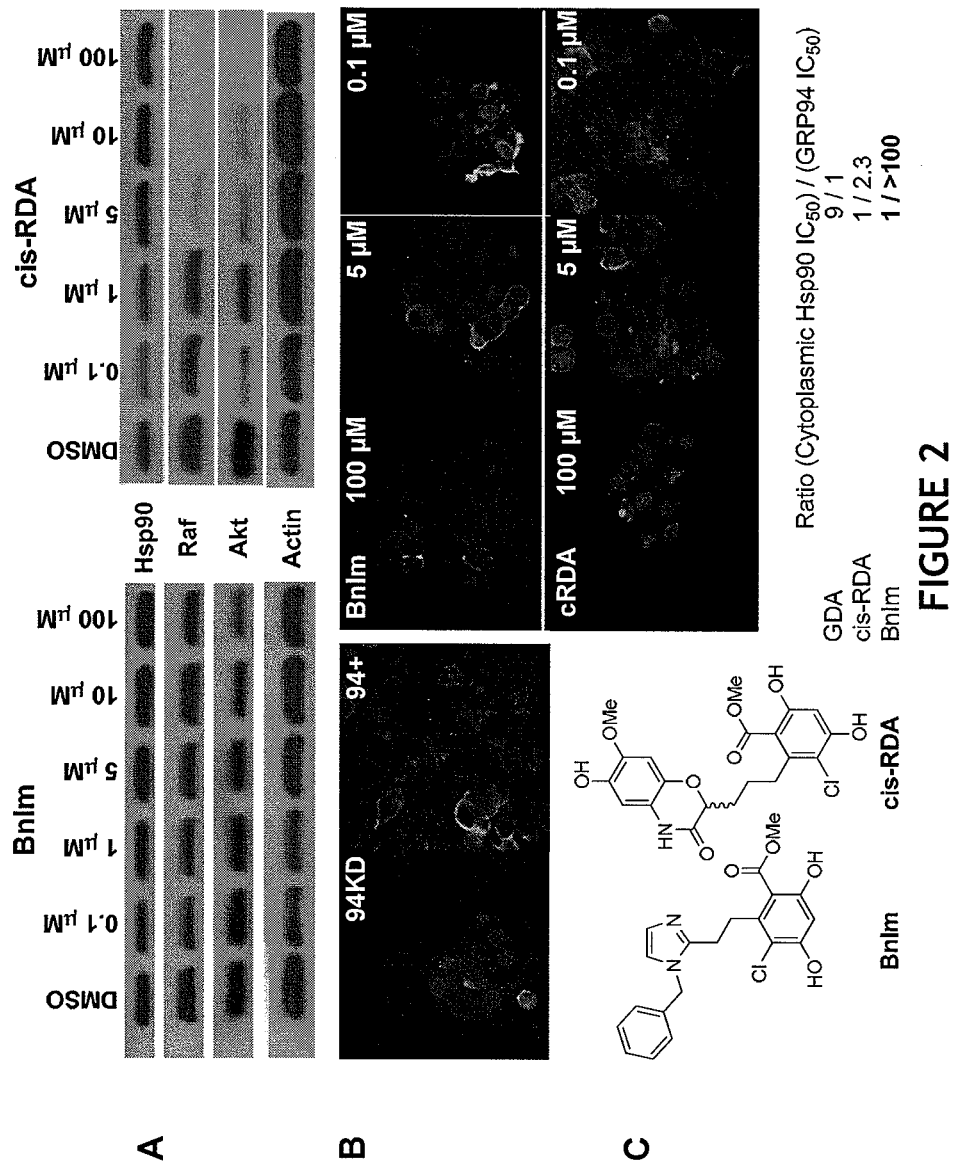
FIG. 2 shows (A) representative Western blots of cytosolic Hsp90 client proteins (Akt and Raf) from HEK293 cells treated with either BnIm (2), or cRDA; and (B) fluorescence microscopy images of HEK293 cells stably transfected with siRNA targeting GRP94(94 kD) or scrambled siRNA (94+). Structures of BnIm and comparative compound cis-radamide (cis-RDA) are illustrated at (C) with comparative ratios of cytoplasmic Hsp90 $IC_{50}$ to GRP94 $IC_{50}$ for each compound as described in Example 3.

Upon the preparation of 2, biological studies were pursued to validate the hypothesis that 2 was an isoform-selective inhibitor of Grp94. Since Toll-like receptors are isoform-dependent upon Grp94 for conformational maturation and localization, a functional assay was developed. In human embryonic kidney cells (HEK293) that were transfected to express Toll, the *Drosophila melanogaster* homologue of the human interleukin-1 receptor, which is of the same superfamily as the human TLR2 and TLR4 receptors [O'Neill, STKE, 2000], siRNA knockdown of Grp94 prohibited Toll receptor trafficking to the cell surface as observed by fluorescence microscopy (FIG. 2). Thus, we proposed that a similar effect would be observed upon Grp94 inhibition. In a similar fashion, the Toll-transfected HEK293 cells were treated with compound 2 for 24 hours after transfection. As can be seen in FIG. 2, Toll trafficking to the cell membrane was inhibited by compound 2 in a dose dependent manner.

Effect on Trafficking of a Toll-Like Receptor.

Upon preparation of 1-5, biological studies commenced to validate our hypothesis that imidazoles containing a phenyl moiety provide Grp94 inhibition. Unlike cytosolic Hsp90 inhibitors that exhibit anti-proliferative effects, RNAi experiments have shown that in culture, cell viability is unhampered by knockdown of Grp94.[47] Thus, a functional assay was necessary to determine Grp94 inhibition.

Grp94 is required for the functional maturation and trafficking of select TLRs.[34,47] Therefore, TLR dependence upon Grp94 was utilized to develop an assay to quantify Grp94 inhibition. As proof of concept, HEK293 cells were stably transfected to express Grp94 directed or scrambled shRNA. Both cell lines were then transfected with a plasmid encoding expression of the Toll protein, the *Drosophila* homologue of the interleukin 1 receptor and the founding member of the TLR family. Grp94 knockdown prevented presentation of the Toll receptor at the cell surface (FIG. 8A) as indicated by immunostaining and fluorescence microscopy. In order to investigate this inhibition of trafficking, cells were permeabilized with Triton X to effect intracellular staining for Toll. Results clearly indicated that the Toll receptor was expressed in the absence of Grp94, but unable to be trafficked to the cell membrane. Western blot analyses of lysates from Grp94 knockdown cells indicated a difference in the glycosylation pattern of the Toll protein, consistent with ER-retention and providing evidence for impaired trafficking to the cell membrane (FIG. 8B).[48-51] This may indicate that Grp94 interacts with a chaperone or partner protein that is involved in the glycosylation of its clients.

Figure 8:
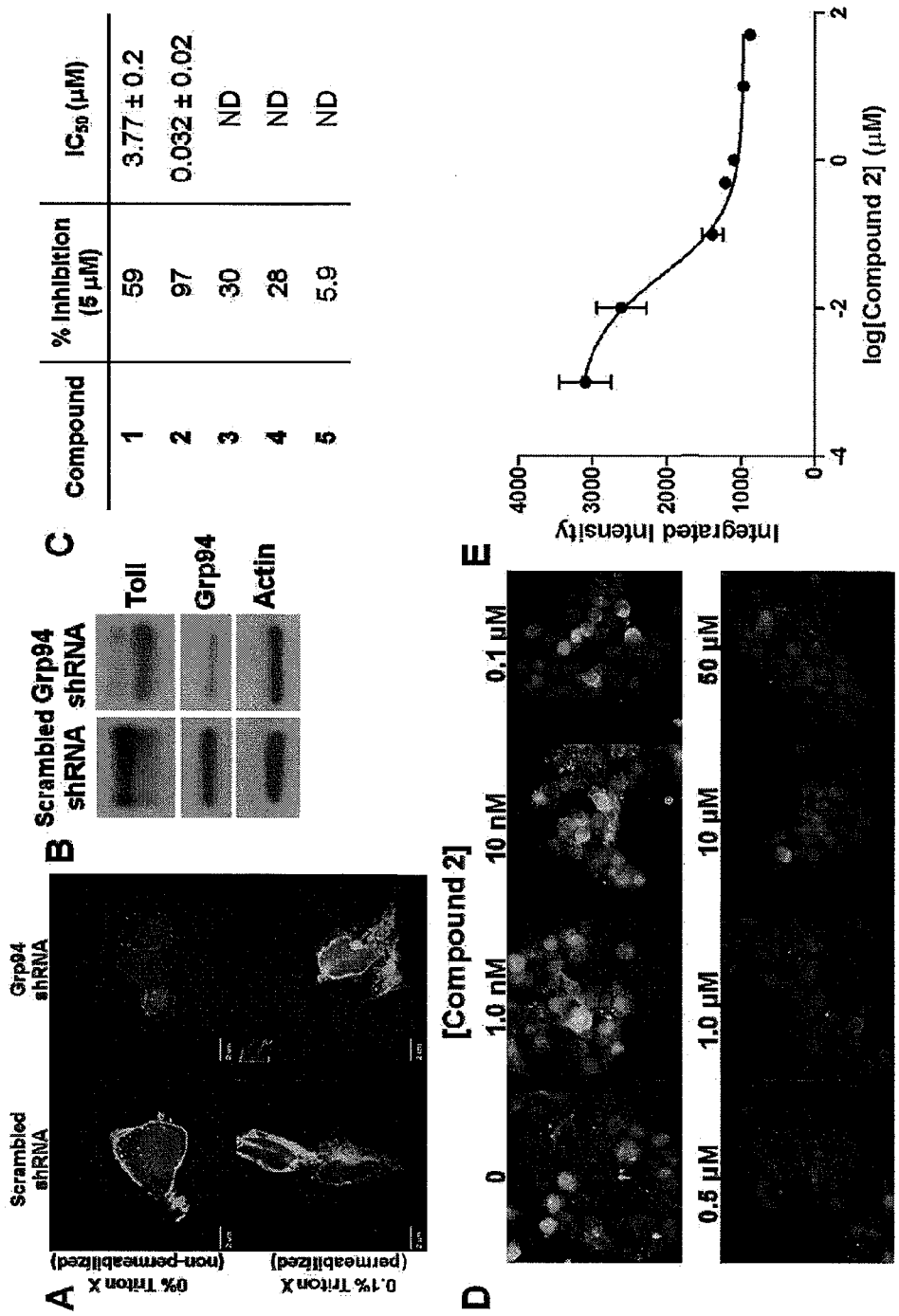
FIG. 8 shows representative fluorescence confocal microscopy images of HEK293 cells stably transfected to produce either scrambled shRNA or Grp94-targeted shRNA and transfected to express the Toll receptor (green) (blue=DAPI, 100×TIRF oil immersion (A); Western blot analysis of cells treated as in A (B); Table of activities for compounds 1-5 to inhibit the trafficking of toll (error bars=+/−SEM for at least 100 different cell populations (C); Representative epifluorescence microscopy images of HEK293 cells transfected to express the Toll receptor (green) and then treated with increasing concentration of compound 2 for 24 h. prior to staining (blue=DAPI, 60×, air objective, (D); and dose-response curve for Toll-trafficking inhibition of compound 2 (E).

Once functional knockdown of Grp94 was established, and a reduced cell surface expression of Toll observed, this assay served as readout for Grp94 inhibition. HEK293 cells were transfected with the same Toll-expressing plasmid, and subsequently exposed to compounds 1-5 for 24 h prior to surface staining. The extent of surface expression was then quantified by measuring fluorescence intensity at the cell surface with Cell Profiler.[52] A dose-response curve for each of the compounds that inhibited at least 50% of Toll trafficking at 5 μM was generated to obtain $IC_{50}$ values (FIG. 8C). Representative fluorescent microscopic images and a dose-response curve are shown for compound 2 in FIG. 8. Interestingly, the observed $IC_{50}$ values for this series of compounds correlated well with the increased binding affinities predicted by Surflex docking scores, supporting our proposed mode of binding. To ensure that compound 2 demonstrates selectivity for Grp94 versus cytosolic Hsp90 (Hsp90α and Hsp90β), we investigated the effect of compound 2 on both cell proliferation and the stability of Hsp90-obligate clients, two well-established methods for the evaluation of Hsp90α/β inhibitors.

In parallel, compound 2 was evaluated for its inhibitory efficiency of cytosolic Hsp90 via Western blot analyses. As shown in FIG. 2, compound 2 showed minimal effect on the concentrations of Raf and Akt, both client proteins of cytosolic Hsp90, at concentrations as high as 100 μM. In contrast, cRDA, which exhibits minimal selectivity for Grp94 in the Toll-trafficking assay, displayed client protein degradation at ~1 μM, a value mimicking its observed $IC_{50}$ in MCF7 and SkBR3 cell lines.

Figure 5:
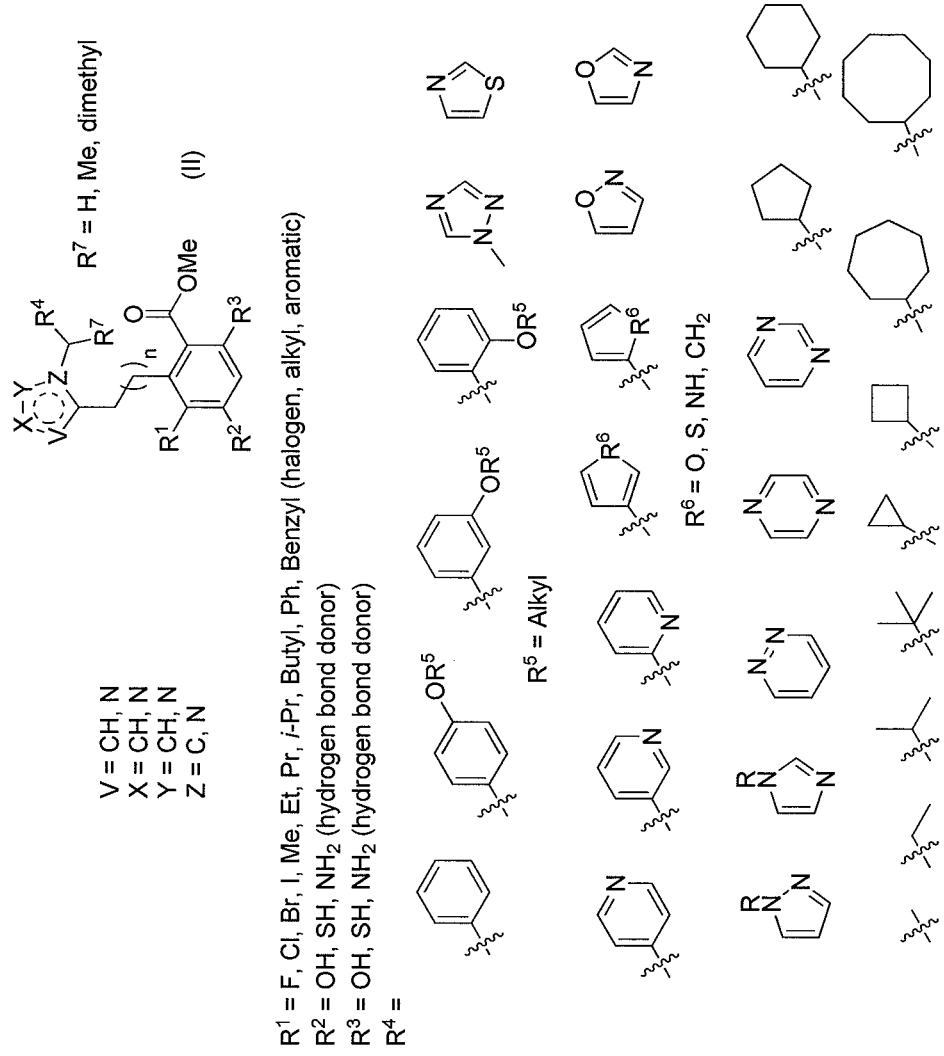
FIG. 5 shows a generic series of compounds designed for selective GRP94 inhibition.

Consistent with the molecular modeling predictions, the first compound synthesized, BnIm, 2, exhibits ~100:1 selectivity for GRP94 versus cytoplasmic Hsp90 α/β, as determined by inhibition of GRP94-mediated Toll presentation at the cell surface versus western blot analysis of Hsp90-dependent proteins found in the cytoplasm (See FIG. 2). As disclosed in FIG. 5 and Example 1, modification of the aryl side chain has been performed to enhance interactions with the GRP94 binding site.

Inhibition of IGF-II Secretion by 2.

Figure 9:
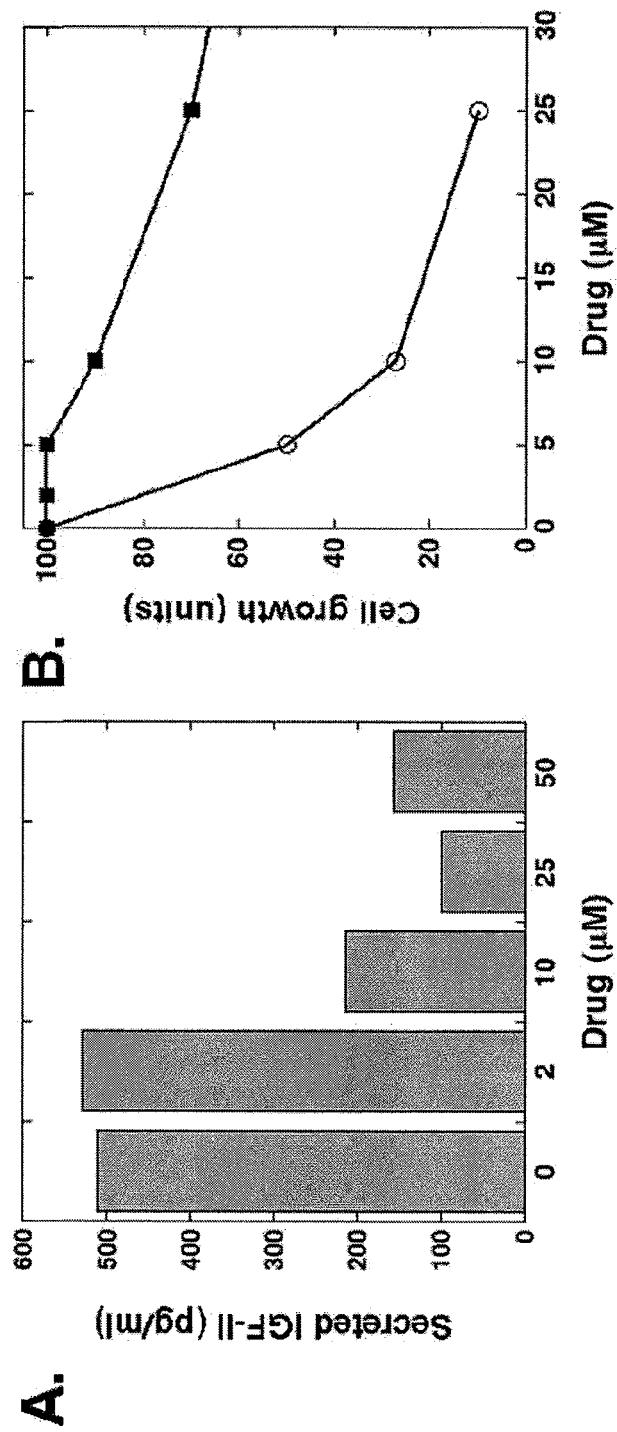
FIG. 9 shows inhibition of IFG-II secretion by compound 2. (A). C2C12 cells were induced to differentiate by serum-starvation in the presence of the indicated concentrations of 2. Supernatants were collected 48 h. later and IFG-II levels measured by ELISA. Drug, concentration range of 2. (B). Toxicity of compound 2 (■) and RDC (●) against C2C12 cells. The viability of cells treated as in A was measured at each of the indicated concentrations by the XTT assay.

IGF-II is a second well-defined Grp94-dependent client protein and active Grp94 is required for the secretion of IGF-11 (Ostrovsky et al., 2009). It has been previously demonstrated that pan-Hsp90 inhibitors, such as 17-AAG, prevent the secretion of IGF-II in serum-starved C2C12 myoblast cells.[28,53-54] Accordingly, serum-starved C2C12 cells were treated with increasing concentrations of compound 2 and the secretion of IGF-II was measured by ELISA (FIG. 9A). Approximately 60% reduction of IGF-II was observed already at 10 µM of 2, while little effect on cell viability was observed (FIG. 9B). The effect on IGF-II secretion is consistent with previous observations using pan-Hsp90 inhibitors, while the lack of effect on cell viability by 2 indicates that this compound is working through a Grp94-dependent mechanism and does not exhibit pan-inhibition.

Effect on Grp94 Conformation.

Figure 10:
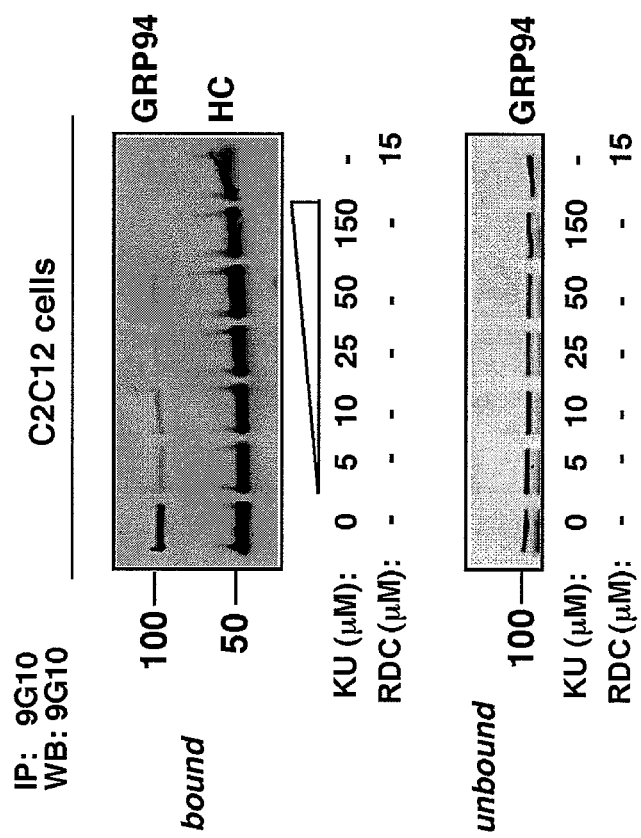
FIG. 10 shows C2C12 cells were treated with the indicated concentrations of 2 or RDC overnight and cell lysates were immunoprecipitated with the conformation-specific antibody 9G10 and subsequently were immunoblotted for Grp94; lower panel, immunoblot of whole cell lyates with 9G10; HC=heavy chain; N=3.

Prior studies have shown that occupation of the Grp94 N-terminal ATP binding pocket by inhibitors results in an altered conformation of this domain.[55-56] Anti-Grp94 (9G10) is an antibody that recognizes the acidic region (residues 290-350) in the second domain of Grp94.[57] Occupation of the ATP binding site causes a conformational switch in this region and prevents the 9G10 antibody from recognizing Grp94.[56] Therefore, lysates of C2C12 cells treated with increasing concentrations of compound 2 were immunoprecipitated to assess whether it induces a conformational switch in Grp94. As observed in FIG. 10, compound 2 induces a conformational switch in Grp94, as the 9G10 antibody is unable to recognize and immunoprecipitate the Grp94 in cells treated with 2. This result parallels the IGF-II secretion data shown in FIG. 9, suggesting that an alteration in Grp94 conformation is incompatible with IGF-II secretion. Interestingly, this activity of Grp94 inhibitors appears to be cell-specific, as analogous experiments performed in CHO cells failed to show an effect on the conformation of Grp94 (data not shown).

Hsp90 α/β Inhibitory Activity.

Figure 11:
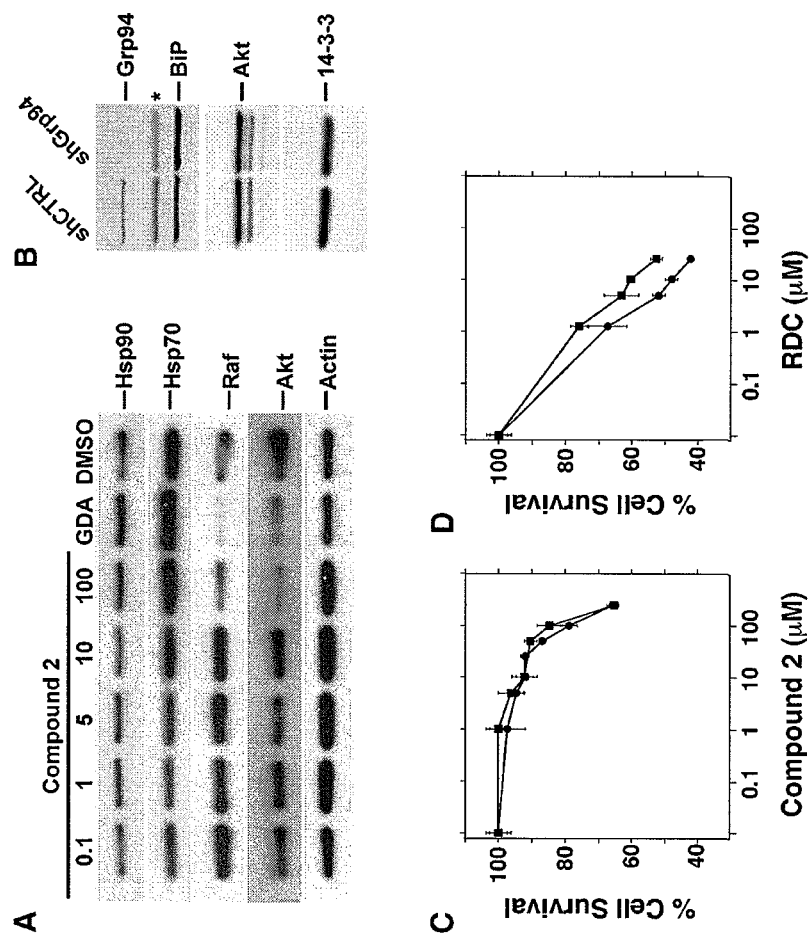
FIG. 11 shows Western blot analysis of HEK293 cell lysates (7.5 μg total protein) after treatment with indicated concentration of compound 2 (μM) for 24 hr. GDA, a known pan-Hsp90 inhibitor is shown as a positive control (500 nM), while actin is shown as a negative, loading control (A); Lysates of HeLa cells stably expressing either scramble shRNA (shCTRL) or GRP94-targeting shRNA (shGRP94) were analyzed by immunoblotting. GRP94 and BiP were detected by the anti-KDEL antibody. *, an unknown KDEL-containing band. 14-3-3 served as loading control (B); HeLa cells as in B) were exposed for 48 hrs at the indicated concentration of compound 2 (C) or RDC (D). Cell survival was measured by XTT assay (n=4).

As previously mentioned, it has been shown that Grp94 is not essential for tissue culture cell viability.[28] In contrast, loss of functional Hsp90α or Hsp90β results in cell death. Therefore, we investigated the anti-proliferative effects of compounds 1-5 against two breast cancer cells, MCF7 (ER+) and SKBR3 (Her2 overexpressing, ER—), and against the non-transformed HEK293 cells. None of the compounds evaluated manifested anti-proliferative activity at 100 µM, indicating these compounds do not target Hsp90α or Hsp90β. To support these findings, western blot analyses of Hsp90α/β client proteins were performed from HEK293 cell lysates. Prototypical pan-Hsp90 inhibitors induce proteasome-mediated degradation of Hsp90α/β client substrates.[6] As shown in FIG. 11, compound 2 does not induce the degradation of Raf or Akt, two well-documented Hsp90α/β-dependent client proteins until 100 µM concentration (see also FIG. 8).[58-60] At this concentration, induction of HSP70, similar to the one induced by GDA, is presumably mediated by targeting of cytosolic Hsp90. As shown in FIG. 7B, The effect on Akt cannot be attributed to ablation of GRP94.

We also tested the cytotoxicity of compound 2 in cells that are either GRP94-sufficient or -deficient and compared it to the cytotoxicity of RDC. As shown in FIG. 7C-D, compound 2 is much less toxic: the IC50 for HeLa cell viability is >250 µM, while RDC already reaches this level at 8 µM. In either case, the cytotoxicity is not attributable to inhibition of GRP94, because cells responded equally regardless of the presence of GRP94 (FIG. 7C-D). Similar results were obtained with other cell lines (e.g. C2C12 in FIG. 6).

Remarkably, at the lower concentration range Compound 2 inhibits the presentation of the Grp94-dependent Toll receptor at approximately 30 nM and does not affect cytoplasmic proteins until 100 µM in HEK293 cells, exhibiting Grp94 selective inhibition.

Induction of BiP Expression.

Figure 12:
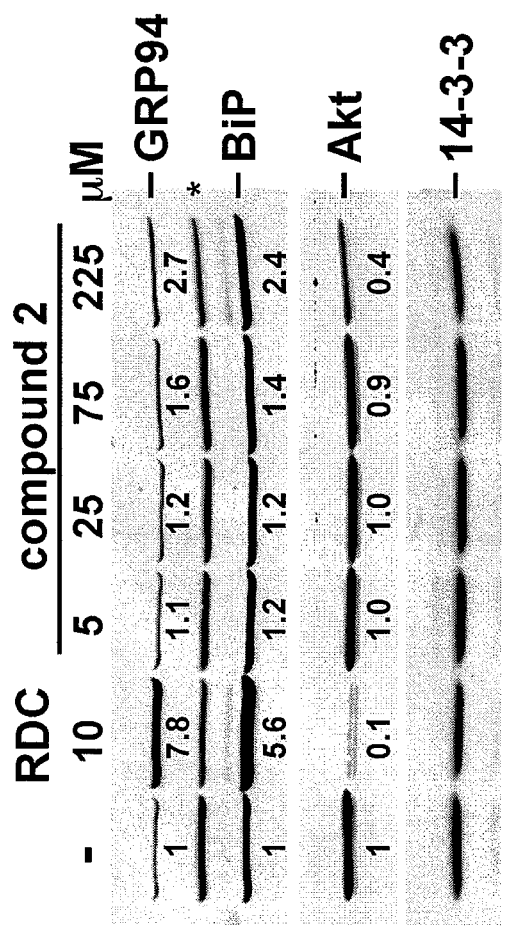
FIG. 12 shows induction of BiP Expression by treatment with 2. NIH-3T3 cells were treated with 25 μM of 17-AAG (AAG), 10 μM of RDC or 0-50 μM of 2. After 18 hrs cells were harvested for SDS-PAGE and analyzed by immunoblotting. Grp94, BiP and PDIA6 were detected with the monoclonal anti-KDEL antibody, AKT by rabbit anti-serum. 14-3-3 served as loading control. Numbers below BiP, Grp94, and AKT bands are the relative expression levels, determined by densitometry.

Inhibition of Hsp90 is also known to induce expression of Hsp70 and this response is useful as a diagnostic tool (FIG. 11).[61-62] A parallel response exists when Grp94 expression is ablated by RNAi, or when its activity is inhibited by RDC or 17-AAG: a transcriptional response is initiated that leads to upregulation of expression of BiP, the ER member of the Hsp70 family (Eletto et al., submitted). We therefore assessed the ability of 2 to cause BiP up-regulation, in comparison to pan-Hsp90 inhibitors. As shown in FIG. 12, treatment of C2C12 cells with 0-75 µM of compound 2 did not lead to up-regulation of BiP, while treatments with 10 µM Rad (or 25 µM of 17-AAG, data not shown) did cause BiP up-regulation. Only at concentrations above 200 µM did compound 2 resemble RDC and induce BiP expression. However, at these concentrations, the compound also destabilized Akt, a hallmark of inhibition of cytosolic Hsp90 (FIG. 12). The inability of 2 to upregulate BiP at the 0-75 µM concentration range was surprising, because this transcriptional response was shown to be a property of Grp94 ablation and not Hsp90 (Eletto et al., submitted).

Effect on *Drosophila* Development.

Figure 13:
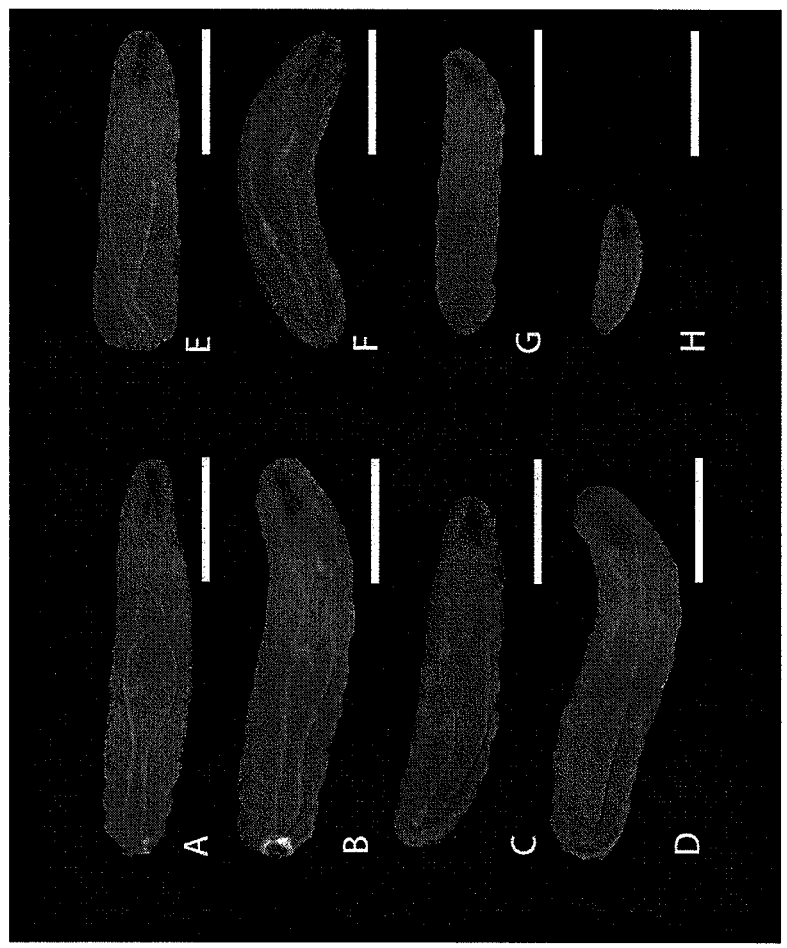
FIG. 13 shows dose-response effect of increasing concentrations of compound 2 on suppression of *Drosophila* larval growth.

Previous studies have demonstrated that Gp93, the *Drosophila* ortholog of Grp94 is an essential gene.[26] In the *Drosophila* model, maternal Gp93 is sufficient to support embryogenesis in Gp93 homozygous null embryos. In the absence of zygotic expression of Gp93, however, larvae display a pronounced growth defect, commensurate with disrupted gut epithelial morphology, decreased gut nutrient uptake, and marked aberrations in copper cell structure and function. As a consequence, loss of Gp93 expression is larval lethal in *Drosophila*. To determine the effects of compound 2 on *Drosophila* larval growth, first instar wild type (w1118) larvae were placed onto fly food supplemented with either no supplement (A), 0.1% (B), 0.3% (C), or 0.5% (D) DMSO (vehicle controls) or fly food supplemented with 250 µg/ml (E), 500 µg/ml (F), 750 µg/ml (G) or 1 mg/ml (H) compound 2. As is evident from the micrographs of representative larvae, dietary uptake of 2 was associated with a dramatic growth phenotype (FIG. 13). In parallel experiments, larval gut tissue was obtained from each of the feeding conditions and gut epithelial morphology evaluated by fluorescence microscopy. No grossly discernible effects on copper cell structure were observed, indicating that under these feeding conditions, the inhibition of Gp93 function was incomplete (data not shown). Pharmacokinetic studies of compound absorption and metabolism may provide addition insights into this partial phenotypic behavior.

Hsp90 inhibitors have been the subject of intense pharmaceutical research, not only for cancer, but also neurodegeneration. All Hsp90 inhibitors that have reached clinical trials bind to the Hsp90 N-terminal ATP-binding pocket and demonstrate pan-Hsp90 inhibition, i.e. they inhibit all human Hsp90 isoforms simultaneously.[14-15,70] Toxicities and off-target effects resulting from Hsp90 inhibition may be a consequence of pan-inhibition. Therefore, the design of Hsp90 isoform-selective inhibitors may provide a valuable pharmacological tool to dissect the roles of each isoform and may lead to more clinically useful inhibitors.

Comparing the crystal structures of several known Hsp90 inhibitors bound to either cytosolic Hsp90 or to the ER-resident Grp94 provided a rationale design platform for the development of Grp94 inhibitors. Using structure-based drug design, five compounds were identified as potential leads that contain a phenyl ring appended to an imidazole ring, which serves as a cis-amide bioisostere. The predisposed orientation of the phenyl ring was postulated to allow interactions with the unique Grp94 n-rich pocket. Since Grp94 has previously been shown to be responsible for the trafficking of TLRs to the cell membrane,[34] this activity was used as a functional assay for Grp94 inhibition. Of the five compounds evaluated, compound 2 manifested the best activity in this assay (35 nM). In subsequent, direct readout assays, including an in-cell conformational assay, compound 2 affected Grp94 itself at the same concentration as that needed to inhibit chaperone activity.

Once the Grp94 inhibitory activity of compound 2 was established by these parameters, we evaluated the isoform selectivity of the compound. Inhibitors of cytosolic Hsp90 (Hsp90α/β) manifest antiproliferative activity in cell culture. At concentrations wherein the assays observed activity for compound 2, there were no cytotoxic effects against any cell line tested. In addition, compound 2 exhibited no effect on the prototypical Hsp90α/β client kinases, Akt or Raf, until concentrations 100× greater than the $IC_{50}$ for Grp94 inhibition. Therefore, compound 2 appears to manifest considerable selectivity for Grp94 versus Hsp90α/β, perhaps explaining its low toxicity. Lastly, compound 2 stunted the growth of *Drosophila* larvae in a dose-dependent manner, suggesting that it may be a useful Grp4 inhibitor in vivo. Future studies with 2 will help dissect the roles played by Grp94 and will shed light into the validity of Grp94 as a therapeutic target.

The compounds of the disclosure can also be evaluated with respect to antiproliferative and neuroprotective activities by various protocols as known in the art and as disclosed in the accompanying examples. For example, the antiproliferative activities of the compounds can be evaluated against prostate or breast cancer cell lines. More specifically, two distinct human breast cancer cell lines, an estrogen receptor positive cell line, MCF-7, and an estrogen receptor negative, Her2 expressing cell line, SKBr3 can be employed. The in vitro activity of the disclosed compounds can be further evaluated by their growth-inhibitory potency in, e.g., MCF-7 cells. The quantification of cell survival in MCF-7 cells (initially 5000 cells/well of a 96-well plate, exposed after 24 h to serial dilution of the different analogues for 72 h) can be established by using the 3-(4,5-dimethylthiazol-2-yl)-2,5-diphenyltetrazolium bromide assay (MTT, Sigma). The experiment can be conducted as described by LeBras 2007, J. Med. Chem. 2007, 50, 6189, which is incorporated herein by reference. The $IC_{50}$ values can be measured as the drug concentration that inhibits the cell growth by 50% compared with growth of vehicle-treated cells.

Each compound can also be tested for its ability to decrease cellular levels of Her2, an Hsp90-dependent client protein involved with oncogenic signaling pathways in several types of cancers. Protocols are disclosed in Hadden et al., Bioorg. Med. Chem. 2009; 17: 634-640, which is incorporated herein by reference.

Without available small molecule inhibitors, the role of Grp94 in cell culture is largely undetermined. siRNA experiments, however, suggest Grp94 to be necessary for embryonic development, but nonessential for mammalian cell culture viability. Thus, compound 2, was submitted to the National Cancer Institute 60-cell panel (NCI-60) to evaluate the compound's cytotoxicity profile. In accordance with previous siRNA results, compound 2 displayed negligible cytotoxicity across all 60 transformed cell lines, further suggesting Grp94 operation to be nonessential for mammalian cell culture viability. This should not dampen excitement for selective Grp94 inhibitors, as numerous studies have shown 3-dimensional tumor response to be drastically different from cell culture responses. Requisite studies are underway to understand the effect of Grp94 inhibition on 3-dimensional tumor models.

Molecular terms, when used in this application, have their common meaning unless otherwise specified. It should be noted that the alphabetical letters used in the formulas of the present invention should be interpreted as the functional groups, moieties, or substituents as defined herein. Unless otherwise defined, the symbols will have their ordinary and customary meaning to those skilled in the art.

The term "acyl" refers to —COR wherein R used in this definition is hydrogen, alkyl, alkenyl, alkynyl, carbocyclic, heterocylic, aryl, or aralkyl. Most preferably, R is hydrogen, alkyl, aryl, or aralkyl.

The term "amido" indicates either a C-amido group such as —CONR'R" or an N-amido group such as —NR'COR" wherein R' and R" as used in this definition are independently hydrogen, alkyl, alkenyl, alkynyl, alkoxy, carbocyclic, heterocylic, aryl, or aralkyl. A "sulfoamido" group includes the —NR'—SO₂—R". Most preferably, R' and R" are hydrogen, alkyl, aryl, or aralkyl.

The term "amino" signifies a primary, secondary or tertiary amino group of the formula —NR'R" wherein R' and R" as used in this definition are independently hydrogen, alkyl, alkyenyl, alkynyl, aralkyl, carbocyclic, heterocyclic, aralkyl, or other amino (in the case of hydrazide) or R' and R" together with the nitrogen atom to which they are attached, form a ring having 4-8 atoms. Thus, the term "amino", as used herein, includes unsubstituted, monosubstituted (e.g., monoalkylamino or monoarylamino), and disubstituted (e.g., dialkylamino or aralkylamino) amino groups. Amino groups include —NH₂, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain 1 to 12 carbon atoms. Most preferred are "lower alkyl" which refer to an alkyl group of one to six, more preferably one to four, carbon atoms. The alkyl group may be optionally substituted with an amino, alkyl, halo, or hydroxyl group.

The term "alkoxy" denotes oxy-containing groups substituted with an alkyl, or cycloalkyl group. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, isopropoxy, and tert-butoxy groups.

The terms "alkenyl" and "alkynyl" refer to unsaturated aliphatic groups analogous in length and possible substitution to the alkyls described above, but that contain at least one double bond or triple bond respectively.

The term "aryl" means a carbocyclic aromatic system containing one, two or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, indane, and biphenyl. The aryl group may optionally be substituted with an amino, alkyl, halo, hydroxyl, carbocyclic, heterocyclic, or another aryl group.

The term "aralkyl" embraces aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" embraces aryl groups, as defined above, attached to an oxygen atom. The aryloxy groups may optionally be substituted with a halo, hydroxyl, or alkyl group. Examples of such groups include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "aralkoxy" embraces oxy-containing aralkyl groups attached through an oxygen atom to other groups. "Lower aralkoxy" groups are those phenyl groups attached to lower alkoxy group as described above. Examples of such groups include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy.

The term "carboxyl" refers to —R'C(═O)OR", wherein R' and R" as used in this definition are independently hydrogen, alkyl, alkenyl, alkynyl, carbocyclic, heterocyclic, aryl, or aralkyl or R' can additionally be a covalent bond. "Carboxyl" includes both carboxylic acids, and carboxylic acid esters. The term "carboxylic acid" refers to a carboxyl group in which R" is hydrogen. Such acids include formic, acetic, propionic, butryic, valeric acid, 2-methyl propionic acid, oxirane-carboxylic acid, and cyclopropane carboxylic acid. The term "carboxylic acid ester" or "ester" refers to a carboxyl group in which R" is alkyl, alkenyl, alkynyl, carbocyclic, heterocyclic, aryl, or aralkyl.

The term "carbocyclic" refers to a group that contains one or more covalently closed ring structures, and that the atoms forming the backbone of the ring are all carbon atoms. The ring structure may be saturated or unsaturated. The term thus distinguishes carbocyclic from heterocyclic rings in which the ring backbone contains at least one non-carbon atom. The term carbocylic encompasses cycloalkyl ring systems.

The terms "cycloalkane" or "cyclic alkane" or "cycloalkyl" refer to a carbocyclic group in which the ring is a cyclic aliphatic hydrocarbon, for example, a cyclic alkyl group preferably with 3 to 12 ring carbons. "Cycloalkyl" includes, by way of example, cyclopropyl, cyclobutyl, cyclopentyl, cyclohexyl, cycloheptyl, or cyclooctyl, and the like. The cycloalkyl group may be optionally substituted with an amino, alkyl, halo, or hydroxyl group.

The term "ether" refers to the group —R'—O—R" wherein R' and R" as used in this definition are independently hydrogen, alkyl, alkenyl, alkynyl, carbocyclic, heterocyclic, aryl, or aralkyl, and R' can additionally be a covalent bond attached to a carbon.

The terms "halo" or "halogen" refer to fluoro, chloro, bromo or iodo, usually regarding halo substitution for a hydrogen atom in an organic compound.

The term "heterocyclic or heterocycle" means an optionally substituted, saturated or unsaturated, aromatic or non-aromatic cyclic hydrocarbon group with 4 to about 12 carbon atoms, preferably about 5 to about 6, wherein 1 to about 4 carbon atoms are replaced by nitrogen, oxygen or sulfur. Exemplary heterocyclic which are aromatic include groups pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrazolyl. Exemplary heterocycles include benzimidazole, dihydrothiophene, dioxin, dioxane, dioxolane, dithiane, dithiazine, dithiazole, dithiolane, furan, indole, 3-H indazole, 3-H-indole, imidazole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidine, pyridazine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole. The heterocycle may be optionally substituted with an amino, alkyl, alkenyl, alkynyl, halo, hydroxyl, carbocyclic, thio, other heterocyclic, or aryl group. Exemplary heterocyclic groups include 1-pyrrolyl, 2-pyrrolyl, 3-pyrrolyl, 1-indolyl, 2-indolyl, 3-indolyl, 1-pyridyl, 2-pyridyl, 3-pyridyl, 4-pyridyl, 1-imidazolyl, 2-imidazolyl, 3-imidazolyl, 4-imidazolyl, 1-pyrazolyl, 2 pyrazolyl, 3-pyrazolyl, 4-pyrazolyl, 5-pyrazolyl, 1-pyrazinyl, 2-pyrazinyl, 1-pyrimidinyl, 2-pyrimidinyl, 4-pyrimidinyl, 5-pyrimidinyl, 1-pyridazinyl, 2-pyridazinyl, 3-pyridazinyl, 4-pyridizinyl, 1-indolizinyl, 2-indolizinyl, 3-indolizinyl, 4-indolizinyl, 5-indolizinyl, 6-indolizinyl, 7-indolizinyl, 8-indolizinyl, 1-isoindolyl, 2-isoindolyl, 3-isoindolyl, 4-isoindolyl, 5-isoindolyl.

The term "hydroxy" or "hydroxyl" refers to the substituent —OH.

The term "oxo" shall refer to the substituent ═O.

The term "nitro" means —NO$_2$.

The term "sulfanyl" refers to —SR' where R' as used in this definition is hydrogen, alkyl, alkenyl, alkynyl, carbocyclic, heterocyclic, aryl, or aralkyl.

The term "sulfenyl" refers to —SOR' where R' as used is this definition is hydrogen, alkyl, alkenyl, alkynyl, carbocyclic, heterocyclic, aryl, or aralkyl.

The term "sulfonyl" refers to —SOR' where R' as used in this definition is hydrogen, alkyl, alkenyl, alkynyl, carbocyclic, heterocyclic, aryl, or aralkyl.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Also included in the family of compounds of the present invention are the pharmaceutically acceptable salts, esters, and prodrugs thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention be prepared from inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds of by reacting, for example, the appropriate acid or base with the compounds of the present invention.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design, American Pharmaceutical Association and Pergamon Press*, 1987, both of which are incorporated by reference herein.

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier.

The compositions may be formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions.

The term "autoimmune disorder" is intended to include disorders in which the immune system of a subject reacts to autoantigens, such that significant tissue or cell destruction occurs in the subject. The term "autoantigen" is intended to include any antigen of a subject that is recognized by the immune system of the subject. Autoimmune disorders include but are not limited to acute disseminated encephalomyelitis, Addison's disease, Alopecia universalis, ankylosing spondylitisis, antiphospholipid antibody syndrome, aplastic anemia, autoimmune hepatitis autoimmune infertility, autoimmune thyroiditis, autoimmune neutropenia, Behçet's disease, bullous pemphigoid, Chagas' disease, cirrhosis, Coeliac disease, Crohn's disease, Chronic fatigue syndrome, chronic active hepatitis, dense deposit disease, discoid lupus, dermatitis, luten-sensitive enteropathy, dysautonomia, endometriosis, glomerulonephritis, Goodpasture's disease, Graves' disease, Guillain-Barre syndrome, Hashimoto's disease, Hidradenitis suppurativa, idiopathic thrombocytopenia purpura, insulin dependent diabetes mellitus, interstitial cystitis, mixed connective tissue disease, multiple sclerosis, myasthenia gravis, neuromyotonia, opsoclonus myoclonus syndrome, optic neuritis, Ord's thyroiditis, pemphigus vulgaris, pernicious anemia, polyarthritis, polymyositis, primary biliary cirrhosis, psoriasis, Reiter's syndrome, rheumatoid arthritis, sarcoidosis, scleroderma, Sjogren's syndrome, systemic lupus erythematosus, Takayasu's arteritis, temporal arteritis, ulcerative colitis, vitiligo, vulvodynia, warm autoimmune hemolytic anemia, or Wegener's granulomatosis. In a preferred aspect, the autoimmune disorder is multiple sclerosis or its animal model system termed experimental autoimmune encephalomyelitis ("EAE").

The term "neuroprotection" embraces to inhibition of progressive deterioration of neurons that leads to cell disfunction or cell death.

The term "neurodegenerative disorder" embraces a disorder in which progressive loss of neurons occurs either in the peripheral nervous system or in the central nervous system. Examples of neurodegenerative disorders include, but are not limited to chronic neurodegenerative diseases such as diabetic peripheral neuropathy, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis ("ALS"), degenerative ataxias, cortical basal degeneration, ALS-Parkinson's-Dementia complex of Guam, subacute sclerosing panencephalitis, Huntington's disease, Parkinson's disease, multiple sclerosis, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Wernicke-Korsakoffs related dementia (alcohol induced dementia), Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion related diseases (including Creutzfeldt-Jakob, Gerstmann-Straussler-Scheinker disease, Kuru and fatal familial insomnia). Other conditions also included within the methods of the present invention include age-related dementia and other dementias, and conditions with memory loss including vascular dementia, diffuse white matter disease (Binswanger's disease), dementia of endocrine or metabolic origin, dementia of head trauma and diffuse brain damage, dementia pugilistica, and frontal lobe dementia. Also other neurodegenerative disorders resulting from cerebral ischemia or infarction including embolic occlusion and thrombotic occlusion as well as intracranial hemorrhage of any type (including, but not limited to, epidural, subdural, subarachnoid, and intracerebral), and intracranial and intravertebral lesions (including, but not limited to, contusion, penetration, shear, compression, and laceration). Thus, the term also encompasses acute neurodegenerative disorders such as those involving stroke, traumatic brain injury, schizophrenia, peripheral nerve damage, hypoglycemia, spinal cord injury, epilepsy, and anoxia and hypoxia.

In one aspect, the neurodegenerative disorder is selected from Alzheimer's disease, Parkinson's disease, amyotrophic lateral sclerosis, age-related memory loss, senility and age-related dementia, most preferably, the neurodegenerative disorder is Alzheimer's disease. Because, most preferably, the neurodegenerative disorder is Alzheimer's disease, also characterized as an amyloidosis, other conditions within the methods of the present invention include the treatment or prevention of other amyloidosis disorders which share features including, but not limited to, hereditary cerebral angiopathy, normeuropathic hereditary amyloid, Down's syndrome, macroglobulinemia, secondary familial Mediterranean fever, Muckle-Wells syndrome, multiple myeloma, pancreatic- and cardiac-related amyloidosis, chronic hemodialysis arthropathy, and Finnish and Iowa amyloidosis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject lonidamine analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The "patient" or "subject" to be treated with the compounds of the present invention can be any animal, e.g., dogs, cats, mice, monkeys, rats, rabbits, horses, cows, guinea pigs, sheep, and is preferably a mammal, such as a domesticated animal or a livestock animal. In another aspect, the patient is a human.

The term "inhibit" or "inhibiting" refers to a statistically significant and measurable reduction in neurotoxicity, preferably as measured by one or more of the assays discussed herein, preferably a reduction of at least about 10% versus control, more preferably a reduction of about 20%, 30%, 40%, 50% or more, still more preferably a reduction of about 60%, 70%, 80%, 90%, or more.

The term "preventing" as used herein means that the compounds of the present invention are useful when administered to a patient who has not been diagnosed as possibly having the disorder or disease at the time of administration, but who would normally be expected to develop the disorder or disease or be at increased risk for the disorder or disease. The compounds of the invention will slow the development of the disorder or disease symptoms, delay the onset of the disorder or disease, or prevent the individual from developing the disorder or disease at all. Preventing also includes administration of the compounds of the invention to those individuals thought to be predisposed to the disorder or disease due to age, familial history, genetic or chromosomal abnormalities, and/or due to the presence of one or more biological markers for the disorder or disease.

The term "treating," as used herein generally means that the compounds of the invention can be used in humans or animals with at least a tentative diagnosis of the disorder or disease. The compounds of the invention will delay or slow the progression of the disorder or disease thereby giving the individual a more useful life span. The term "treatment" embraces at least an amelioration of the symptoms associated with the disorder or disease in the patient is achieved, where amelioration is used in a broad sense to refer to at least a reduction in the magnitude of a parameter, e.g. symptom, associated with the condition being treated. As such, "treatment" also includes situations where the diseased condition or disorder, or at least symptoms associated therewith, are completely inhibited, e.g. prevented from happening, or stopped, e.g. terminated, such that the patient no longer suffers from the condition or disorder, or at least the symptoms that characterize the condition or disorder.

A "therapeutically effective amount" is an amount of a compound of the present invention or a combination of two or more such compounds, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient and condition, a therapeutically effective amount can be determined by methods known to those of skill in the art. For example, in reference to the treatment of cancer using the compounds of the present invention, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

For another example, in reference to the treatment of a GRP related disorder that is a neurodegenerative disorder or disease using the compounds of the present invention, a therapeutically effective amount refers to that amount which has the effect of (1) slowing (that is, slowing to some extent, preferably stopping) the progression of neurodegeneration in a cell, tissue or subject in need thereof, (2) preventing disease development, and/or, (3) relieving to some extent (or, preferably, eliminating) one or more symptoms associated with neurodegeneration or dementia in a subject in need thereof.

Several of the compounds of the present invention have been shown to inhibit GRP94 in vitro. As such, it is contemplated that therapeutically effective amounts of the compounds of the present invention will be useful as anti-cancer agents and/or neuroprotective agents.

In the context of cancer and neuroprotection, it is contemplated that some of the compounds of the present invention may be used with other GRP94 and/or Hsp90 inhibitors, chemotherapeutic agents, and/or neuroprotective agents.

The following examples are provided to illustrate the present invention and are not intended to limit the scope thereof. Those skilled in the art will readily understand that known variations of the conditions and processes of the following preparative procedures can be used to prepare these compounds.

EXAMPLES

Example 1

Synthesis of GRP94 Inhibitors

General Method for the Synthesis of Compounds 1-5. Aldehyde 6 (1 equiv.) was dissolved in wet MeOH at 25° C. The required aniline/amine (1 equiv.) was added dropwise via a syringe to the reaction flask followed by addition of ammounim bicarbonate (1 equiv.). Glyoxal (1 equiv.) was then added dropwise via a syringe and the reaction was allowed to stir at 25° C. for 8 h. Upon complete conversion of the aldehyde, as observed by thin-layer chromatography, tetrabutylammonium fluoride was added dropwise via syringe and the reaction was allowed to stir at 25° C. for 30 min, at which time, the reaction was quenched with sat. aq. $NH_4Cl$ and extracted with EtOAc. The organic layers were combined, dried over $Na_2SO_4$, and concentrated in vacuo. All compounds were purified via flash chromatography utilizing 95:5 ($CH_2Cl_2$:MeOH) as the eluent. Yields and characterization for all compounds are provided below.

Compound 2, Methyl 2-(2-(1-benzyl-1H-imidazol-2-yl)ethyl)-3-chloro-4,6-dihydroxybenzoate, BnIm

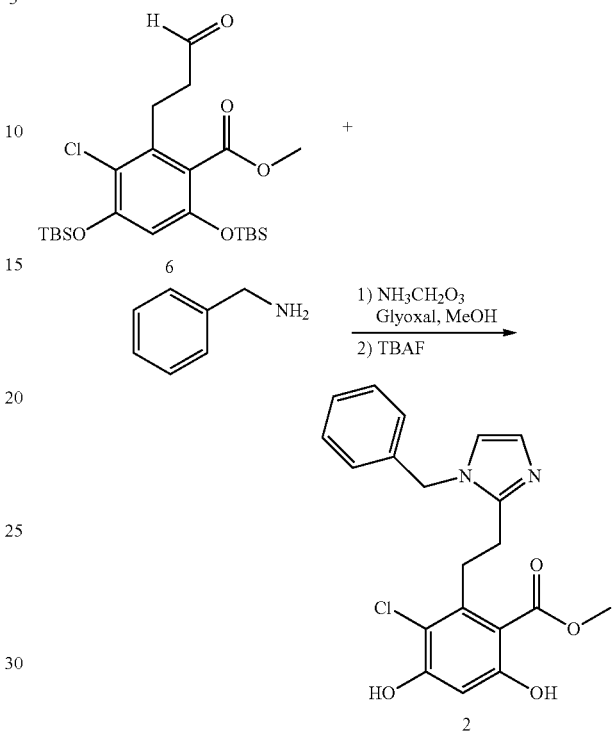

As shown in FIG. 1C, the resorcinol 6 can be treated with benzyl amine, glyoxal, and ammonium bicarbonate, followed by deprotection of the silyl groups with tetrabutylammonium fluoride (TBAF), to produce the title compound in acceptable yield. Methyl 2-(2-(1-benzyl-1H-imidazol-2-yl)ethyl)-3-chloro-4,6-dihydroxybenzoate, 2. $^1$H NMR (CDCl$_3$, 400 MHz) δ 11.74 (bs, 1H), 7.37-7.29 (m, 3H), 7.09-7.07 (m, 3H), 6.88 (d, J=1.4, 1H), 6.52 (s, 1H), 5.14 (s, 2H), 3.85 (s, 3H), 3.60-3.47 (m, 2H), 3.08-2.95 (m, 2H); $^{13}$C NMR (CDCl$_3$, 100 MHz) δ 171.0, 162.8, 159.6, 147.8, 141.2, 135.9, 129.1 (2C), 128.2, 126.7 (2C), 126.1, 120.3, 115.5, 105.0, 102.7, 52.6, 49.7, 30.9, 26.0; ESI-HRMS m/z 385.0953 (M-H, $C_{20}H_{19}ClN_2O_4$ requires 385.0955).

The following compounds were also prepared.

Methyl 3-chloro-2-(2-(1-cyclohexyl-1H-imidazol-2-yl)ethyl)-4,6-dihydroxybenzoate ESI-HRMS m/z 377.1270 (M-H, $C_{19}H_{23}ClN_2O_4$ requires 377.1268).

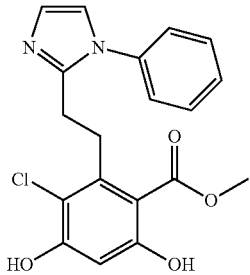 [SMILES: COC(=O)c1c(O)cc(O)c(Cl)c1CCc1nccn1-c1ccccc1]

Compound 1

Methyl 3-chloro-4,6-dihydroxy-2-(2-(1-phenyl-1H-imidazol-2-yl)ethyl)benzoate $^1$H NMR (CDCl$_3$, 400 MHz) δ 7.56-7.39 (m, 3H), 7.32 (d, J=6.8, 2H), 7.14 (s, 1H), 7.05 (d, J=1.0, 1H), 6.51 (s, 1H), 3.84 (s, 3H), 3.50-3.42 (m, 2H), 3.06-2.97 (m, 2H); $^{13}$C NMR (CDCl$_3$, 100 MHz) δ 171.0, 162.9, 158.2, 147.7, 141.4, 137.4, 129.6 (2C), 128.7, 127.0, 126.1 (2C), 121.1, 114.9, 105.7, 102.6, 52.53, 31.15, 26.20; ESI-HRMS m/z 371.0797 (M-H, $C_{19}H_{16}ClN_2O_4$ requires 371.0799).

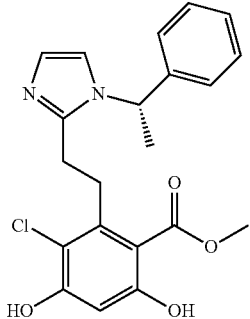 [SMILES: COC(=O)c1c(O)cc(O)c(Cl)c1CCc1nccn1[C@@H](C)c1ccccc1]

(S)-Methyl 3-chloro-4,6-dihydroxy-2-(2-(1-(1-phenylethyl)-1H-imidazol-2-yl)ethyl)benzoate $^1$H NMR (CDCl$_3$, 400 MHz) δ 7.28-7.17 (m, 3H), 7.01 (dd, J=1.4, 1H), 6.97 (m, 3H), 6.42 (s, 1H), 5.36 (q, J=7.0, 1H), 3.71 (s, 3H), 3.42 (m, 2H), 2.84 (t, J=8.2, 2H), 1.74 (d, J=7.0, 3H); $^{13}$C NMR (CDCl$_3$, 100 MHz) δ 171.0, 162.8, 159.0, 147.5, 141.5, 141.4, 129.0 (2C), 127.9, 126.2, 125.6 (2C), 116.7, 115.3, 105.3, 102.7, 54.8, 52.5, 30.7, 26.2, 22.5; ESI-HRMS m/z 399.111 (M-H, $C_{21}H_{21}ClN_2O_4$ requires 399.1112).

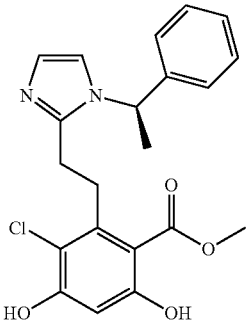

(R)-Methyl 3-chloro-4,6-dihydroxy-2-(2-(1-(1-phenylethyl)-1H-imidazol-2-yl)ethyl)benzoate $^1$H NMR (CDCl$_3$, 400 MHz) δ 7.28-7.17 (m, 3H), 7.01 (dd, J=1.4, 1H), 6.97 (m, 3H), 6.42 (s, 1H), 5.36 (q, J=7.0, 1H), 3.71 (s, 3H), 3.42 (m, 2H), 2.84 (t, J=8.2, 2H), 1.74 (d, J=7.0, 3H); $^{13}$C NMR (CDCl$_3$, 100 MHz) δ 171.0, 162.8, 159.0, 147.5, 141.5, 141.4, 129.0 (2C), 127.9, 126.2, 125.6 (2C), 116.7, 115.3, 105.3, 102.7, 54.8, 52.5, 30.7, 26.2, 22.5; ESI-HRMS m/z 399.111 (M-H, $C_{21}H_{21}ClN_2O_4$ requires 399.1112).

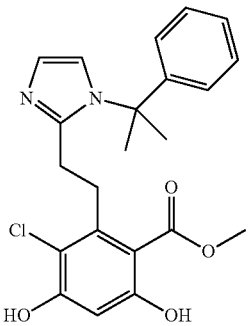 [SMILES: COC(=O)c1c(O)cc(O)c(Cl)c1CCc1nccn1C(C)(C)c1ccccc1]

Methyl 3-chloro-4,6-dihydroxy-2-(2-(1-(2-phenylpropan-2-yl)-1H-imidazol-2-yl)ethyl)benzoate: ESI-HRMS m/z 413.1266 (M-H, $C_{22}H_{23}ClN_2O_4$ requires 413.1268).

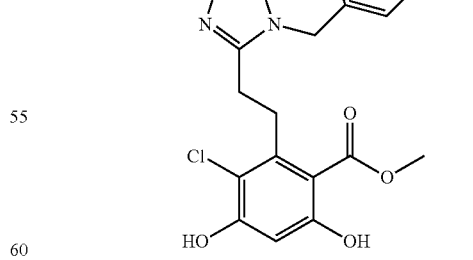

Methyl 3-chloro-4,6-dihydroxy-2-(2-(1-(4-methoxybenzyl)-1H-imidazol-2-yl)ethyl)benzoate $^1$H NMR (CDCl$_3$, 400 MHz) δ 7.19 (m, 3H), 7.10 (d, J=1.3, 1H), 6.93 (m, 2H), 6.64 (s, 1H), 5.22 (s, 2H), 3.89 (s, 3H), 3.79

(s, 3H), 3.52 (dd, J=9.0, 7.0, 2H), 3.10 (m, 2H); $^{13}$C NMR (CDCl$_3$, 100 MHz) δ 171.2, 162.2, 160.6, 158.9, 147.5, 141.6, 129.7 (2C), 128.8, 123.9, 121.7, 115.1 (2C), 115.0, 108.2, 103.6, 55.6, 53.1, 50.1, 31.0, 26.1; ESI-HRMS m/z 415.1061 (M-H, C$_{21}$H$_{21}$ClN$_2$O$_5$ requires 415.1061).

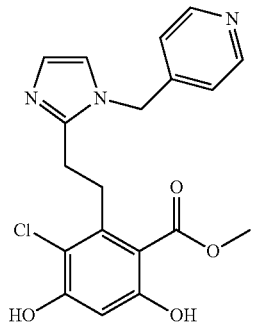 [SMILES: COC(=O)c1c(O)cc(O)c(Cl)c1CCc1nccn1Cc1ccncc1]

Methyl 3-chloro-4,6-dihydroxy-2-(2-(1-(pyridin-4-ylmethyl)-1H-imidazol-2-yl)ethyl)benzoate $^1$H NMR (CDCl$_3$, 400 MHz) δ 8.58 (dd, J=4.5, 1.5, 2H), 7.13 (d, J=1.4, 1H), 6.96 (d, J=6.0, 2H), 6.92 (d, J=1.4, 1H), 6.47 (s, 1H), 5.19 (s, 2H), 3.89 (s, 3H), 3.55-3.44 (m, 2H), 2.99-2.89 (m, 2H); $^{13}$C NMR (CDCl$_3$, 100 MHz) δ 170.1, 162.5, 159.3, 150.1 (2C), 148.0, 145.8, 141.2, 127.2, 121.3 (2C), 120.3, 115.3, 105.4, 102.8, 52.6, 48.4, 31.0, 26.0; ESI-HRMS m/z 386.0912 (M-H, C$_{19}$H$_{18}$ClN$_3$O$_4$ requires 386.0908).

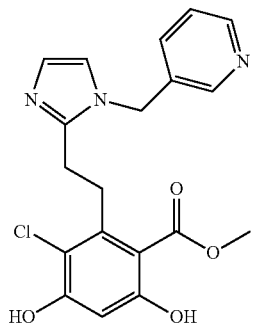 [SMILES: COC(=O)c1c(O)cc(O)c(Cl)c1CCc1nccn1Cc1cccnc1]

Methyl 3-chloro-4,6-dihydroxy-2-(2-(1-(pyridin-3-ylmethyl)-1H-imidazol-2-yl)ethyl)benzoate $^1$H NMR (CDCl$_3$, 400 MHz) δ 8.59 (dd, J=4.6, 1.7, 1H), 8.51 (d, J=1.4, 1H), 7.40-7.30 (m, 2H), 7.11 (d, J=1.3, 1H), 6.92 (d, J=1.3, 1H), 6.50 (s, 1H), 5.20 (s, 2H), 3.90 (s, 3H), 3.58-3.49 (m, 2H), 3.01-2.92 (m, 2H); $^{13}$C NMR (CDCl$_3$, 100 MHz) δ 170.5, 162.5, 158.8, 149.4, 148.0, 147.7, 141.4, 134.6, 132.1, 127.3, 124.1, 120.0, 115.1, 105.6, 102.9, 52.6, 47.1, 31.1, 26.1; ESI-HRMS m/z 386.0903 (M-H, C$_{19}$H$_{18}$ClN$_3$O$_4$ requires 386.0908).

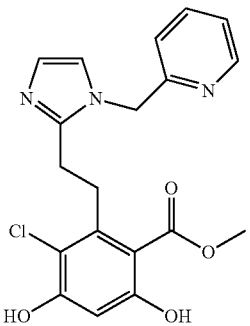 [SMILES: COC(=O)c1c(O)cc(O)c(Cl)c1CCc1nccn1Cc1ccccn1]

Methyl 3-chloro-4,6-dihydroxy-2-(2-(1-(pyridin-2-ylmethyl)-1H-imidazol-2-yl)ethyl)benzoate $^1$H NMR (CDCl$_3$, 400 MHz) δ 8.61 (d, J=4.5, 1H), 7.69 (td, J=7.7, 1.7, 1H), 7.26 (dd, J=7.3, 5.2, 1H), 7.11 (d, J=1.3, 1H), 6.98 (d, J=1.3, 1H), 6.85 (d, J=7.9, 1H), 6.49 (s, 1H), 5.29 (s, 2H), 3.88 (s, 3H), 3.58-3.45 (m, 2H), 3.06-2.91 (m, 2H); $^{13}$C NMR (CDCl$_3$, 100 MHz) δ 170.8, 162.7, 158.6, 156.0, 149.7, 147.9, 141.3, 137.5, 127.0, 123.0, 120.7, 120.2, 115.1, 105.6, 102.8, 52.6, 51.2, 30.9, 26.0; ESI-HRMS m/z 386.0899 (M-H, C$_{19}$H$_{18}$ClN$_3$O$_4$ requires 386.0908).

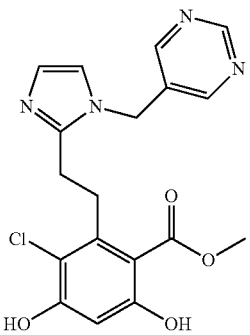 [SMILES: COC(=O)c1c(O)cc(O)c(Cl)c1CCc1nccn1Cc1cncnc1]

Methyl 3-chloro-4,6-dihydroxy-2-(2-(1-(pyrimidin-5-ylmethyl)-1H-imidazol-2-yl)ethyl)benzoate $^1$H NMR (CDCl$_3$, 400 MHz) δ 9.19 (s, 1H), 8.54 (s, 2H), 7.11 (d, J=1.4, 1H), 6.91 (d, J=1.4, 1H), 6.48 (s, 1H), 5.20 (s, 2H), 3.89 (s, 3H), 3.55-3.44 (m, 2H), 3.02-2.92 (m, 2H); $^{13}$C NMR (CDCl$_3$, 100 MHz) δ 169.1, 161.4, 157.6, 157.5, 154.4 (2C), 146.7, 140.1, 128.9, 126.6, 118.7, 114.0, 104.8, 102.0, 51.6, 44.0, 30.1, 25.1; ESI-HRMS m/z 387.0861 (M-H, C$_{18}$H$_{17}$ClN$_4$O$_4$ requires 387.0860).

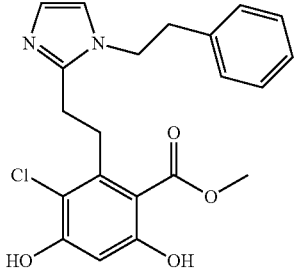 [SMILES: COC(=O)c1c(O)cc(O)c(Cl)c1CCc1nccn1CCc1ccccc1]

Compound 3. Methyl 3-chloro-4,6-dihydroxy-2-(2-(1-phenethyl-1H-imidazol-2-yl)ethyl)benzoate $^1$H NMR (CDCl$_3$, 400 MHz) δ 7.35-7.22 (m, 3H), 7.07 (d, J=6.9, 2H), 7.01 (s, 1H), 6.82 (s, 1H), 6.48 (s, 1H), 4.16 (t, J=7.1, 2H), 3.90 (s, 3H), 3.53-3.40 (m, 2H), 3.04 (t, J=7.1, 2H), 2.85-2.72 (m, 2H); $^{13}$C NMR (CDCl$_3$, 100 MHz) δ 170.8, 162.8, 158.5, 147.3, 141.4, 137.2, 128.9 (2C), 128.7 (2C), 127.1, 126.4, 119.1, 115.0, 105.6, 102.7, 52.6, 47.4, 37.6, 30.8, 25.8; ESI-HRMS m/z 399.1115 (M-H, C$_{21}$H$_{20}$ClN$_2$O$_4$ requires 399.1112).

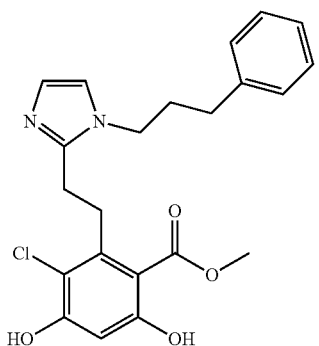 [SMILES: COC(=O)c1c(O)cc(O)c(Cl)c1CCc1nccn1CCCc1ccccc1]

Compound 4

Methyl 3-chloro-4,6-dihydroxy-2-(2-(1-(3-phenylpropyl)-1H-imidazol-2-yl)ethyl)benzoate $^1$H NMR (CDCl$_3$, 400 MHz) δ 7.32-7.11 (m, 5H), 7.04 (s, 1H), 6.89 (s, 1H), 6.51 (s, 1H), 4.02-3.81 (m, 5H), 3.63-3.44 (m, 2H), 3.06-2.91 (m, 2H), 2.68 (t, J=7.6, 2H), 2.22-2.04 (m, 2H); $^{13}$C NMR (CDCl$_3$, 100 MHz) δ 170.9, 162.8, 159.3, 147.2, 141.3, 140.2, 128.7 (2C), 128.3 (2C), 126.4, 126.2, 119.1, 115.4, 105.2, 102.8, 52.6, 45.3, 32.7, 32.2, 30.9, 25.9; ESI-HRMS m/z 413.1272 (M-H, C$_{22}$H$_{23}$ClN$_2$O$_4$ requires 413.1268).

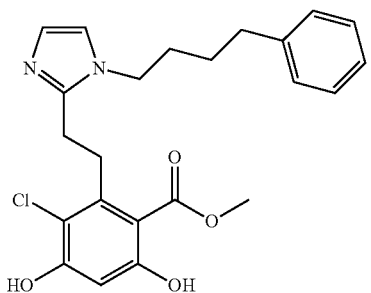 [SMILES: COC(=O)c1c(O)cc(O)c(Cl)c1CCc1nccn1CCCCc1ccccc1]

Compound 5

Methyl 3-chloro-4,6-dihydroxy-2-(2-(1-(4-phenylbutyl)-1H-imidazol-2-yl)ethyl)benzoate $^1$H NMR (CDCl$_3$, 400 MHz) δ 7.33-7.13 (m, 1H), 7.02 (d, J=1.1, 1H), 6.85 (d, J=1.2, 1H), 6.51 (s, 1H), 3.97-3.86 (m, 5H), 3.58-3.47 (m, 2H), 3.04-2.94 (m, 2H), 2.67 (t, J=7.4, 2H), 1.80 (dt, J=11.3, 7.1, 2H), 1.68 (dt, J=15, 7.1, 2H); $^{13}$C NMR (CDCl$_3$, 100 MHz) δ 171.0, 162.8, 159.4, 147.1, 141.4, 141.3, 128.5 (2C), 128.4 (2C), 126.1, 125.9, 119.2, 115.4, 105.1, 102.7, 52.6, 46.0, 35.3, 30.8, 30.4, 28.4, 25.9; ESI-HRMS m/z 427.1421 (M-H, C$_{23}$H$_{25}$ClN$_2$O$_4$ requires 427.1425).

Example 2

Cell Culture

HEK293 and C2C12 cells were maintained in DMEM supplemented with non-essential amino acids, L-glutamine (2 mM), streptomycin (500 µg/mL), penicillin (100 units/mL), and 10% FBS. Cells were grown to confluence in a humidified atmosphere (37° C., 5% CO$_2$). Stable GRP94-siRNA knockdown cell lines were generated as follows: the shRNA sequence 5'-GGCUCAAGGACAGAUGAUGtt-3' was cloned into the A pSilencer 2.0-U6 vector (Ambion) and positive clones confirmed by sequencing. The pSilencer 2.0-U6-GRP94 siRNA vector and a control, non-targeting pSilencer 2.0-U6 siRNA vector (scrambled, control) were transfected into HEK293 cells using Lipofectamine 2000 and the manufacturers protocol. Cell cultures were selected thirty six hours post-transfection by addition of 1 microgram/ml puromycin to the media. Puromycin resistant clones (both GRP94 siRNA and non-targeting siRNA) were subsequently expanded and screened for knockdown efficiency by immunoblotting, using GRP94 antibody DU120. Clones displaying greater than 90% knockdown were selected. Puromycin-resistant clones from the non-targeting siRNA were obtained in parallel and screened for normal GRP94 expression, also by immunoblotting with DU120. C2C12 Cells were maintained and induced to differentiate into myoblasts as described in Yaffe, D.; Saxel, O. R. A. Serial passaging and differentiation of myogenic cells isolated from dystrophic mouse muscle. *Nature* 1977, 270, 725-727.

Example 3

Toll Trafficking Assay Protocol

Figure 4:
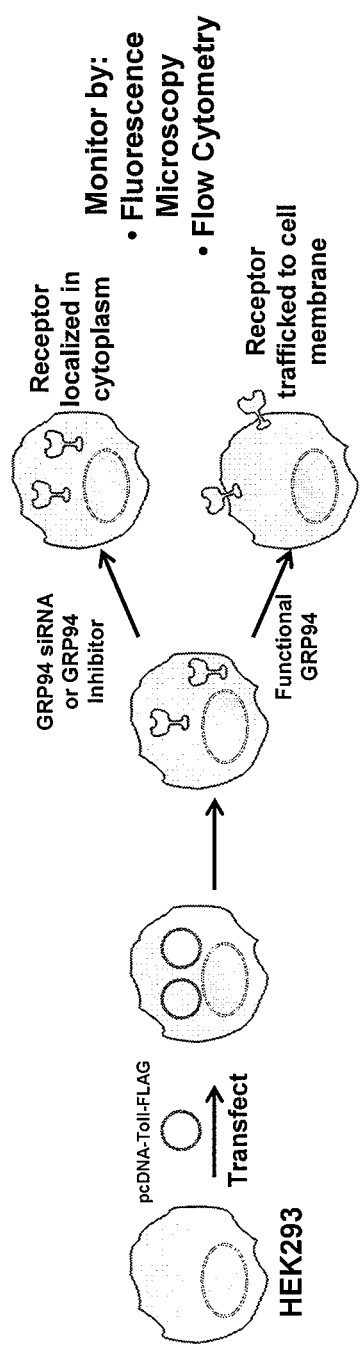
FIG. 4 illustrates the Toll trafficking assay protocol used in the GRP-94 specific assay as described in Example 2.

Prior studies by Nicchitta have shown that the Toll receptors are solely dependent upon GRP94 for their trafficking to the cell membrane, as illustrated in FIG. 4. Thus, they have used surface expression of Toll to monitor GRP94-mediated trafficking, which in the presence of siRNA targeting GRP94, little to no Toll is presented at the cell surface. HEK293 cells stably expressing a GRP94 siRNA or scrambled siRNA are transfected with a plasmid encoding the expression of TOLL, the *drosophila* homologue of the human unterleukin 1 receptor. After transfection, cells are treated with Hsp90 inhibitors for 24 hours. After drug tteatment the surface expression of Toll is monitored by either fluorescence microscopy or flow cytometry. The trafficking of Toll to the cell surface is dependent on GRP94. Cells deficient in GRP94 (i.e. GRP94 siRNA) or cells that have been treated with GRP94 inhibitor will show reduced expression of Toll. Western blots are then used to monitor the depletion of Hsp90α/β client proteins. Compounds that inhibit Toll trafficking that do not cause Hsp90α/β client protein degradation are said to be selective GRP94-selective inhibitors.

Specifically, HEK293 cells were plated in 6-well cell culture, treated plates in Dulbecco's Modified Eagle Medium (1×DMEM) supplemented with 10% fetal bovine serum containing no antibiotics and were maintained at 37° C., 5% CO$_2$, and 95% relative humidity. After 24 hours, the cells (95% confluence) were transfected with pcDNA6B-Toll-Flag using Lipofectamine-2000 according to the manufacturer's instructions. Cells were transfected for 16 h, then were trypsinized and plated in 96-well microscopy-quality, black walled plates that had been pre-treated with attachment factor. After 3 hr incubation at 37° C. to allow the cells to attach, compound at varying concentrations in DMSO (1% DMSO final concentration) was added and cells were returned to incubator for 24 h. After 24 h, the media was removed and cells were fixed in freshly made 4% paraformaldehyde in Dulbecco's Phosphate Buffered Saline (DPBS) for 10 min at 25° C. Cells were washed twice with DPBS then stained with Wheat Germ Agglutinin-Texas Red (5 µg/mL in DPBS, 60 min, 25° C.). Cells were washed twice with DPBS, blocked in 5% bovine serum albumin (BSA, 10 min, 25° C.) followed by staining for 16 h with an anti-Toll antibody (1:200 in 5% BSA/DPBS, 4° C., Santa Cruz, sc-33741). Cells were washed twice with DPBS and stained with an anti-rabbit-AlexaFluor488 antibody (1:300 in DPBS, 25° C., Invitrogen, A-11008) for 3 h at 25° C. Cells were then washed twice with DPBS after which DAPI was added (1 µM in DPBS). Cells were imaged using an inverted Olympus IX-71 microscope with a 60x long working distance air objective using appropriate filter sets for the various tags (AlexaFluor488, Texas Red, DAPI). Images were processed using SlideBook5.0 and analyzed using Cell-Profiler and CellProfiler Analyst.

FIG. 2 shows images and analysis of Compound 2 (BnIm) compared to cRDA utilizing this assay, as well as ratios of cytoplasmic Hsp90 $IC_{50}$/GRP94 $IC_{50}$ for GDA, cis-RDA and BnIm. Representative Western blots of cytosolic Hsp90 client proteins (Akt and Raf) from HEK293 cells treated with either BnIm or cRDA are also shown in FIG. 2. Fluorescence microscopy images of HEK293 cells stably transfected with siRNA targeting GRP94 (94 KD) or scrambled siRNA (94+) are shown in FIG. 2. Cells were transfected with Toll receptor and 94+ cells were subsequently treated with either BnIm or cRDA; Blue=DAPI; Green=Toll; Cells were fixed in 4% PFA, then stained with anti-Toll antibody followed by the appropriate AlexaFluor488-conjugated secondary antibody.

As demonstrated with compound BnIm (SA1, compound 2), the effects of siRNA can be mimicked by inhibiting GRP94. Furthermore, as evidenced by the Western blot shown in FIG. 2, no inhibition of cytoplasmic Hsp90 was observed, providing the first highly selective GRP94 inhibitor to date (>100:1 selectivity).

Example 4

Prostate Cancer Cell Line

Western Blot

The steroid hormone receptors are dependent upon the Hsp90 protein folding machinery for activation and hormone binding. To determine whether test compounds have a similar effect on the androgen receptor, the test compounds can be tested in both a mutated androgen receptor-dependent prostate cancer cell line (LNCaP) and a wild type androgen receptor prostate cancer cell line (LAPC-4). More specifically, the prostate cancer cells are grown in RPMI with 10% fetal calf serum in a standard fashion. Once the cells approach confluence, they are treated with vehicle (DMSO) or varying concentrations of test compounds ranging from 10 nm to 100 µM for 24 hours. Cells are harvested and cell lysates prepared.

More specifically, Western blot analysis is performed on the cell lysate utilizing commercially available antibodies against the androgen receptor, AKT, HIF-1α, Her2, and Hsp90. Actin is used as the control. Western Blot analysis protein concentrations in serum samples can be determined by the Pierce BCA protein assay kit according to the manufacturer's protocol. Western blot analysis (100 mg total protein/lane to start) is electrophoresed under reducing conditions on a SDS-PAGE gel. The separated proteins are transferred to a polyvinylidene difluoride membrane (Millipore, Bedford, Mass.) for 40 minutes at 80 V. The membranes are blocked for two hours at room temperature in Tris-buffered saline (pH 7.5) containing 0.2% I-block (Tropix, Bedford, Mass.), 1% milk, and 0.1% Tween-20 (TBS-T). The membranes are subsequently incubated with a primary antibody to the above mentioned proteins (all of which have commercially available antibodies) overnight at 4° C. The next day the membrane is washed three times in TBS-T followed by one hour incubation with an appropriate horseradish peroxidase labeled secondary antibody in blocking buffer (TBS-T). The membranes are again washed in TBS-T and Tris-buffered saline and developed in SuperSignal West Pico Chemiluminescent Substrate (Pierce, Rockford, Ill.) according to manufacturer's instructions. The blots are visualized by exposing the enhanced chemiluminescence-reacted blot to X-ray film.

Example 5

Grp94 Immunoprecipitation

Detergent lysates of the indicated cells were immunoprecipitated with 9G10 monoclonal anti-Grp94 (StressGen, Vancouver, BC) followed by protein G-Sepharose (Sigma Chemicals or Pierce) as described in Melnick, J.; Dul, J. L.; Argon, Y. Sequential interaction of the chaperones BiP and GRP94 with immunoglobulin chains in the endoplasmic reticulum. Nature 1994, 370, 373-375.

Example 6

IGF-II Secretion

C2C12 cells (ATCC, Rockville, Md.) were induced to differentiate either by complete withdrawal of serum or by shifting to medium supplemented with 2% house serum. 17AAG at concentrations of 10-15 µM in DMSO was used to inhibit Grp94 activity. Cell growth was measured with the XTT formazan colorimetric assay (Roche), cells were grown in 3% serum, to limit the background of the assay.

For IGF-II ELISA, plates were coated with anti-IGF-II (MAb 792, R&D Systems) and incubated with the test cell media. The bound IGF-II was detected with a biotinylated anti-IGF-II antibody (BAF792, R&D Systems) and developed with streptavidin-HRP (R&D Systems) according to the manufacturer's recommended procedure. Optical density units were converted to concentrations of the growth factor with a standard curve generated with recombinant IGF-II (792-MG) (R&D Systems). Data were acquired in duplicate on a microtiter-plate reader (Dynatech Laboratories, Chantilly, Va.) at 450 nm.

Example 7

*Drosophila*

Compound effects on *Drosophila* larval growth were examined as described in 26. Briefly, w1118 *Drosophila* embryos were collected and groups of 20-30 were transferred to plates containing fly food (molasses, corn meal, yeast extract, and agar) supplemented with the indicated concentrations of compound 2 diluted in DMSO. Control (no drug)

plates contained equivalent concentrations of DMSO. Feeding/growth experiments were conducted for 96 hours (third instar), larvae were then immobilized by transferring to PBS supplemented with 5 mM EGTA and imaged on a Leica MZ FLIII stereomicroscope.

Example 8

Prostate Cancer Xenograft Model

The in vivo effect of the compounds of the disclosure can be tested using, for example, a prostate cancer mouse model. More specifically, four to six week old BALB/c nu/nu nude mice can be obtained commercially and maintained in ventilated cages under Institutional Animal Care and Use Committee approval. Separate male mice are inoculated subcutaneously with $10^6$ LNCaP cells suspended in 0.25 mL of Matrigel (BD, Bioscience, Bedford Mass.). Stable serum testosterone levels will be maintained in the mice by the implantation of 12.5 mg 90-day sustained release testosterone pellets (Innovative Research, Sarasota Fla.) subcutaneously prior to inoculation with tumor. Tumor volume will be measured twice a week with vernier calipers with tumor volumes calculated using the formula [length×width×height×0.52]. Mice with established tumor volumes of 5 mm will be selected for KU-1/A4 administration. Utilizing the paradigm for administration of 17-AAG (another Hsp90 inhibitor), animals will be treated with both continuous and intermittent dosing schedules. A control animal will be treated with vehicle alone (DMSO). For the continuous dosing schedule, mice will receive intraperitoneal injections of vehicle or the test compounds (e.g., KU-1/A4) for 5 days per week for 3 weeks. The intermittent group will receive one 5 day cycle and then monitored for progression.

Differing doses of the test compound will be utilized based on pharmacokinetic information obtained from toxicity studies. When progression occurs, as defined by an increase in tumor size, the mice will receive a second 5 day cycle of the test compound. Response to the test compound will be assessed by measuring tumor volume and serum PSA levels using the PSA Assay Kit (American Qualex Antibodies, San Clemente, Calif.). Further response will be assessed by harvesting the tumor at euthanasia and performing immunohistochemistry and western blot analysis of the Hsp90's client proteins known to be involved in cancer cell survival mechanisms such as signal transduction (e.g., AKT, Her2, PI3kinase), angiogenesis (e.g., HIF-1α), and metastasis (AR, MMP2). Each dose and control will be repeated three times to confirm results.

Statistical analysis will be performed to compare the average tumor volume over time between the different doses of the test compound and the control animals. A Wilcoxon sum-rank test, for example, can be used to statistically compare PSA levels in the treatment and control group. Immunohistochemistry results can be assessed qualitatively based on staining intensity graded on a scale of 1 to 5.

To investigate toxicity, four to six week old BALB/c nu/nu nude mice will be obtained commercially and maintained in ventilated cages under Institutional Animal Care and Use Committee approval. Intraperitoneal injections of the test compound (e.g., KU-1/A4) will be given to non-tumor bearing mice at ranges of 25 mg/kg to 200 mg/kg 5 days a week for 3 weeks based on similar concentrations used for 17AAG. Serum samples will be obtained on days 5, 10, and 15. Serum chemistry and liver function analysis will be performed. Serum concentrations of test compound will be determined by high performance liquid chromatography (HPLC). At sacrifice by $CO_2$ euthanasia, a complete blood count, gross necropsy and liver and kidney histopathology will be performed on the animals to determine toxicity. The maximal tolerated dose will be calculated using up/down toxicity studies that will be used as the upper limit of dose for treatment.

Example 9

Neuroprotective Effects

Low concentrations of the Hsp90 inhibitor GDA were reported to induce expression of both Hsp70 and Hsp90, with a concomitant reduction in phosphorylated Tau (Dou et al., 2003). In this example, the test compounds will be tested for protective effects against Aβ toxicity in primary neurons. See protocols in Michaelis et al., (2005) B-Amyloid induced neurodegeneration and protection by structurally diverse microtubule-stabilizing agents. J Pharmacol Exp Ther 312:659-668, which is incorporated by reference.

Example 10

Degradation of Phospho-AKT

Inhibition of Hsp90 results in the degradation of Hsp90-dependent clients via ubiquitination of the unfolded client followed by proteasome-mediated hydrolysis. To test whether Hsp90 client proteins were degraded in the presence of these novobiocin analogues, each compound from Example 1 can be incubated with $SKBr_3$ breast cancer cells at a concentration of 100 μM. Western blot analysis of the protein lysates will be used to demonstrate whether the compounds are capable of causing the degradation of the Hsp90-dependent oncogenic client protein, phospho-AKT. Phospho-AKT is selected as a client protein for this assay because of previous reports indicating that phospho-AKT is a more sensitive indicator of Hsp90 inhibition than AKT. Geldanamycin (GDA, 0.5 μM) can be used as a positive control for Hsp90 inhibition.

Example 11

Degradation of HER-2

The $IC_{50}$ for Hsp90 inhibitors is sometimes determined as the concentration of inhibitor required to produce 50% degradation of Her-2, another therapeutically important Hsp90 client protein involved in breast cancer. Test compounds can be incubated with Skbr3 breast cancer cells at concentrations of 100 nM, 1 μM and 10 μM, lysed and analysed by Western blot. These data will be normalized against actin, a non-Hsp90 client protein, which will be used as a control for non-specific degradation.

Example 12

Cytotoxicity. Quantification of Cell Survival/Proliferation

The in vitro biological activity of the compounds can be evaluated as growth-inhibitory potential in, e.g., MCF-7 human breast cancer cells. Cells are seeded in 96-well plates at 5000 cells/well, and after 24 h, serial dilutions of drugs are added. After 72 h, 3-(4,5-dimethylthiazol-2-yl)-2,5diphenyltetrazolium bromide (MTT, Sigma) (500 ig/mL) is added to each well during 3 h at 37° C. Medium is removed and MTT formazan crystals are dissolved in 100 iL of DMSO followed by gentle agitation for 10 min. The absorbance of converted dye which directly correlates with the number of viable cells is measured at 570 nm with background substraction at 650 nm using a spectrophotometric microtiter reader (Metertech, 960, Fisher-Bioblock, Illkirch, France). All determinations are carried out, e.g., in sextuplate, and each experiment is repeated, e.g., three times. The percentage of survival is calculated as the absorbance ratio of treated to untreated cells. The $IC_{50}$ values are determined as the drug concentrations that inhibit cell growth by 50% compared with growth of vehicle-treated cells. See LaBras et al., 2007, J. Med. Chem., 50, 6189-6200, which is incorporated herein by reference.

Example 13

Cell Extracts and Western Blots

Western Blotting.

Briefly, HEK293 cells were plated in 6-well plates and treated with various concentrations of drug, GDA in DMSO (1% DMSO final concentration), or vehicle (DMSO) for 24 h. Cells were harvested in cold PBS and lysed in mammalian protein extraction reagent (MPER, Pierce) and protease inhibitors (Roche) on ice for 1 h. Lysates were clarified at 14,000 g for 10 min at 4° C. Protein concentrations were determined with the Pierce BCA assay kit per the manufacturer's instructions. Equal amounts of protein (10 µg) were electrophoresed under reducing conditions, transferred to a PVDF membrane, and immunoblotted with the corresponding specific antibodies. Membranes were incubated with an appropriate horseradish peroxidase-labeled secondary antibody, developed with chemiluminescent substrate, and visualized.

The potency of the compounds of the disclosure can be further assessed in MCF-7 cells by the depletion of HER2, Raf-1, and cdk4, the most widely studied molecular signatures indicative of Hsp90 blockade.

Cells are grown to 50% confluence in 60-mm dishes before exposure to various agents as indicated in the text and figure legends. Cells are rinsed in PBS, scraped into PBS, collected by centrifugation, and resuspended in ice-cold lysis buffer (Tris-HCl 50 mM (pH 7.5), NaCl 150 mM, EGTA 1 mM, glycerol 10% (v/v), Triton X-100 1%, MgCl2 1.5 mM, NaF 10 mM, Na pyrophosphate 10 mM, $Na_3VO4$ 1 mM) plus protease inhibitors (Complete reagent, Roche Diagnostics, Indianapolis, Ind.) and kept on ice for 15 min with occasional vortexing. Insoluble debris are removed by centrifugation at 15 000 g for 5 min at 4° C., and cell lysates are boiled in Laemmli sample buffer for 3 min. TCEs are obtained from pelleted cells by resuspension in lysis buffer for 30 min at 4° C. and boiling for 5 min in Laemmli sample buffer. Protein concentration is determined by the Bio-Rad Assay. Equal amounts of protein (20 ig) are fractionated by 8% or 12% SDS-polyacrylamide gel electrophoresis (SDS-PAGE) and transferred onto Immobilon-P membranes (Millipore, Saint Quentin en Yvelines, France). Membranes are blocked for 1 h at 37° C. with 10% dry nonfat milk in PBS containing 0.1% Tween 20. ERR is detected with the D12 (ER epitope: amino acids 2-185) (Santa Cruz, Calif.) mouse monoclonal anti-ER antibody used at 1 µg/mL in PBST-2% milk overnight at 4° C. The antigen/antibody complexes are detected by incubation with a biotinylated anti-mouse antibody followed by revelation with the avidin-peroxidase complex (Vectastain ABC Elite Kit, Vector Laboratories, Inc., Burlingame, Calif.). Other primary antibodies are: HER2 (C18), Raf-1 (C12), cdk4 (C22), caspase 7 (B5), and PARP (F-2) from Santa Cruz and caspase 8 (1C12) from Cell Signaling (Beverly, Mass.) used at 1 ug/mL. The antigen/antibody complexes are detected with appropriate secondary horseradish peroxidaseconjugated antibodies (Santa Cruz). Blots are developed using the Immobilon Western Detection Reagent (Millipore). Depending on the mobility of the proteins, membranes are either stripped (1 h at 50° C. in a medium containing 62.5 mM Tris-HCl pH 6.8, 2% SDS, and 100 mM 2-mercaptoethanol) or extensively washed before reprobing with different primary antibodies. Equal protein loading is assessed by examination of the intensities of nonspecific (NS) signals elicited by the commercial antibodies used and unresponsive to treatments. See, for example, LaBras et al., 2007, J. Med. Chem., 50, 6189-6200, which is incorporated herein by reference.

Example 14

Flow Cytometry Analysis

Flow cytometry can be used to correlate the weak or strong growth inhibitory activity of the compounds of the disclosure with their ability to slightly or markedly affect cell cycle and/or induce cell cycle arrest or apoptosis, respectively. The percentage of cells in each phase $SubG_1$, $G_0/G_1$, S and $G_2/M$ phases of the cell cycle can be determined. See, for example, LaBras et al., 2007, J. Med. Chem., 50, 6189-6200, which is incorporated herein by reference.

Cells ($1.3 \times 10^5$ cells/mL) can be cultured in the presence or not of the compounds of the disclosure at, e.g., 200 uM. Novobiocin, e.g., at the same concentration can be used as a reference inhibitor. After treatment for 48 and 72 h, cells are ished and fixed in PBS/ethanol (30/70). For cytofluorometric examination, cells ($10^4$) are incubated for 30 min in PBS/Triton X100, 0.2%/EDTA 1 mM, and propidium iodide (PI) (50 ug/mL) in PBS supplemented by RNase (0.5 mg/mL). The number of cells in the different phases of the cell cycle is determined, and the percentage of apoptotic cells is quantified. Analyses can be performed, e.g., with a FACS Calibur (Becton Dickinson, Le Pont de Claix, France). Cell Quest software, e.g., can be used for data acquisition and analysis.

Example 15

Multiple Sclerosis-EAE Model

The neurodegenerative disorder multiple sclerosis is often studied in an animal model system termed experimental autoimmune encephalomyelitis ("EAE"). EAE is an inflammatory condition characterized by multifocal perivascular CNS inflammatory infiltrates that primarily include T cells and monocytes. Bar-Or et al., Molecular pathogenesis of multiple sclerosis, Journal of Neuroimmunol. 100 252-259 (1999), which is incorporated herein by reference. EAE can be induced in animals by injection of immunodominant peptides from myelin proteins such as myelin basic protein (MBP), proteolipid protein (PLP), and myelin oligodendrocyte glycoprotein (MOG), or by transfer of CD4+ MHC class II-restricted T-cells reactive with these peptides. See Mokhtarian et al., Nature 309 312-314 (1984); Zamvil et al., T-cell clones specific for myelin basic protein induce chronic relapsing paralysis and demyelination, Nature 317 355-358 (1985). The EAE models are frequently used to study the pathogenesis of MS and to test novel therapeutic strategies aimed at treating MS.

Heat shock response (HSR) suppresses inflammatory gene expression for nitric oxide synthase, cytokines and chemokines, all of which have been implicated in the development of multiple sclerosis (MS). HSR can be induced by a variety of stresses, including hyperthermia, oxidative stress, heavy metals, viral infection, and UV irradiation. Administration of Hsp90 inhibitors also leads to a HSR due to the dissociation of HSF-1 from Hsp90. Therefore, the compounds of the disclosure can be evaluated in a murine autoimmune disease model (Experimental Autoimmune Encephalomyelitis, or Experimental Allergic Encephalitis; EAE) to determine if disease severity and disease incidence is diminished.

For example, to evaluate the in vivo activity, SJL/J female mice at 6 to 8 weeks of age can be divided into three groups with ten mice in each group. The first group is the negative control. For the treated and positive control groups, at the initiation state (Day 0), all mice (10/group) are immunized by intradermal ("i.d.") inoculation with 200 ug of proteolipid protein ("PLP" in a 0.2 mL emulsion with equal volumes of phosphate buffered saline ("PBS") and complete Freund's adjuvant ("CFA") (Difco, Detroit Mich.). The injection volume is 100 uL at each injection site. Then, each mouse in the treated group receives intravenous ("i.v.") injections of 0.5 mg/kg of test compound on day 0 and on day 10.

Disease progression is evaluated using a clinical scoring scale ranging from 0 to 5. The score of disease progression in the mouse EAE model Score Gross Pathology 0 No clinical disease, 0.5 Tail weakness, 1 Tail completely flaccid, 2 Paraparesis (weakness, incomplete paralysis of one or two hind limbs), 3 Paraplegia (complete paralysis of two hind limbs), 4 Paraplegia with forelimb weakness, or paralysis 5 Moribund or death.

All of the immunized mice are to be scored blindly for about 7 weeks by the same observer. Mean daily clinical scores are calculated by adding the grades of each mouse individually divided by the number of mice in each group. All animals are to be observed daily and, upon signs of paralysis and weakness, moistened food was provided to the animals to prevent dehydration.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

REFERENCES

1. Hartl, F. U. Molecular chaperones in cellular protein folding. *Nature* 1996, 381, 571-580.
2. Hartl, F. U.; Bracher, A.; Hayer-Hartl, M. Molecular chaperones in protein folding and proteostasis. *Nature* 2011, 475, 324-332.
3. Whitesell, L.; Bagatell, R.; Falsey, R. The stress response: implications for the clinical development of Hsp90 inhibitors. *Curr. Cancer Drug Tar.* 2003, 3, 349-358.
4. Whitesell, L.; Lindquist, S. L. Hsp90 and the chaperoning of cancer. *Nat. Rev. Cancer* 2005, 5, 761-772.
5. Bishop, S. C.; Burlison, J. A.; Blagg, B. S. J. Hsp90: a novel target for the disruption of multiple signaling cascades. *Curr. Cancer Drug Tar.* 2007, 7, 369-388.
6. Blagg, B. S. J.; Kerr, T. D. Hsp90 inhibitors: small molecules that transform the Hsp90 protein folding machinery into a catalyst for protein degradation. *Med. Res. Rev.* 2006, 26, 310-338.
7. Chiosis, G.; Vilenchik, M.; Kim, J.; Solit, D. Hsp90: the vulnerable chaperone. *Drug Discov. Today* 2004, 9, 881-888.
8. Zhang, H.; Burrows, F. Targeting multiple signal transduction pathways through inhibition of Hsp90. *J. Mol. Med.* 2004, 82, 488-499.
9. Hanahan, D.; Weinberg, R. A. The hallmarks of cancer. *Cell* 2000, 100, 57-70.
10. Hanahan, D.; Weinberg, Robert A. Hallmarks of cancer: The next generation. *Cell* 2011, 144, 646-674.
11. Workman, P. Combinatorial attack on multistep oncogenesis by inhibiting the Hsp90 molecular chaperone. *Cancer Lett.* 2004, 206, 149-157.
12. Workman, P.; Burrows, F.; Neckers, L.; Rosen, N. Drugging the cancer chaperone Hsp90: Combinatorial therapeutic exploitation of oncogene addiction and tumor stress. *Ann. NY Acad. Sci.* 2007, 1113, 202-216.
13. Dutta, R.; Inouye, M. GHKL, An emergent ATPase/kinase superfamily. *Trends Biochem. Sci.* 2000, 25, 24-28.
14. Kim, Y. S.; Alarcon, S. V.; Lee, S.; Lee, M. J.; Giaccone, G.; Neckers, L.; Trepel, J. B. Update on Hsp90 inhibitors in clinical trial. *Curr. Top. Med. Chem.* 2009, 9, 1479-1492.
15. Biamonte, M. A.; Van de Water, R.; Arndt, J. W.; Scannevin, R. H.; Perret, D.; Lee, W. Heat shock protein 90: inhibitors in clinical trials. *J. Med. Chem.* 2010, 53, 3-17.
16. Holzbeierlein, J.; Windsperger, A.; Vielhauer, G. Hsp90: A Drug Target? *Curr. Oncol. Rep.* 2010, 12, 95-101.
17. Sreedhar, A. S.; Kalmar, E.; Csermely, P. Hsp90 isoforms: functions, expression and clinical importance. *FEBS Lett* 2004, 562, 11-15.
18. Dollins, D. E.; Immormino, R. M.; Gewirth, D. T. Structure of unliganded GRP94, the ER Hsp90: Basis for nucleotide-induced conformational change. *J. Biol. Chem.* 2005, 280, 30438-30447.
19. Dollins, D. E.; Warren, J. J.; Immormino, R. M.; Gewirth, D. T. Structures of GRP94-nucleotide complexes reveal mechanistic differences between the hsp90 chaperones. *Mol. Cell.* 2007, 28, 41-56.
20. Immormino, R. M.; Dollins, D. E.; Shaffer, P. L.; Soldano, K. L.; Walker, M. A.; Gewirth, D. T. Ligand-induced conformational shift in the N-terminal domain of GRP94, an Hsp90 chaperone. *J. Biol. Chem.* 2004, 279, 46162-46171.
21. Immormino, R. M.; Metzger Iv, L. E.; Reardon, P. N.; Dollins, D. E.; Blagg, B. S. J.; Gewirth, D. T. Different Poses for Ligand and Chaperone in Inhibitor-Bound Hsp90 and GRP94: Implications for Paralog-Specific Drug Design. *J. Mol. Biol.* 2009, 388, 1033-1042.
22. Krukenberg, K. A.; Bottcher, U. M.; Southworth, D. R.; Agard, D. A. Grp94, the endoplasmic reticulum Hsp90, has a similar solution conformation to cytosolic Hsp90 in the absence of nucleotide. *Protein Sci.* 2009, 18, 1815-1827.
23. Krukenberg, K. A.; Southworth, D. R.; Street, T. O.; Agard, D. A. pH-dependent conformational changes in bacterial Hsp90 reveal a Grp94-like conformation at pH 6 that is highly active in suppression of citrate synthase aggregation. *J. Mol. Biol.* 2009, 390, 278-291.
24. Soldano, K. L.; Jivan, A.; Nicchitta, C. V.; Gewirth, D. T. Structure of the N-terminal domain of GRP94. Basis for ligand specificity and regulation. *J. Biol. Chem.* 2003, 278, 48330-48338.
25. Marzec, M.; Eletto, D.; Argon, Y. GRP94: An HSP90-like protein specialized for protein folding and quality control in the endoplasmic reticulum. *BBA—Mol. Cell. Res.* 2012, 1823, 774-787.
26. Maynard, J. C.; Pham, T.; Zheng, T.; Jockheck-Clark, A.; Rankin, H. B.; Newgard, C. B.; Spana, E. P.; Nicchitta, C. V. Gp93, the *Drosophila* GRP94 ortholog, is required for gut epithelial homeostasis and nutrient assimilation-coupled growth control. *Dev. Biol.* 2010, 339, 295-306.

27. McLaughlin, M.; Vandenbroeck, K. The endoplasmic reticulum protein folding factory and its chaperones: new targets for drug discovery? *Brit. J. Pharmacol.* 2011, 162, 328-345.
28. Wanderling, S.; Simen, B. B.; Ostrovsky, O.; Ahmed, N. T.; Vogen, S. M.; Gidalevitz, T.; Argon, Y. GRP94 Is Essential for Mesoderm Induction and Muscle Development Because It Regulates Insulin-like Growth Factor Secretion. *Mol. Biol. Cell* 2007, 18, 3764-3775.
29. MvLaughlin, M.; Alloza, I.; Vandenbroeck, K. Different chaperone usage by IL-12 and IL-23 during their assembly reveals novel targets for intervention with cytokine secretion in neuroinflammation. *Neuroimmunol.* 2008, 203, 268.
30. Olson, D. L.; Burkly, L. C.; Leone, D. R.; Dolinski, B. M.; Lobb, R. R. Anti-α4 integrin monoclonal antibody inhibits multiple myeloma growth in a murine model. *Molecular Cancer Therapeutics* 2005, 4, 91-99.
31. Ostrovsky, 0.; Eletto, D.; Makarewich, C.; Barton, E. R.; Argon, Y. Glucose regulated protein 94 is required for muscle differentiation through its control of the autocrine production of insulin-like growth factors. *Biochimica et Biophysica Acta (BBA)—Molecular Cell Research* 2010, 1803, 333-341.
32. Randow, F.; Seed, B. Endoplasmic reticulum chaperone gp96 is required for innate immunity but not cell viability. *Nat Cell Biol* 2001, 3, 891-896.
33. Saitoh, T.; Yanagita, T.; Shiraishi, S.; Yokoo, H.; Kobayashi, H.; Minami, S.-i.; Onitsuka, T.; Wada, A. Down-Regulation of Cell Surface Insulin Receptor and Insulin Receptor Substrate-1 Phosphorylation by Inhibitor of 90-kDa Heat-Shock Protein Family: Endoplasmic Reticulum Retention of Monomeric Insulin Receptor Precursor with Calnexin in Adrenal Chromaffin Cells. *Molecular Pharmacology* 2002, 62, 847-855.
34. Yang, Y.; Liu, B.; Dai, J.; Srivastava, P. K.; Zammit, D. J.; Lefrancois, L.; Li, Z. Heat shock protein gp96 is a master chaperone for toll-like receptors and is important in the innate function of macrophages. *Immunity* 2007, 26, 215-226.
35. Belfiore, A.; Pandini, G.; Vella, V.; Squatrito, S.; Vigneri, R. Insulin/IGF-I hybrid receptors play a major role in IGF-I signaling in thyroid cancer. *Biochimie* 1999, 81, 403-407.
36. Chavany, C.; Mimnaugh, E.; Miller, P.; Bitton, R.; Nguyen, P.; Trepel, J.; Whitesell, L.; Schnur, R.; Moyer, J. D.; Neckers, L. p185 Binds to GRP94 in Vivo. *Journal of Biological Chemistry* 1996, 271, 4974-4977.
37. Moorehead, R. A.; Sanchez, 0. H.; Baldwin, R. M.; Khokha, R. Transgenic overexpression of IGF-II induces spontaneous lung tumors: a model for human lung adenocarcinoma. *Oncogene* 2003, 22, 853-857.
38. Supino-Rosin, L.; Yoshimura, A.; Yarden, Y.; Elazar, Z.; Neumann, D. Intracellular Retention and Degradation of the Epidermal Growth Factor Receptor, Two Distinct Processes Mediated by Benzoquinone Ansamycins. *Journal of Biological Chemistry* 2000, 275, 21850-21855.
39. Zuany-Amorim, C.; Hastewell, J.; Walker, C. Toll-like receptors as potential therapeutic targets for multiple diseases. *Nat Rev Drug Discov* 2002, 1, 797-807.
40. McLaughlin, M.; Vandenbroeck, K. The endoplasmic reticulum protein folding factory and its chaperones: new targets for drug discovery? *British Journal of Pharmacology* 2011, 162, 328-345.
41. Clevenger, R. C.; Blagg, B. S. J. Design, Synthesis, and Evaluation of a Radicicol and Geldanamycin Chimera, Radamide. *Org. Lett.* 2004, 6, 4459-4462.
42. Hadden, M. K.; Blagg, B. S. J. Synthesis and Evaluation of Radamide Analogues, A Chimera of Radicicol and Geldanamycin. *J. Org. Chem.* 2009, 74, 4697-4704.
43. Shen, G.; Wang, M.; Welch, T. R.; Blagg, B. S. J. Design, Synthesis, and Structure Activity Relationships for Chimeric Inhibitors of Hsp90. *J. Org. Chem.* 2006, 71, 7618-7631.
44. Shen, G.; Blagg, B. S. J. Radester, a Novel Inhibitor of the Hsp90 Protein Folding Machinery. *Org. Lett.* 2005, 7, 2157-2160.
45. Baldwin, J. J.; Engelhardt, E. L.; Hirschmann, R.; Lundell, G. F.; Ponticello, G. S.; Ludden, C. T.; Sweet, C. S.; Scriabine, A.; Share, N. N.; Hall, R. f3-Adrenergic blocking agents with acute antihypertensive activity. *J. Med. Chem.* 1979, 22, 687-694.
46. Radziszewski, B. Glyoxaline and its homologues. *Ber.* 1882, 15, 2706-2708.
47. Randow, F.; Seed, B. Endoplasmic reticulum chaperone gp96 is required for innate immunity but not cell viability. *Nat. Cell Biol.* 2001, 3, 891-896.
48. Istomin, A.; Godzik, A. Understanding diversity of human innate immunity receptors: analysis of surface features of leucine-rich repeat domains in NLRs and TLRs. *BMC Immunology* 2009, 10, 48.
49. Qiu, L.; Song, L.; Xu, W.; Ni, D.; Yu, Y. Molecular cloning and expression of a Toll receptor gene homologue from Zhikong Scallop, Chlamys farreri. *Fish Shellfish Immun.* 2007, 22, 451-466.
50. Sun, J.; Duffy, K. E.; Ranjith-Kumar, C. T.; Xiong, J.; Lamb, R. J.; Santos, J.; Masarapu, H.; Cunningham, M.; Holzenburg, A.; Sarisky, R. T.; Mbow, M. L.; Kao, C. Structural and Functional Analyses of the Human Toll-like Receptor 3. *J. Biol. Chem.* 2006, 281, 11144-11151.
51. Weber, A. N. R.; Morse, M. A.; Gay, N. J. Four N-linked Glycosylation Sites in Human Toll-like Receptor 2 Cooperate to Direct Efficient Biosynthesis and Secretion. *J. Biol. Chem.* 2004, 279, 34589-34594.
52. Carpenter, A.; Jones, T.; Lamprecht, M.; Clarke, C.; Kang, I.; Friman, O.; Guertin, D.; Chang, J.; Lindquist, R.; Moffat, J.; Golland, P.; Sabatini, D. CellProfiler: image analysis software for identifying and quantifying cell phenotypes. *Genome Biol.* 2006, 7, R100.
53. Ostrovsky, O.; Eletto, D.; Makarewich, C.; Barton, E. R.; Argon, Y. Glucose regulated protein 94 is required for muscle differentiation through its control of the autocrine production of insulin-like growth factors. *BBA—Mol. Cell. Res.* 2010, 1803, 333-341.
54. Ostrovsky, O.; Ahmed, N. T.; Argon, Y. The Chaperone Activity of GRP94 Toward Insulin-like Growth Factor II Is Necessary for the Stress Response to Serum Deprivation. *Mol. Biol. Cell* 2009, 20, 1855-1864.
55. Loo, M. A.; Jensen, T. J.; Cui, L.; Hou, Y.-x.; Chang, X.-B.; Riordan, J. R. Perturbation of Hsp90 interaction with nascent CFTR prevents its maturation and accelerates its degradation by the proteasome. *EMBO J.* 1998, 17, 6879-6887.
56. Vogen, S.; Gidalevitz, T.; Biswas, C.; Simen, B. B.; Stein, E.; Gulmen, F.; Argon, Y. Radicicol-sensitive Peptide Binding to the N-terminal Portion of GRP94. *J. Biol. Chem.* 2002, 277, 40742-40750.
57. Edwards, D. P.; Weigel, N. L.; Schrader, W. T.; O'Malley, B. W.; McGuire, W. L. Structural analysis of chicken oviduct progesterone receptor using monoclonal antibodies to the subunit B protein. *Biochemistry* 1984, 23, 4427-4435.
58. Basso, A. D.; Solit, D. B.; Chiosis, G.; Giri, B.; Tsichlis, P.; Rosen, N. Akt Forms an Intracellular Complex with Heat Shock Protein 90 (Hsp90) and Cdc37 and Is Destabilized by Inhibitors of Hsp90 Function. *J. Biol. Chem.* 2002, 277, 39858-39866.
59. Grbovic, O. M.; Basso, A. D.; Sawai, A.; Ye, Q.; Friedlander, P.; Solit, D.; Rosen, N. V600E B-Raf requires the Hsp90 chaperone for stability and is degraded in response to Hsp90 inhibitors. *P. Natl. Acad. Sci.* 2006, 103, 57-62.
60. da Rocha Dias, S.; Friedlos, F.; Light, Y.; Springer, C.; Workman, P.; Marais, R. Activated B-RAF Is an Hsp90 Client Protein That Is Targeted by the Anticancer Drug 17-Allylamino-17-Demethoxygeldanamycin. *Cancer Res.* 2005, 65, 10686-10691.
61. Conde, R.; Belak, Z. R.; Nair, M.; O'Carroll, R. F.; Ovsenek, N. Modulation of Hsf1 activity by novobiocin and geldanamycin. *Biochem. Cell Biol.* 2009, 87, 845-851.
62. McCollum, A. K.; TenEyck, C. J.; Stensgard, B.; Morlan, B. W.; Ballman, K. V.; Jenkins, R. B.; Toft, D. O.; Erlichman, C. P-Glycoprotein—mediated resistance to Hsp90-directed therapy is eclipsed by the heat shock response. *Cancer Res.* 2008, 68, 7419-7427.
63. Banerji, U. Heat shock protein 90 as a drug target: some like it hot. *Clin. Cancer Res.* 2009, 15, 9-14.
64. Benson, J. D.; Chen, Y.-N. P.; Cornell-Kennon, S. A.; Dorsch, M.; Kim, S.; Leszczyniecka, M.; Sellers, W. R.; Lengauer, C. Validating cancer drug targets. *Nature* 2006, 441, 451-456.
65. Isaacs, J. S.; Xu, W. S.; Neckers, L. Heat shock protein as a molecular target for cancer therapeutics. *Cancer Cell* 2003, 3, 213-217.
66. Li, Y.; Schwartz, S. J.; Sun, D. New developments in Hsp90 inhibitors as anti-cancer therapeutics: mechanisms, clinical perspective and more potential. *Drug Resist. Update* 2009, 12, 17-27.
67. Neckers, L. Hsp90 inhibitors as novel cancer chemotherapeutic agents. *Trends Mol. Med.* 2002, 8, S55-S61.
68. Workman, P.; Billy, E. d. Putting the heat on cancer. *Nat. Med.* 2007, 13, 1415-1417.
69. Peterson, L. B.; Blagg, B. S. J. To fold or not to fold: modulation and consequences of Hsp90 inhibition. *Future Med. Chem.* 2009, 1.
70. Taldone, T.; Gozman, A.; Maharaj, R.; Chiosis, G. Targeting Hsp90: small-molecule inhibitors and their clinical development. *Curr. Opin. Pharmacol.* 2008, 8, 370-374.
71. Yaffe, D.; Saxel, O. R. A. Serial passaging and differentiation of myogenic cells isolated from dystrophic mouse muscle. *Nature* 1977, 270, 725-727.
72. Melnick, J.; Dul, J. L.; Argon, Y. Sequential interaction of the chaperones BiP and GRP94 with immunoglobulin chains in the endoplasmic reticulum. *Nature* 1994, 370, 373-375.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth are to be interpreted as illustrative, and not in a limiting sense. Further, it will be understood that certain features and subcombinations are of utility and may be employed without reference to other features and subcombinations. This is contemplated by and is within the scope of the claims.

We claim:
1. A compound or pharmaceutically acceptable salt of Formula (I):

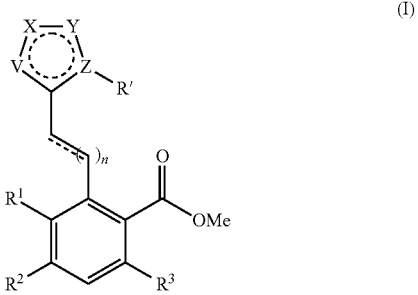

wherein:
V is N;
X is CH;
Y is CH;
Z is selected from C or N;
$R^1$ is selected from the group consisting of H, F, Cl, Br, I, methyl, ethyl, n-propyl, isopropyl, butyl, phenyl, and benzyl;
$R^2$ is selected from the group consisting of H, OH, SH, and $NH_2$;
$R^3$ is selected from the group consisting of H, OH, SH, and $NH_2$;
R' is selected from the group consisting of

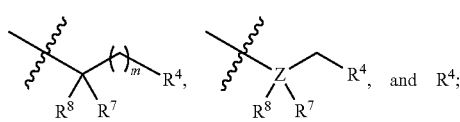

$R^4$ is selected from the group consisting of

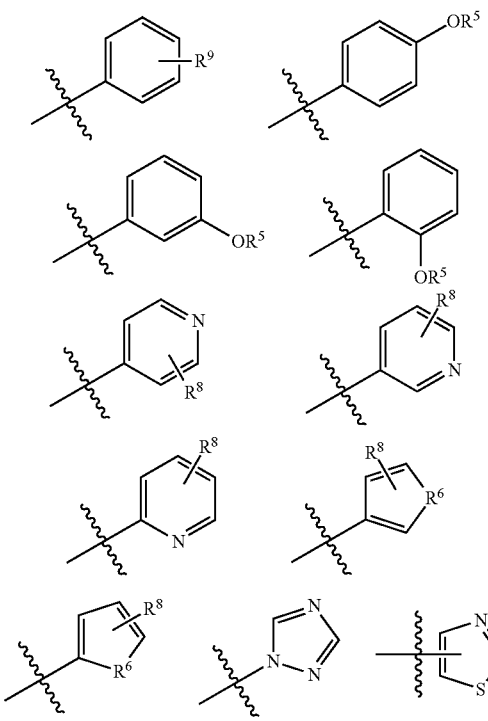

-continued

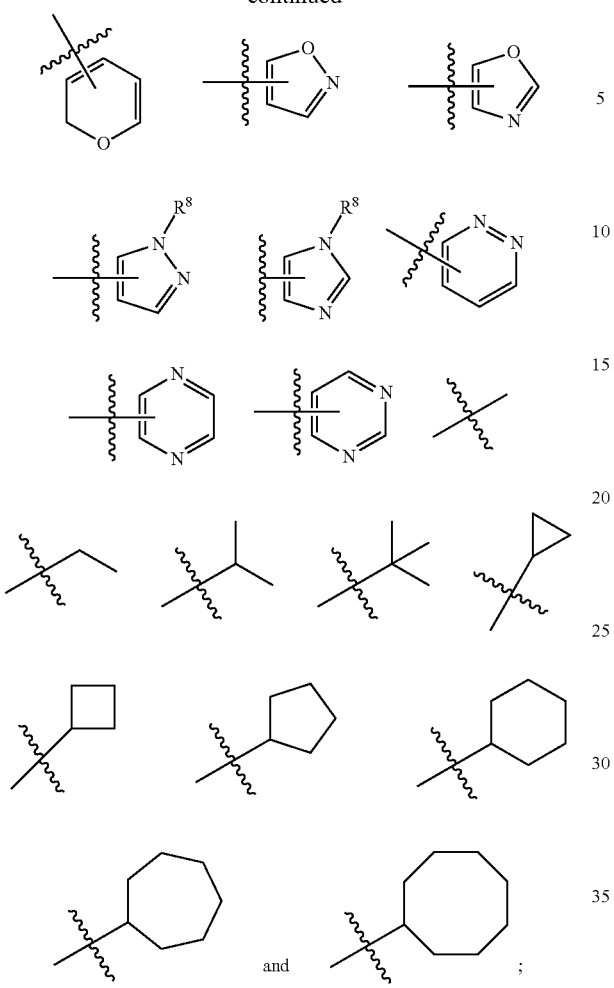

$R^5$ is selected from the group consisting of methyl, ethyl, propyl, isopropyl, butyl, isobutyl, sec-butyl, and tert-butyl;

$R^6$ is selected from the group consisting of O, S, NH, and $CH_2$;

$R^7$ is selected from the group consisting of H, and methyl; and $R^8$ is selected from the group consisting of H, methyl, ethyl, propyl, isopropyl, butyl, isobutyl, sec-butyl, and tert-butyl;

$R^9$ is selected from the group consisting of H, methyl, ethyl, propyl, iso-propyl, butyl, sec-butyl, tert-butyl, halogen, OH, $NH_2$, $NR^{10}H$, $N(R^{10})_2$, and $NCOR^{10}$;

$R^{10}$ is selected from the group consisting of methyl, ethyl, propyl, isopropyl, butyl, sec-butyl, and tert-butyl;

n is selected from 0, 1, 2, or 3, wherein
 when n is 1, --- represents a single or a double bond, wherein the double bond is in the cis or trans configuration, and
 when n is 0, 2 or 3, --- represents a single bond; and m is selected from 0, 1, 2, 3 or 4.

2. The compound or pharmaceutically acceptable salt according to claim 1:

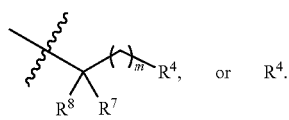

wherein
Z is N.

3. The compound or pharmaceutically acceptable salt according to claim 1 wherein R' is

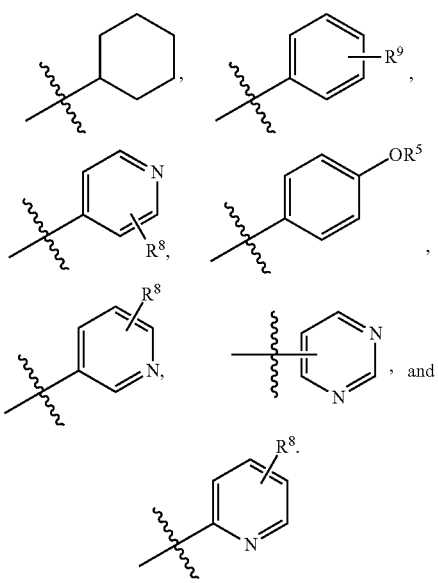

4. The compound or pharmaceutically acceptable salt according to claim 1 wherein
Z is N.

5. The compound or pharmaceutically acceptable salt according to claim 1 wherein $R^1$ is F, Cl, Br, or I.

6. The compound or pharmaceutically acceptable salt according to claim 1 wherein
$R^1$ is Cl;
$R^2$ is OH; and
$R^3$ is OH.

7. The compound or pharmaceutically acceptable salt according to claim 1 wherein $R^4$ is selected from the group consisting of 8. The compound according to claim 1 selected from the group consisting of:

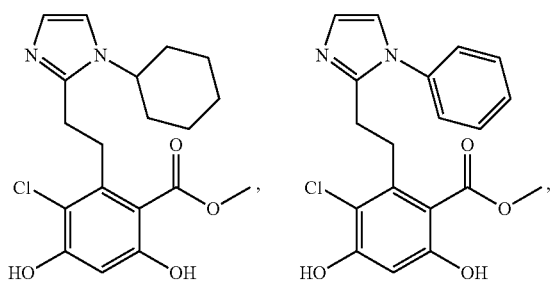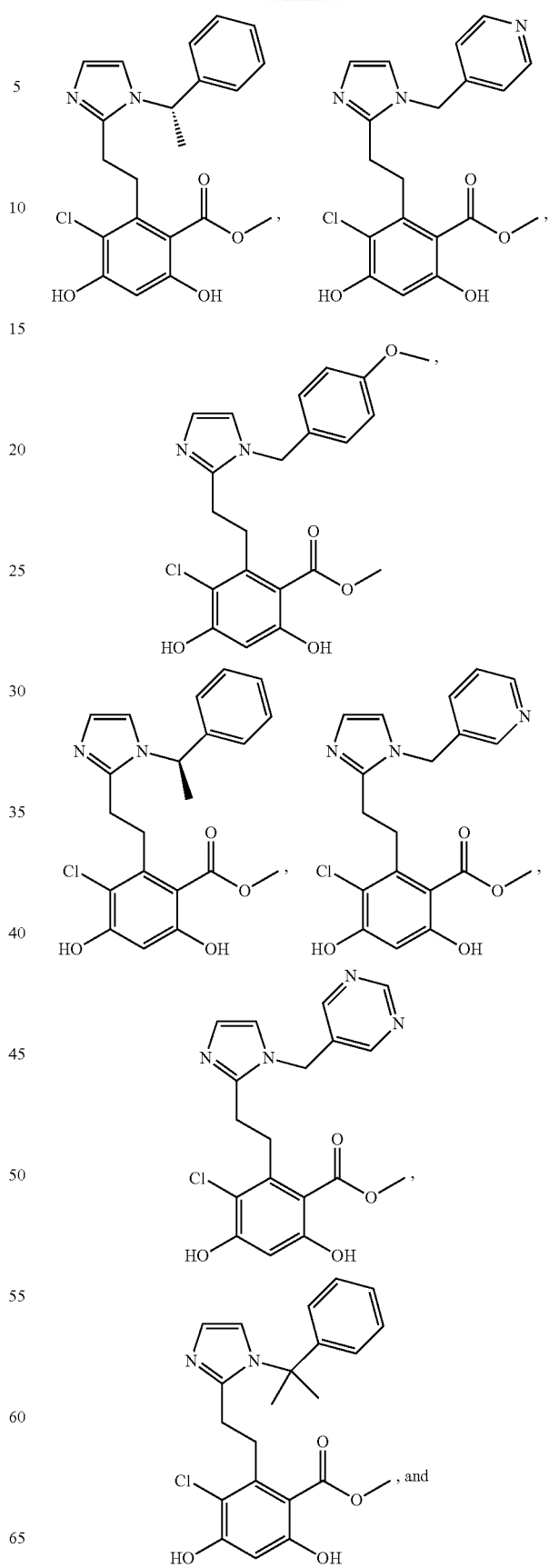

-continued
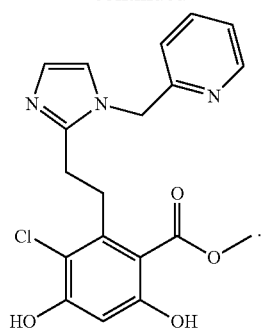 [SMILES: COC(=O)c1c(O)cc(O)c(Cl)c1CCc1nccn1Cc1ccccn1]
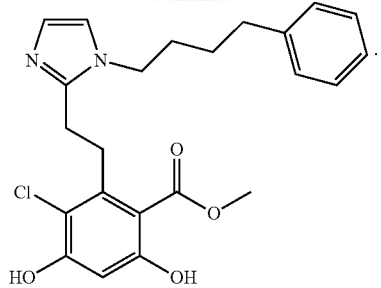
9. The compound according to claim 8 selected from:
10. The compound according to claim 9:
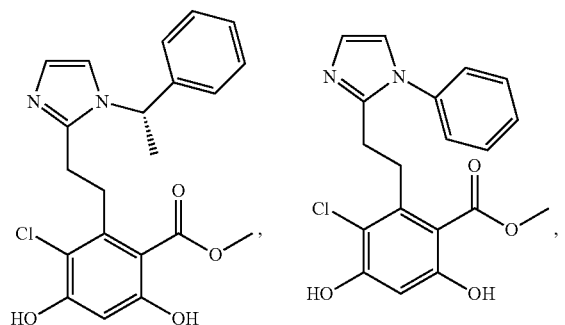
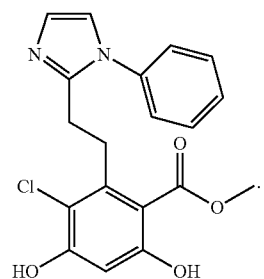
11. The compound according to claim 9:
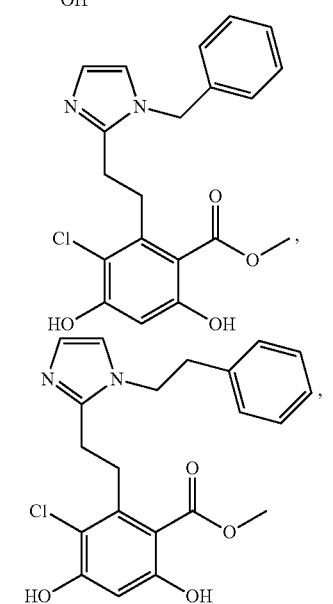
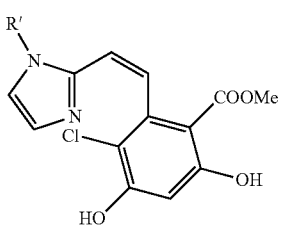
12. The compound or pharmaceutically acceptable salt according to claim 1 of Formula VI:
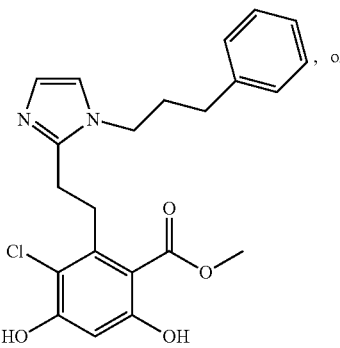

wherein
R' is selected from the group consisting of

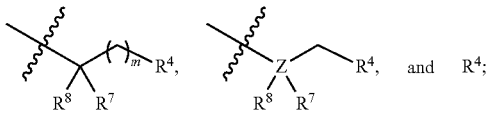

R⁴ is selected from the group consisting of

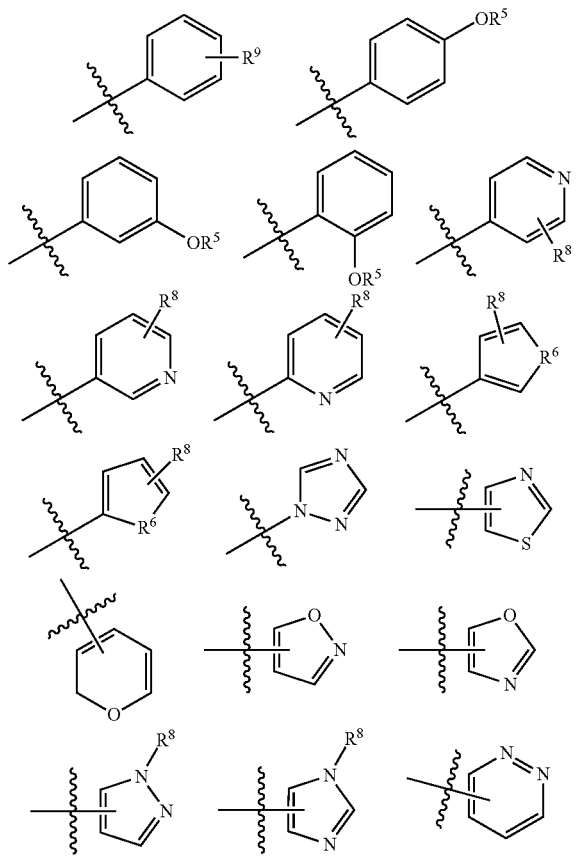

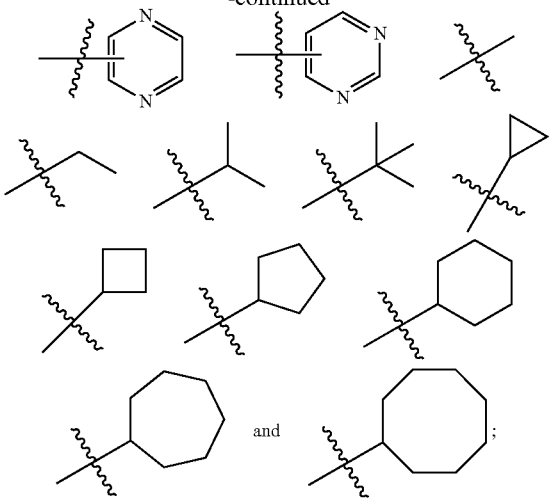

$R^5$ is selected from the group consisting of methyl, ethyl, propyl, isopropyl, butyl, isobutyl, sec-butyl, and tert-butyl;

$R^6$ is selected from the group consisting of O, S, NH, and $CH_2$;

$R^7$ is selected from the group consisting of H, and methyl; and $R^8$ is selected from the group consisting of H, methyl, ethyl, propyl, isopropyl, butyl, isobutyl, sec-butyl, and tert-butyl;

$R^9$ is selected from the group consisting of H, methyl, ethyl, propyl, iso-propyl, butyl, sec-butyl, tert-butyl, halogen, OH, $NH_2$, $NR^{10}H$, $N(R^{10})_2$, and $NCOR^{10}$;

$R^{10}$ is selected from the group consisting of methyl, ethyl, propyl, isopropyl, butyl, sec-butyl, and tert-butyl;

m is selected from 0, 1, 2, 3 or 4;

or a pharmaceutically acceptable salt thereof.

13. A pharmaceutical composition comprising a compound or salt according to claim 1 and a pharmaceutically acceptable carrier.

* * * * *